United States Patent
Mao et al.

(10) Patent No.: US 11,292,000 B2
(45) Date of Patent: Apr. 5, 2022

(54) DEVICES AND METHODS FOR SEPARATING CIRCULATING TUMOR CELLS FROM BIOLOGICAL SAMPLES

(71) Applicant: University of Georgia Research Foundation, Inc., Athens, GA (US)

(72) Inventors: Leidong Mao, Watkinsville, GA (US); Yang Liu, Athens, GA (US); Wujun Zhao, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 237 days.

(21) Appl. No.: 16/406,440

(22) Filed: May 8, 2019

(65) Prior Publication Data
US 2019/0262836 A1 Aug. 29, 2019

Related U.S. Application Data

(63) Continuation-in-part of application No. PCT/US2018/045294, filed on Aug. 4, 2018.
(Continued)

(51) Int. Cl.
*B01L 3/00* (2006.01)
*B03C 1/01* (2006.01)
(Continued)

(52) U.S. Cl.
CPC ..... *B01L 3/502761* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS 6,432,630 B1 8/2002 Blankenstein
9,278,353 B2 3/2016 Smith et al.
(Continued)

FOREIGN PATENT DOCUMENTS

DE 102009005925 A1 7/2017

OTHER PUBLICATIONS

Adams, Daniel L., Stuart S. Martin, Katherine Alpaugh, Monica Charpentier, Susan Tsai, Raymond C. Bergan, Irene M. Ogden, William Catalona, Saranya Chumsri, Cha-Mei Tang and Massimo Cristofanilli, Circulating giant macrophages as a potential biomarker of solid tumors, Proceedings of the National Academy of Sciences of the United States of America, 2014, p. 3514-3519, vol. 111, No. 9, National Academy of Sciences.
(Continued)

*Primary Examiner* — David C Mellon
(74) *Attorney, Agent, or Firm* — Thomas Horstemeyer, LLP

(57) ABSTRACT

A variety of devices, systems, kits, and methods are provided for separating or enriching circulating tumor cells in a biological sample such as whole blood. In some aspects, the devices are multi-stage devices including at least a filtering stage, and two separation stages for ferrohydrodynamic separation of magnetically labelled white blood cells and for marker-independent and size-independent focusing of magnetically labeled particles so as to separate or enrich unlabeled rare cells in the biological sample. The devices and methods are, in some aspects, capable of high throughput in excess of 6 milliliters per hour while achieving high separation (>97%) of the unlabeled rare cells.

20 Claims, 33 Drawing Sheets

Related U.S. Application Data

(60) Provisional application No. 62/826,539, filed on Mar. 29, 2019, provisional application No. 62/668,355, filed on May 8, 2018, provisional application No. 62/541,552, filed on Aug. 4, 2017.

(51) Int. Cl.
  *B03C 1/28* (2006.01)
  *C12M 3/06* (2006.01)
  *B03C 1/32* (2006.01)
  *C12M 1/12* (2006.01)
  *C12M 1/42* (2006.01)

(52) U.S. Cl.
  CPC .......... *B01L 3/502753* (2013.01); *B03C 1/01* (2013.01); *B03C 1/288* (2013.01); *B03C 1/32* (2013.01); *C12M 1/42* (2013.01); *C12M 23/16* (2013.01); *C12M 25/16* (2013.01); *B01L 2200/027* (2013.01); *B01L 2200/0647* (2013.01); *B01L 2200/0652* (2013.01); *B01L 2300/0681* (2013.01); *B01L 2300/087* (2013.01); *B01L 2300/0864* (2013.01); *B01L 2400/043* (2013.01); *B03C 2201/18* (2013.01); *B03C 2201/26* (2013.01)

(56) References Cited

U.S. PATENT DOCUMENTS

| | | | |
|---|---|---|---|
| 2010/0297733 | A1* | 11/2010 | Lin .................. B03C 1/288 435/239 |
| 2012/0080360 | A1* | 4/2012 | Stone ............... B03C 1/288 209/214 |
| 2013/0306566 | A1* | 11/2013 | Mao ................. C12N 13/00 210/695 |
| 2016/0123858 | A1 | 5/2016 | Kapur et al. |
| 2016/0244714 | A1* | 8/2016 | Spuhler .............. G01N 15/1484 |
| 2017/0029782 | A1* | 2/2017 | Mao ................. B01L 3/502776 |
| 2017/0072405 | A1 | 3/2017 | Mao et al. |

OTHER PUBLICATIONS

Antfolk, Maria, Christian Antfolk, Hans Lilja, Thomas Laurell and Per Augustsson, A single inlet two-stage acoustophoresis chip enabling tumor cell enrichment from white blood cells, Lab Chip, 2015, p. 2102-2109, 15, The Royal Society of Chemistry.

Autebert, Julien, Benoit Coudert, Jerome Champ, Laure Saias, Ezgi Tulukcuoglu Guneri, Ronald Lebofsky, Francois-Clement Bidard, Jean-Yves Pierga, Francoise Farace, Stephanie Descroix, Laurent Malquin and Jean-Louis Viovy, High purity microfluidic sorting and analysis of circulating tumor cells: towards routine mutation detection, Lab Chip, 2015, p. 2090-2101, 15, The Royal Society of Chemistry.

Campton, Daniel E., Arturo B. Ramirez, Joshua J. Nordberg, Nick Drovetto, Alisa C. Clein, Paulina Varshavskaya, Barry H Friemel, Steve Quarre, Amy Breman, Michael Dorschner, Sibel Blau, C. Anthony Blau, Daniel E. Sabath, Jackie L. Stilwell and Eric P. Kaldjian, High-recovery visual identification and single-cell retrieval of circulating tumor cells for genomic analysis using a dual-technology platform integrated with automated immunofluorescence strainging, BMC Cancer, 2015, p. 1-13, BioMed Central.

Clawson, Gary A., Eric Kimchi, Susan D. Patrick, Ping XIN, Ramdane Harouaka, Siyang Zheng, Arthur Berg, Todd Schell, Kevin F. Staveley-O'Carroll, Rogerio I. Neves, Paul J. Mosca and Diane Thiboutot, Circulating Tumor Cells in Melanoma Patients, PLoS One, 2012, p. 1-12, vol. 7, Issue: 7, e41052.

Desitter, Isabelle, Bella S. Guerrouahen, Naoual Benali-Furet, Janine Wechsler, Pasi A. Janne, Yanan Kuang, Masahiko Yanagita, Lilin Wang, Jillian A. Berkowitz, Robert J. Distel and Yvon E. Cayre, A New Device for Rapid Isolation by Size and Characterization of Race Circulating Tumor Cells, Anticancer Research, 2011, p. 427-442, 31.

Earhart, Christopher M., Casey E. Hughes, Richard S. Gaster, Chin Chun Ooi, Robert J. Wilson, Lisa Y. Zhou, Eric W. Humke, Lingyun XU, Dawson J. Wong, Stephen B. Willingham, Erich J. Schwartz, Irving L. Weissman, Stefanie S. Jeffrey, Joel W. Neal, Rajat Rohatgi, Heather A. Wakelee and Shan X. Wang, Isolation and mutational analysis of circulating tumor cells from lung cancer patients with magnetic sifters and biochips, Lab Chip, 2014, p. 78-88, 14, The Royal Society of Chemistry.

Fachin, Fabio, Philipp Spuhler, Joseph M. Martel-Foley, Jon F. Edd, Thomas A. Barber, John Walsh, Murat Karabacak, Vincent Pai, Melissa Yu, Kyle Smith, Henry Hwang, Jennifer Yang, Sahil Shah, Ruby Varmush, Lecia V. Sequist, Shannon L. Stott, Shyamala Maheswaran, Daniel A. Haber, Ravi Kapur and Mehmet Toner, Monolithic Chip for High-throughput Blood Cell Depletion to Sort Rare Circulating Tumor Cells, Scientific Reports, 2017, p. 1-11, 7: 10936.

Gleghorn, Jason P., Erica D. Pratt, Denise Denning, He Liu, Neil H. Bander, Scott T. Tagawa, David M. Nanus, Paraskevi A. Giannakakou and Brian J. Kirby, Capture of circulating tumor cells from whole blood of prostate cancer patients using geometrically enhanced differential immunocapture (GEDI) and a prostate-specific antibody, Lab Chip, 2010, p. 27-29, 10, The Royal Society of Chemistry.

Gupta, Vishal, Insiya Jafferji, Miguel Garza, Vladislava O. Melnikova, David K. Hasegawa, Ronald Pethig and Darren W. Davis, ApoStreamTM, a new dielectrophoretic device for antibody independent isolation and recovery of viable cancer cells from blood, Biomicrofluidics, 2012, p. 024133-1-024133-14, 6, American Institute of Physics.

Harb, Wael, Andrea Fan, Tony Tran, Daniel C. Danila, David Keys, Michael Schwartz and Cristian Ionescu-Zanetti, Mutational Analysis of Circulating Tumor Cells Using a Novel Microfluidic Collection Device and qPCR Assay, Translational Oncology, 2013, p. 528-538, vol. 6, No. 5.

Harouaka, Ramdane A., Ming-Da Zhou, Yin-Ting Yeh, Waleed J. Khan, Avisnata Das, Xin Llu, Christine C. Christ, David T. Dicker, Tara S. Baney, Jussuf T. Kaifi, Chandra P. Belani, Cristina I. Truica, Wafik S. El-Deiry, Jeffrey P. Allerton and Si-Yang Zheng, Flexible Micro Spring Array Device for High-Throughput Enrichment of Viable Circulating Tumor Cells, Molecular Diagnostics and Genetics, 2014, p. 323-333, 60:2, American Association for Clinical Chemistry.

He, Wei, Sumith A. Kularatne, Kimberly R. Kalli, Franklyn G. Prendergast, Robert J. Amato, George G. Klee, Lynn C. Hartmann and Philip S. Low, Quantitation of circulating tumor cells in blood samples from ovarian and prostate cancer patients using tumor-specific fluorescent ligands, Publication of the International Union Against Cancer, 2008, p. 1968-1973, Global Cancer Control.

Hoshino, Kazunori, Yu-Yen Huang, Nancy Lane, Michael Huebschman, Jonathan W. Uhr, Eugene P. Frenkel and Xiaojing Zhang, Microchip-based immunomagnetic detection of circulating tumor cells, Lab Chip, 2011, p. 3449-3457, 11, The Royal Society of Chemistry.

Hou, Han Wei, Majid Ebrahimi Warkiani, Bee Luan Khoo, Zi Rui Li, Ross A. Soo, Daniel Shao-Weng Tan, Wan-Teck Lim, Jongyoon Han, Ali Asgar S. Bhagat and Chwee Teck Lim, Isolation and retrieval of circulating tumor cells using centrifugal forces, Scientific Reports, 2013, p. 1-8, 3: 1259.

Kang, Joo H., Silva Krause, Heather Tobin, Akiko Mammoto, Mathumai Kanapathipillai and Donald E. Ingber, A combined micromagnetic-microfluidic device for rapid capture and culture of rare circulating tumor cells, Lab Chip, 2012, p. 2175-2181, 12, The Royal Society of Chemistry.

Karabacak, Nezihi Murat, Philipp S. Spuhler, Fabio Fachin, Eugene J Lim, Vincent Pai, Emre Ozkumur, Joseph M. Martel, Nikola Kojic, Kyle Smith, Pin-i Chen, Jennifer Yang, Henry Hwang, Bailey Morgan, Julie Trautwein, Thomas A Barber, Shannon L Stott, Shyamala, Maheswaran, Ravi Kapur, Daniel A Haber and Mehmet Toner, Micro-fluidic, marker-free isolation of circulating tumor cells from blood samples, Nature Protocols, 2014, p. 694-710, vol. 9, No. 3, Nature American, Inc.

(56) References Cited

OTHER PUBLICATIONS

Lara, Oscar, Xiaodong Tong, Maciej Zborowski and Jeffrey J. Chalmers, Enrichment of rare cancer cells through depletion of normal cells using density and flow-through, immunomagnetic cell separation, International Society for Experimental Hematology, 2004, p. 891-904, 32, Elsevier Inc.

Li, Peng, Zhangming Mao, Zhangli Peng, Lanlan Zhou, Yuchao Chen, Po-Hsun Huang, Cristina I. Truica, Joseph J. Drabick, Wafik S. El-Deiry, Ming Dao, Subra Suresh and Tony Jun Huang, Accoustic separation of circulating tumor cells, Proceedings of the National Academy of Sciences of the United States of America, 2015, p. 4970-4975, vol. 112, No. 16.

Liu, Zhian, Alberto Fusi, Eva Klopocki, Alexander Schmittel, Ingeborg Tinhofer, Anika Nonnemacher and Ulrich Keilholz, Negative enrichment by immunomagnetic nanobeads for unbiased characterization of circulating tumor cells from peripheral blood of cancer patients, Journal of Translational Medicine, 2011, p. 1-8, 9:70 BioMed Central.

Lu, Yi-Tsung, Libo Zhao, Qinglin Shen, Mitch A. Garcia, Dongxia Wu, Shuang Hou, Min Song, Xiaochun Xu, Wei-Han Ouyang, William W.-L. Ouyang, Jake Lichterman, Zheng Luo, Xuan Xuan, Jiaoti Huang, Leland W.K. Chung, Matthew Rettig, Hsian-Rong Tseng, Chen Shao and Edwin M. Posadas, Nano-Velcro Chip for CTC enumeration in prostate cancer patients, National Institutes of Health, 2013, p. 1-20, 64(2).

Mikolajczyk, Stephen D., Lisa S. Millar, Pavel Tsinberg, Stephen M. Coutts, Maryam Zomorrodi, Tam Pham, Farideh Z. Bischoff and Tony J. Pircher, Detection of EpCAM-Negative and Cytokeratin-Negative Circulating Tumor Cells in Peripheral Blood, Journal of Oncology, 2011, p. 1-10, vol. 2011, Hindawi Publishing Corporation.

Weitz, Jurgen, Peter Kienle, Jeannine Lacroix, Frank Willeke, Axel Benner, Thomas Lehnert, Christian Herfarth and Magnus von Knebel Doeberitz, Dissemination of Tumor Cells in Patients Undergoing Surgery for Colorectal Cancer, Clinical Cancer Research, 1998, p. 343-348, vol. 4, American Association for Cancer Research Journals.

Yoon, Hyeun Joong, Tae Hyun Kim, Zhuo Zhang, Ebrahim Azizi, Trinh M. Pham, Costanza Paoletti, Jules Lin, Nithya Ramnath, Max S. Wicha, Daniel F. Hayes, Diane M. Simeone and Sunitha Nagrath, Sensitive capture of circulating tumor cells by functionalized graphene oxide nanosheets, Nature Nanotechnology, 2013, p. 735-741, vol. 8, Macmillian Publishers Limited.

Zhao, Wujun, Rui Cheng, Brittany D. Jenkins, Taotao Zhu, Nneoma E. Okonkwo, Courtney E. Jones, Melissa B. Davis, Sravan K. Kavuri, Zhonglin Hao, Carsten Schroeder and Leidong Mao, Label-free ferrohydrodynamic cell separation of circulating tumor cells, Lab Chip, 2017, p. 3097-3111, 17, The Royal Society of Chemistry.

Zhao, Wujun, Rui Cheng, So Hyun Lim, Joshua R. Miller, Weizhong Zhang, Wei Tang, Jin Xie and Leidong Mao, Biocompatible and label-free separation of cancer cells from cell culture lines from white blood cells in ferrofluids, Lab Chip, 2017, p. 2243-2255, 17, The Royal Society of Chemistry.

Zhou, Ming-Da, Sijie Hao, Anthony J. Williams, Ramdane A. Harouaka, Brett Schrand, Siddarth Rawal, Zheng Ao, Randall Brennenman, Eli Gilboa, Bo Lu, Shuwen Wang, Jiyue Zhu, Ram Datar, Richard Cote, Yu-Chong Tai and Si-Yang Zheng, Separable Bilayer Microfiltration Device for Viable Label-free Enrichment of Circulating Tumour Cells, Scientific Reports, 2014, p. 1-10, 4: 7392.

European Search Report dated Jul. 8, 2021 in co-pending European Patent Application No. 18 84 1411 filed Aug. 4, 2018.

International Search Report dated Oct. 18, 2018 in PCT Patent Application No. PCT/US2018/045294.

Nagrath, Sunitha, Lecia V. Sequist, Shyamala Maheswaren, Daphne W. Bell, Daniel Irimia, Lindsey Ulkus, Matthew R. Smith, Eunice L. Kwak, Subba Digumarthy, Alona Muzikansky, Paula Ryan, Ulysses J. Balis, Ronald G. Tompkins, Daniel A. Haber and Mehmet Toner, Isolation of rare circulating tumor cells in cancer patients by microchip technology, Nature, 2007, p. 1235-1241, vol. 450:20/27, Nature Publishing Group.

Qin, Xi, Sungyoung Park, Simon P. Duffy, Kerryn Matthews, Richard R. Ang, Tilman Todenhofer, Hamid Abdi, Arun Azad, Jenny Bazov, Kim N. Chi, Peter C. Black and Hongshen MA, Size and deformability based separation of circulating tumor cells from castrate resistant prostate cancer patients using resettable cell traps, Lab Chip, 2015, p. 2278-2286, 15, The Royal Society of Chemistry.

Riethdorf, Sabine, Herbert Fritsche, Volkmar Muller, Thomas Rau, Christian Schindlbeck, Bridgette Rack, Wolfgang Janni, Cornelia Coith, Katrin Beck, Fritz Janicke, Summer Jackson, Terrie Gornet, Massimo Cristofanilli and Klaus Pantel, Detection of Circulating Tumor Cells in Peripheral Blood of Patients with Metastatic Breast Cancer: A Validation Study of the CellSearch System, Clinical Cancer Research, 2007, p. 920-928, 13, American Association for Cancer Research Journals.

Sarioglu, A. Fatih, Nicola Aceto, Nikola Kojic, Maria C. Donaldson, Mahnaz Zeinali, Bashar Hamza, Amanda Engstrom, Huili Zhu, Tilak K. Sundaresan, David T. Miyamoto, Xi Luo, Aditya Bardia. Ben S. Wittner, Sridhar Ramaswamy, Toshi Shioda, David T. Ting, Shannon L. Stott, Ravi Kapur, Shyamala Maheswaren, Daniel A. Haber and Mehmet Toner, A microfluidic device for label-free, physical capture of circulating tumor cell clusters, Nature Methods, 2015, p. 685-694, vol. 12, No. 7, Nature American, Inc.

Sheng, Weian, Olorunseun O. Ogunwobi, Tao Chen, Jinling Zhang, Thomas J. George, Chen Liu and Z. Hugh Fan, Capture, release and culture of circulating tumor cells from pancreatic cancer patients using an enhanced mixing chip, Lap Chip, 2014, p. 89-98, 14, The Royal Society of Chemistry.

Sollier, Elodie, Derek E. Go, James Che, Daniel R. Gossett, Sean O'Byrne, Westbrook M. Weaver, Nicolas Kummer, Matthew Rettig, Jonathan Goldman, Nicholas Nickols, Susan McCloskey, Rajan P. Kulkarni and Dino Di Carlo, Size-selection collection of circulating tumor cells using Vortex technology, Lab Chip, 2014, p. 63-77, 14, The Royal Society of Chemistry.

Talasaz, AmirAli H., Ashley A. Powell, David E. Huber, James G. Berbee, Kyung-Ho Koh, Wong Yu, Wenzhong Xiao, Mark M. Davis, R. Fabian Pease, Michael N. Mindrinos, Stefanie S. Jeffrey and Ronald W. Davis, Isolating highly enriched populations of circulating epithelial cells and other rare cells from blood using a magnetic sweeper device, Proceedings of the National Academy of Sciences of the United States of America, 2008, p. 3970-3975, vol. 106, No 10.

Tang, Man, Cong-Ying Wen, Ling-Ling Wu, Shao-Li Hong, Jiao Hu, Chun-Miao Xu, Dai-Wen Pang and Zhi-Ling Zhang, A chip assisted immunomagnetic separation system for the efficient capture and in situ identification of circulating tumor cells. Lab Chip, 2016, p. 1214-1223, 16, The Royal Society of Chemistry.

Vona, Giovanna, Abdelmajid Sabile, Malek Louha, Veronique Sitruk, Serge Romana, Karin Schutze, Frederique Capron, Dominique Franco, Mario Pazzagli, Michel Vekemans, Bernard Lacour, Christian Brechot and Patrizia Paterlini-Brechot, Isolation by Size of Epithelial Tumor Cells: A New Method for the Immunomorphological and Molecular Characterization of Circulating Tumor Cells, American Journal of Pathology, 2000, p. 57-63, vol. 156, No. 1, American Society for Investigative Pathology.

* cited by examiner

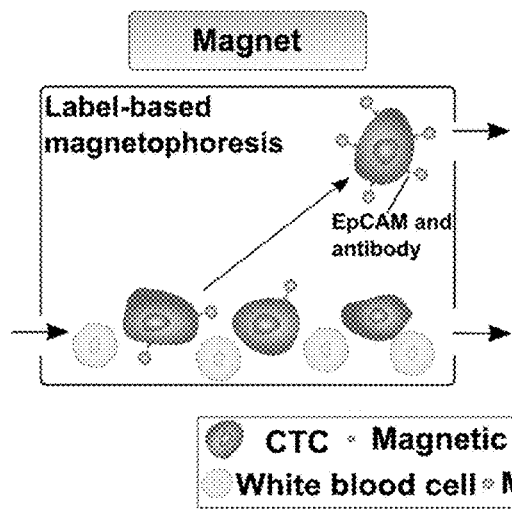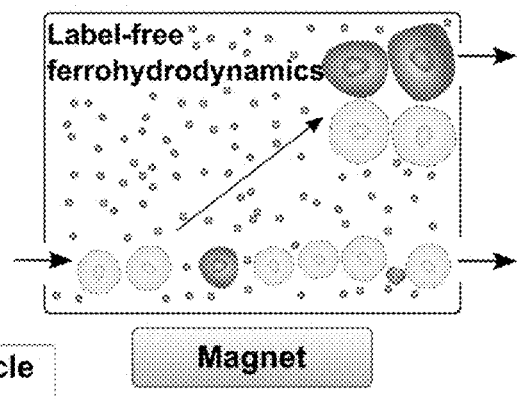
FIG. 1.1A    FIG. 1.1B
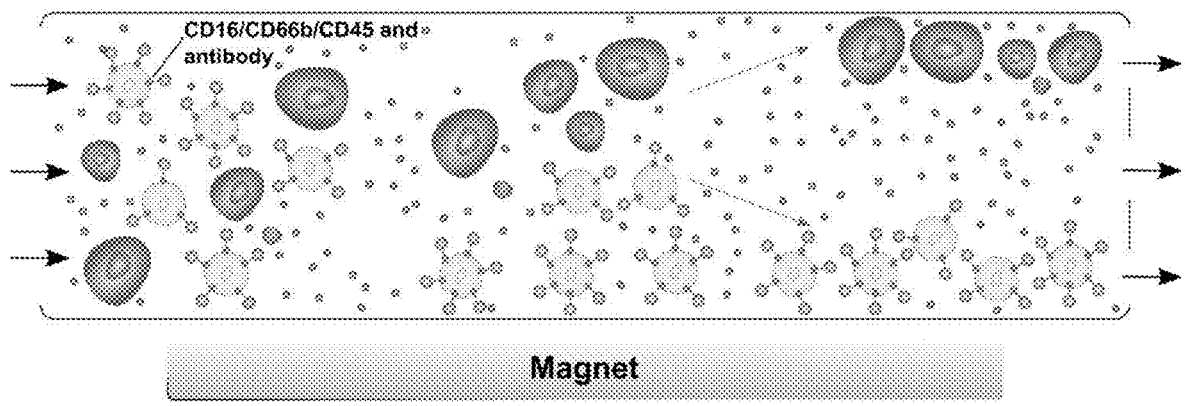
FIG. 1.1C

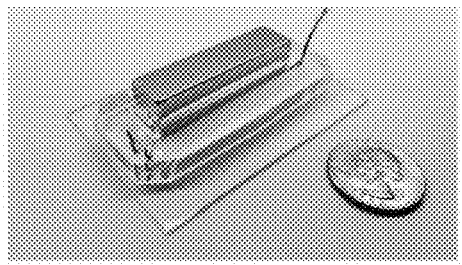
FIG. 1.1D
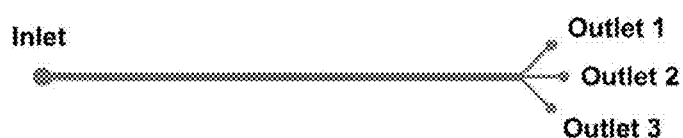
FIG. 1.1E
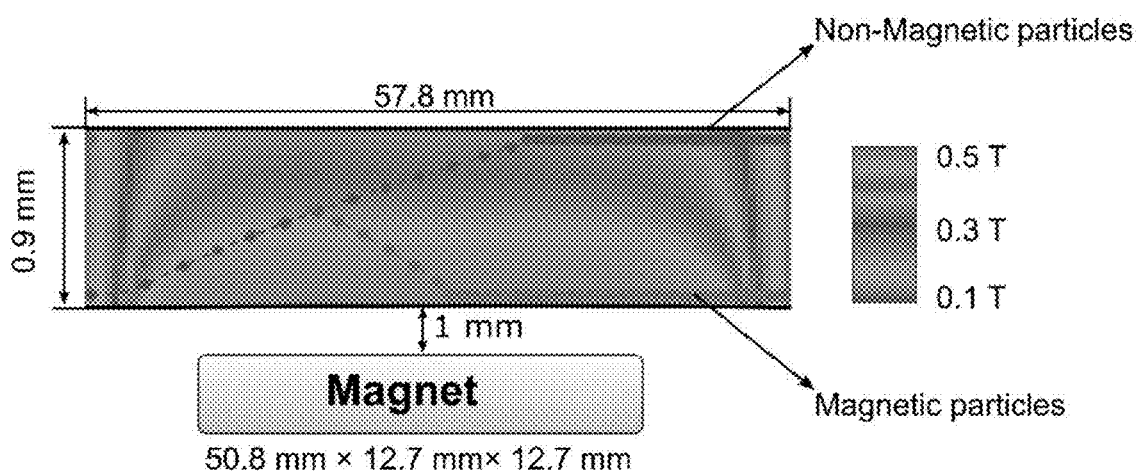
FIG. 1.1F

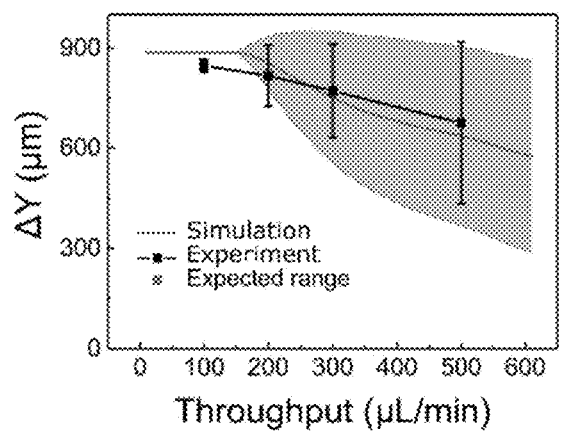
FIG. 1.2A
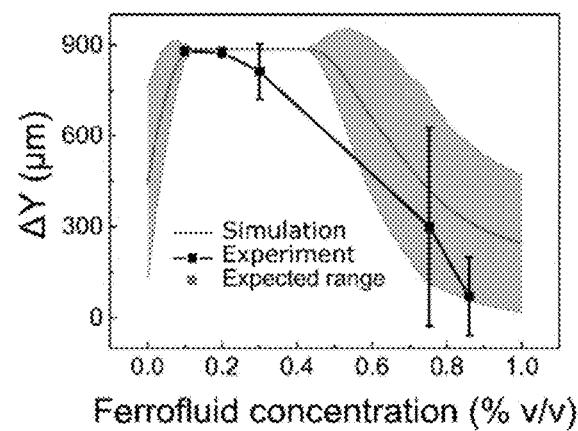
FIG. 1.2B
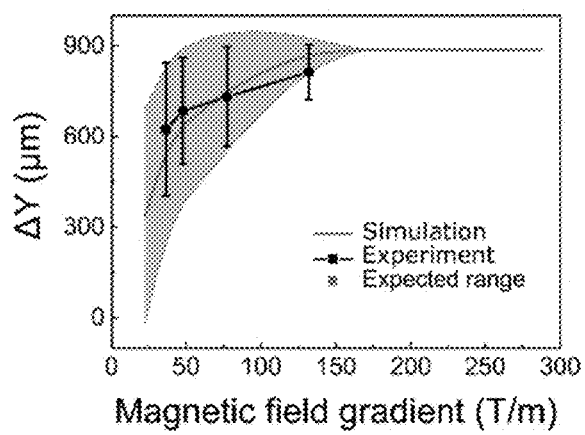
FIG. 1.2C
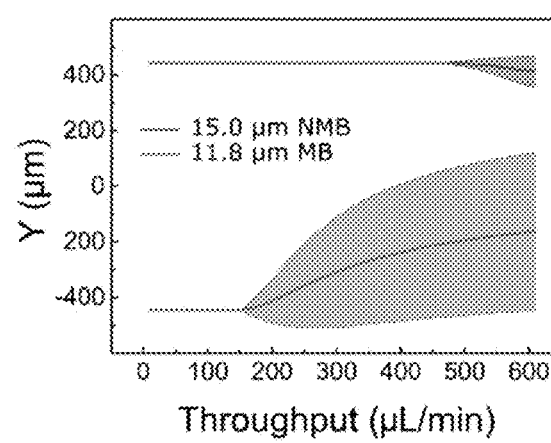
FIG. 1.2D

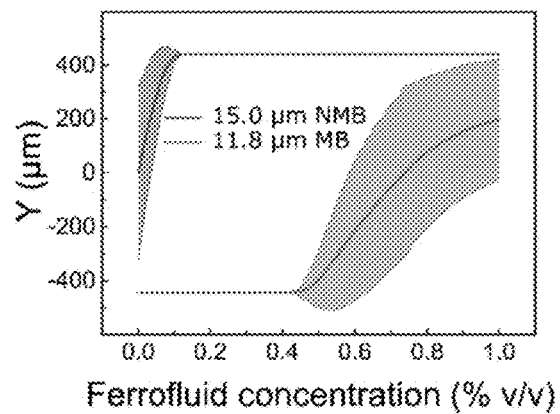
FIG. 1.2E
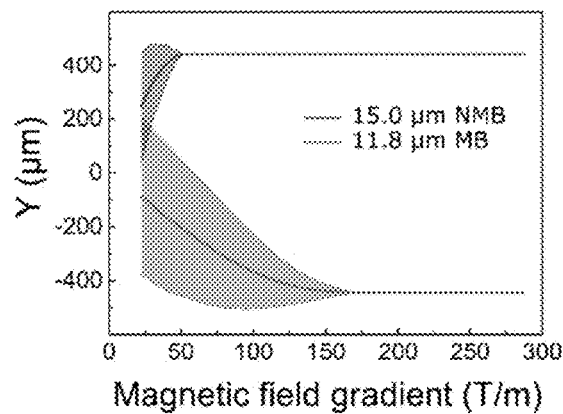
FIG. 1.2F
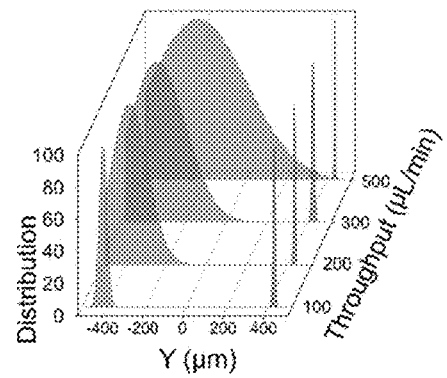
FIG. 1.2G
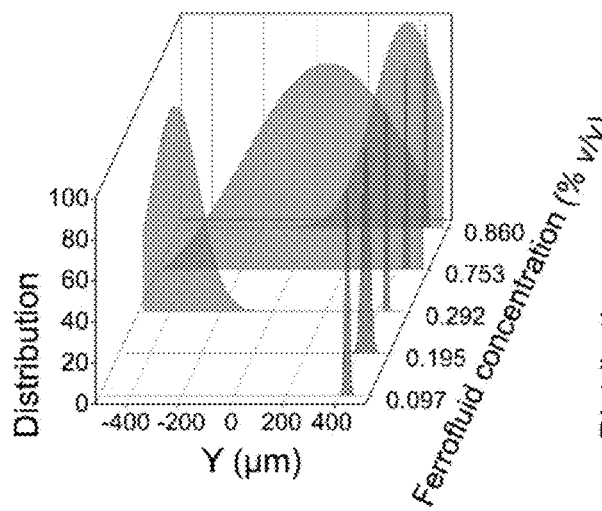
FIG. 1.2H
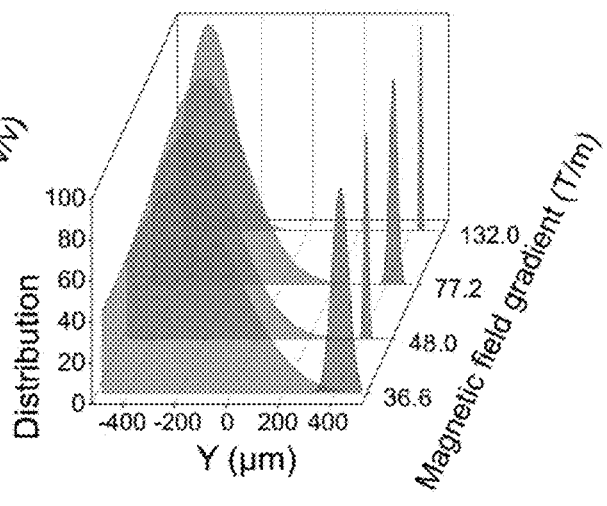
FIG. 1.2I

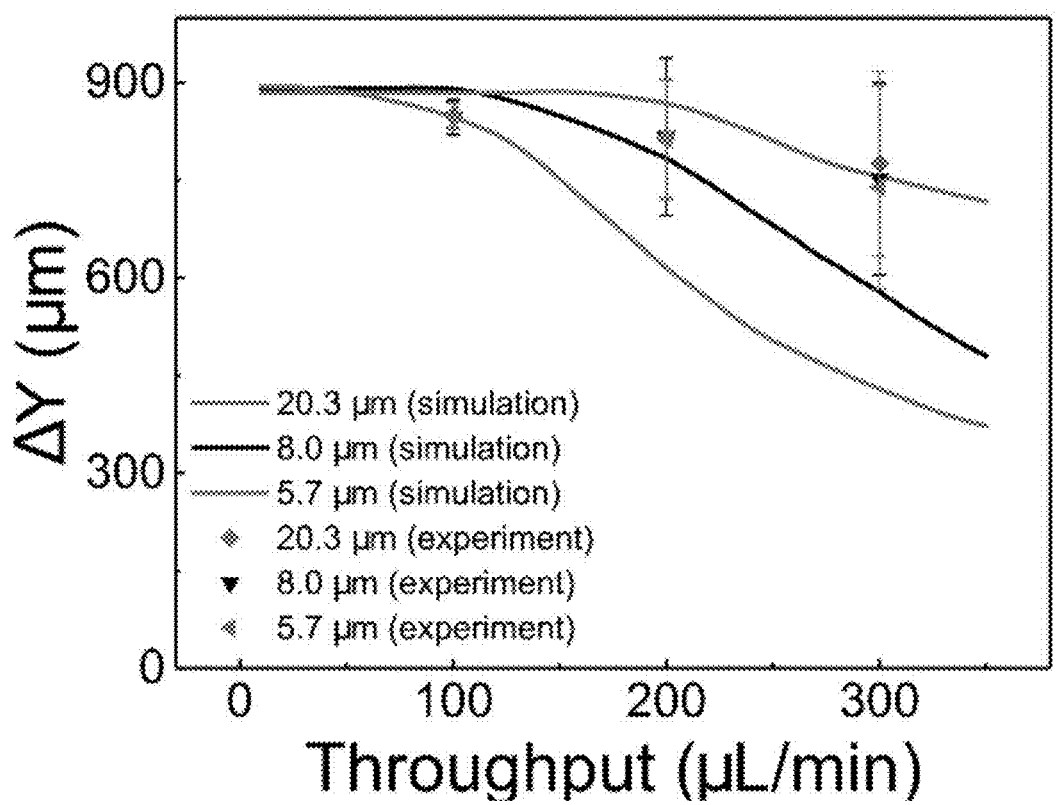
FIG. 1.3A
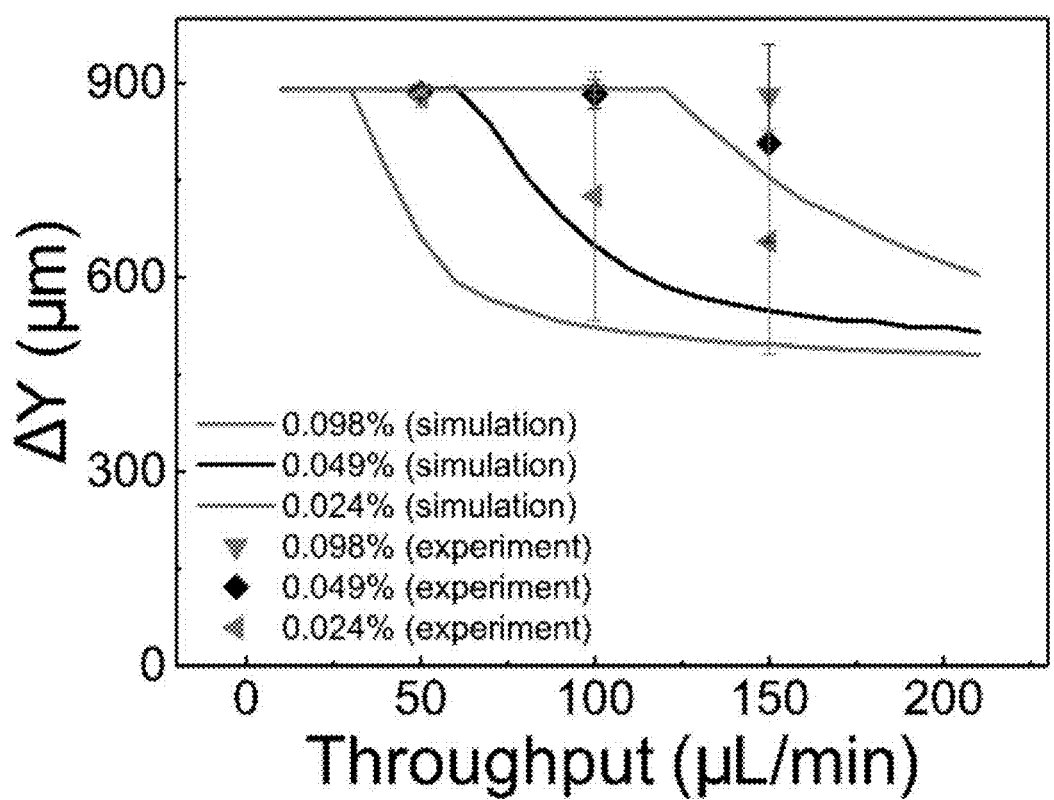
FIG. 1.3B

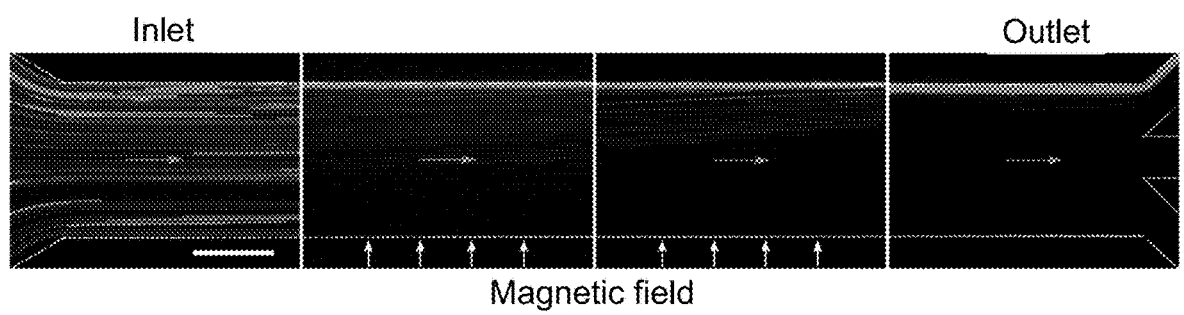
FIG. 1.3C
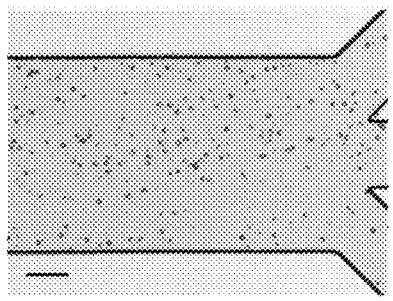 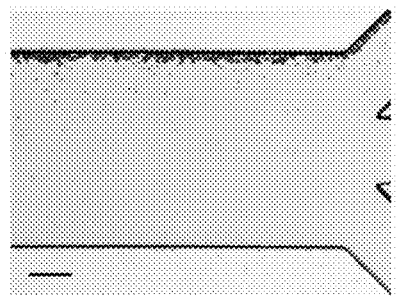 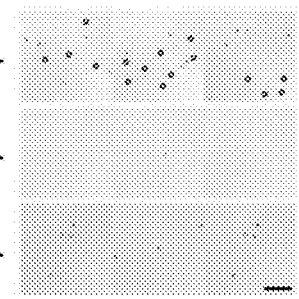
FIG. 1.3D  FIG. 1.3E  FIG. 1.3F

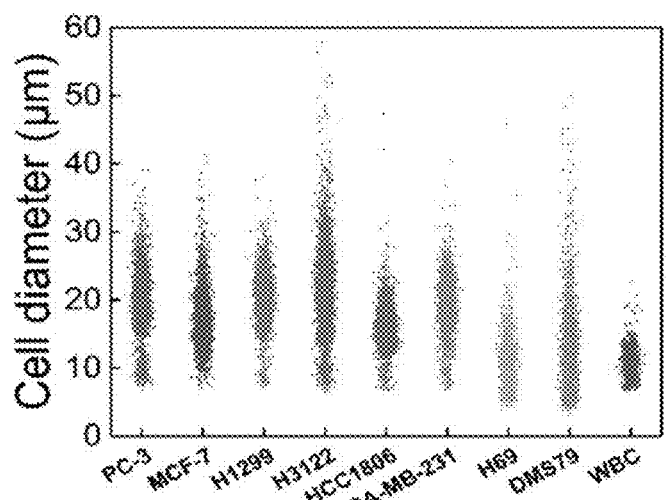
FIG. 1.4A
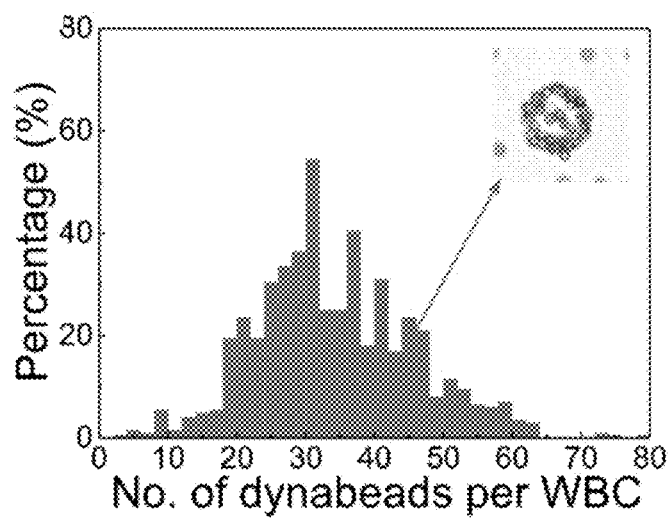
FIG. 1.4B
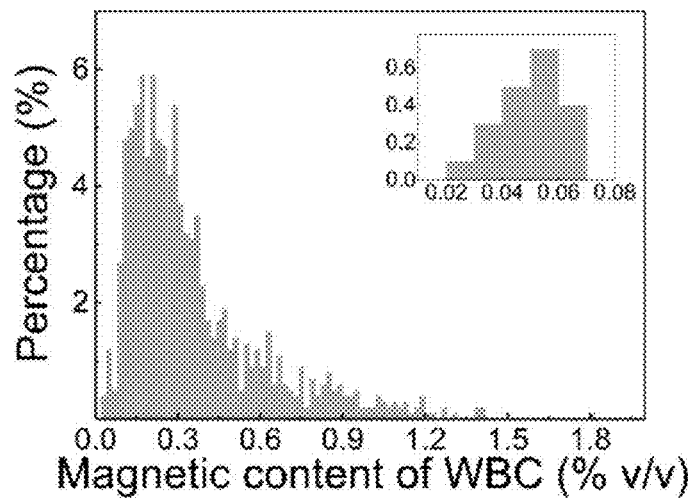
FIG. 1.4C

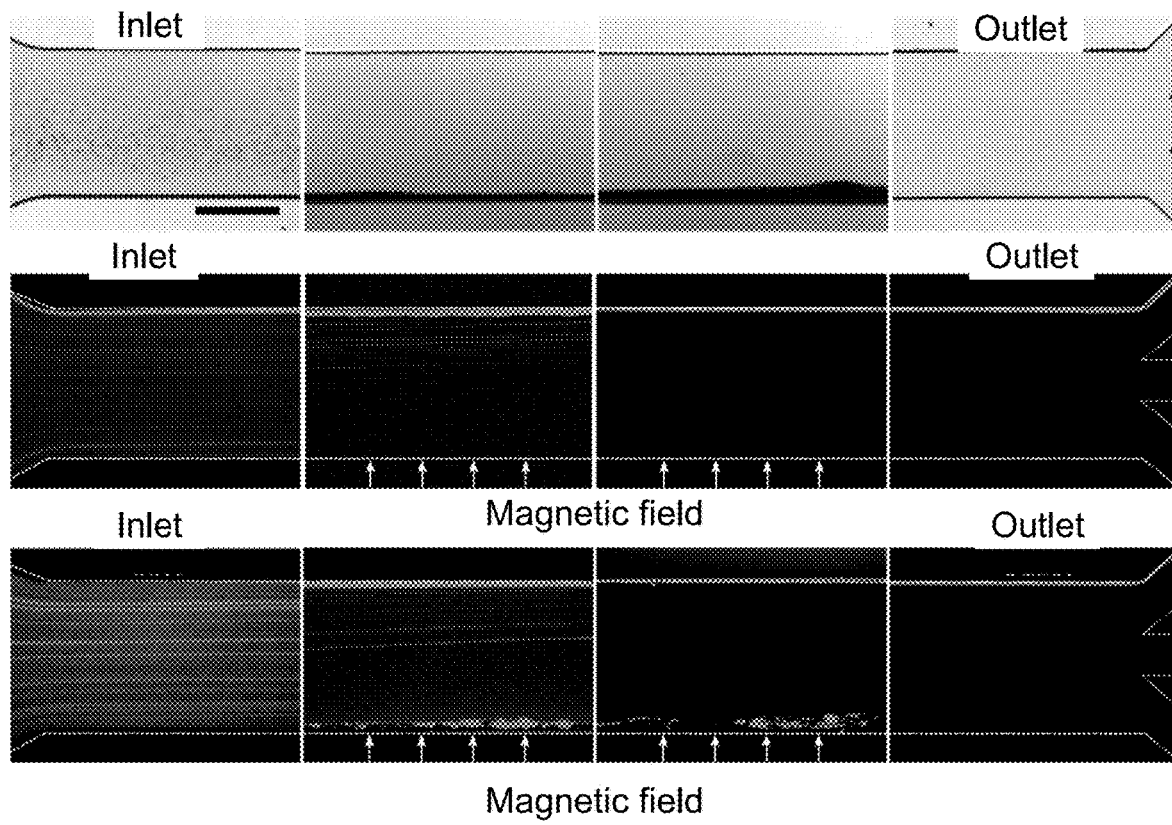
*FIG. 1.5A*
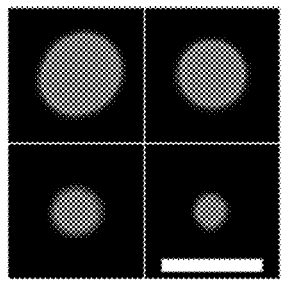
*FIG. 1.5B*
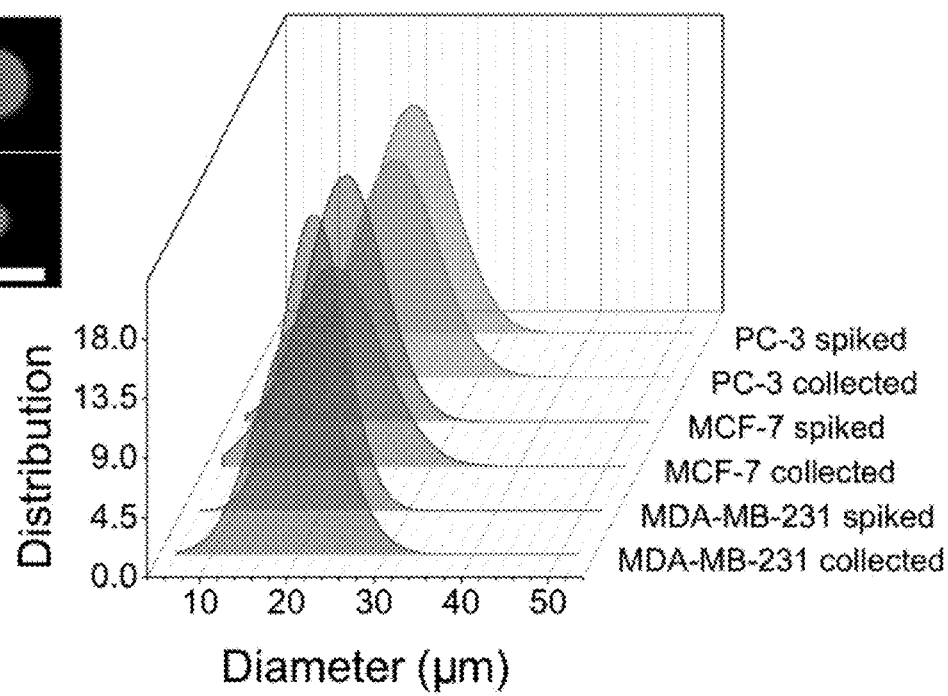
*FIG. 1.5C*

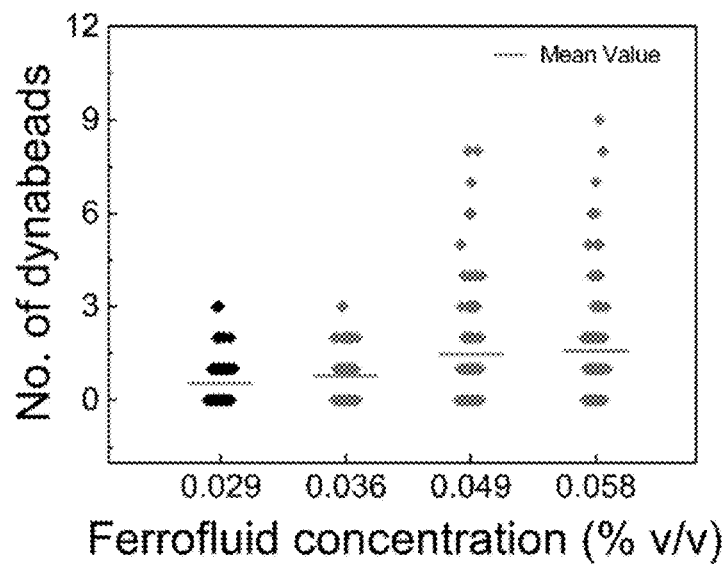
FIG. 1.5D
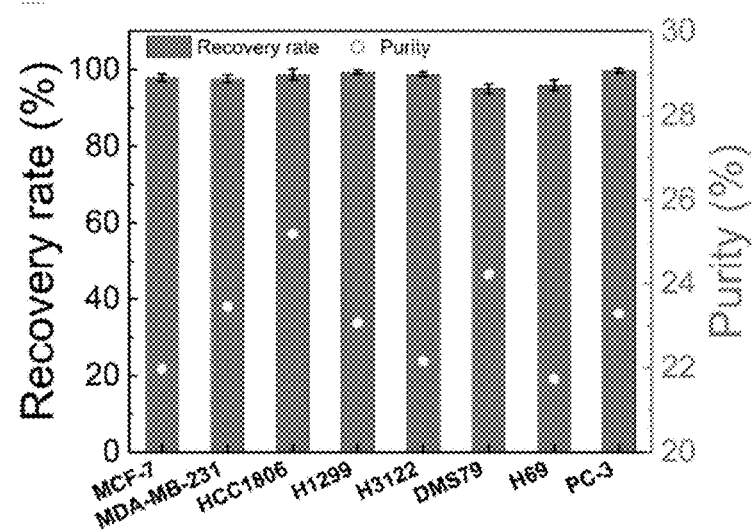
FIG. 1.5E
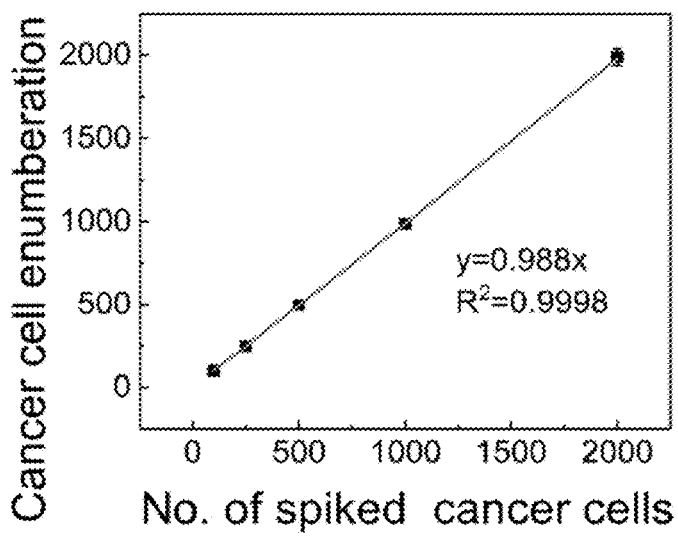
FIG. 1.5F

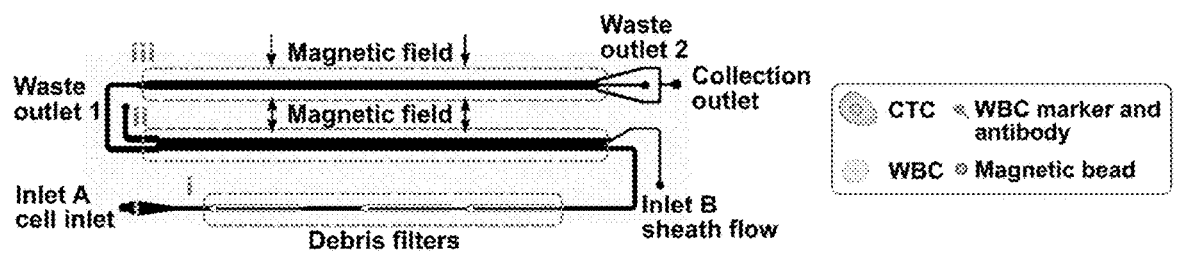
FIG. 1.6A
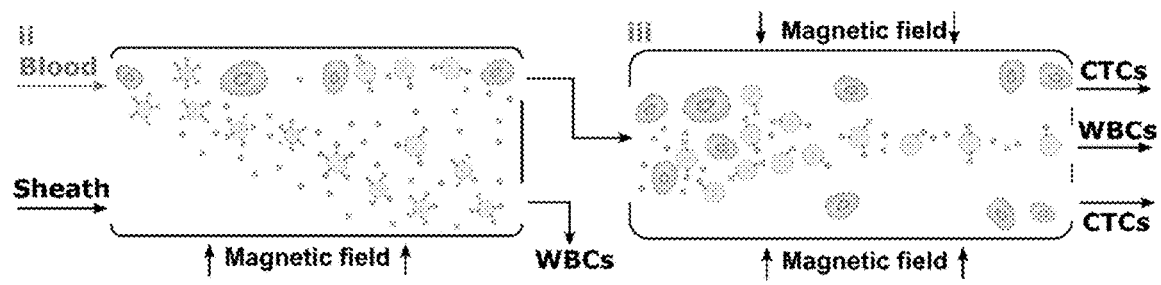
FIG. 1.6B
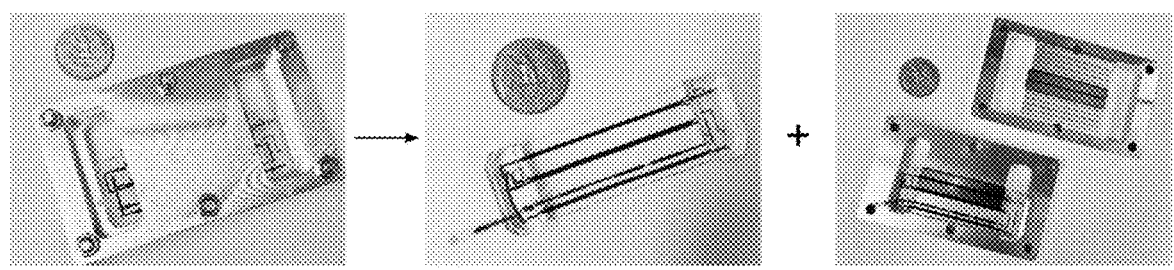
FIG. 1.6C

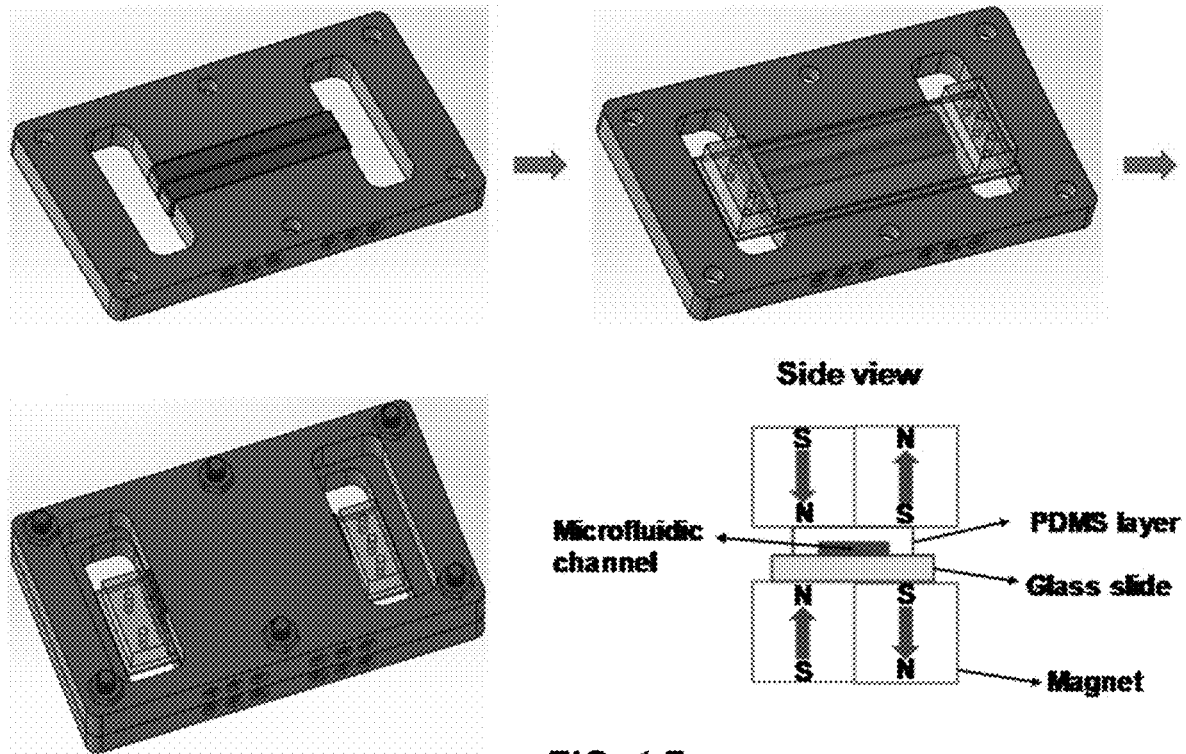
FIG. 1.7
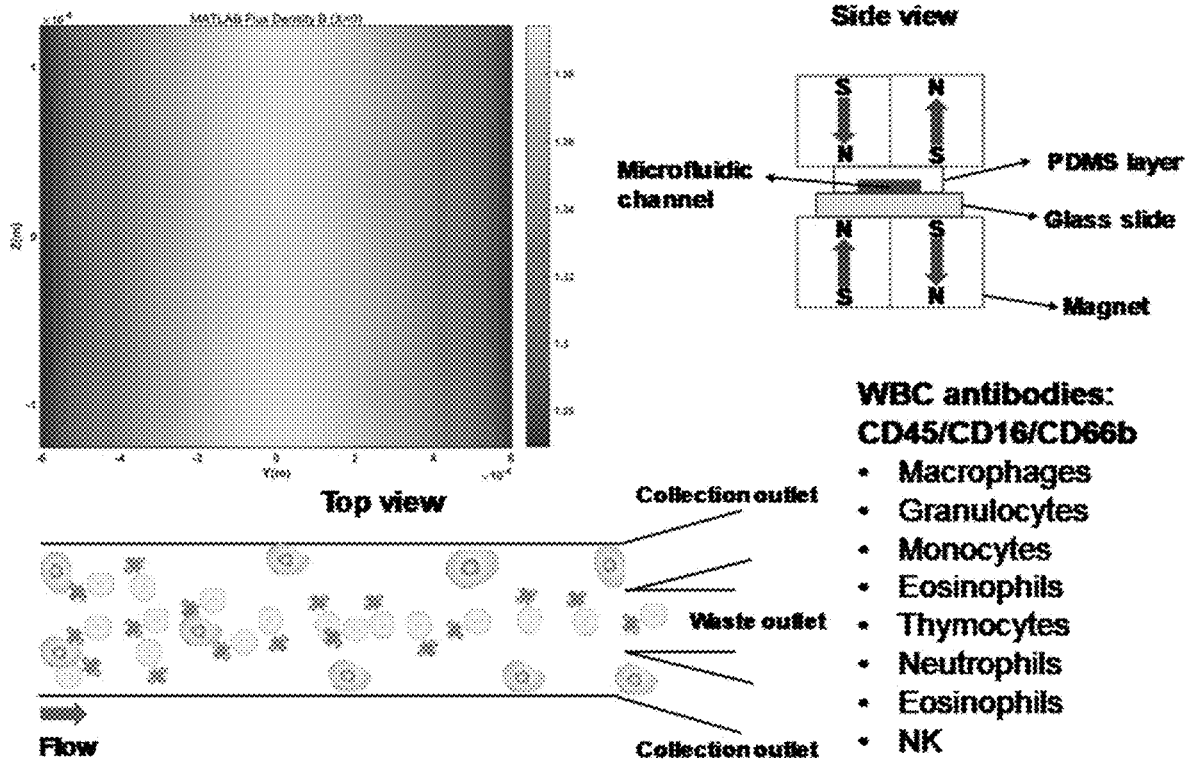
FIG. 1.8

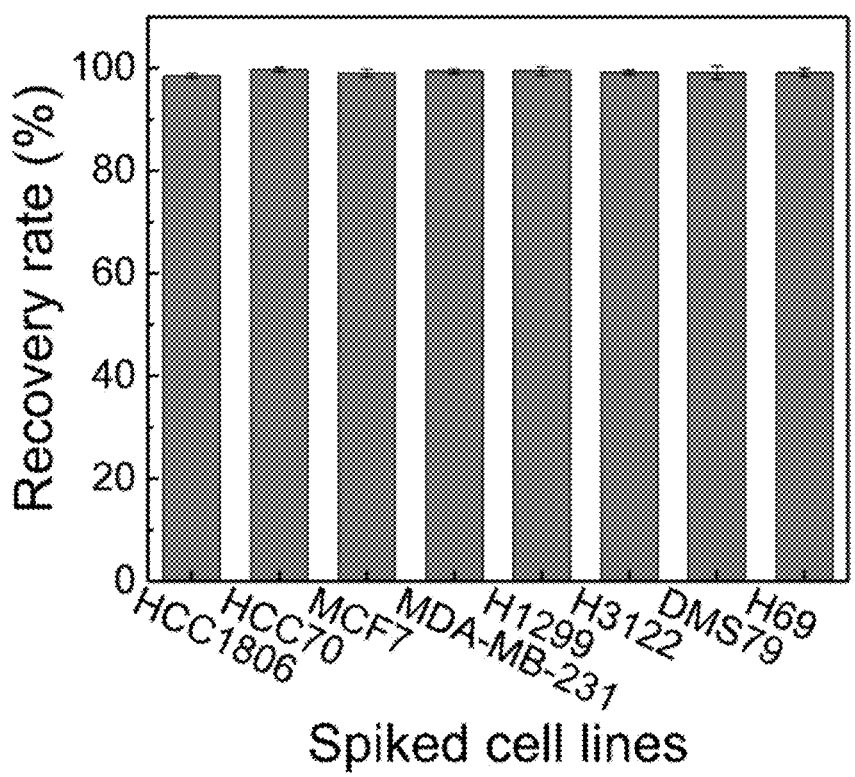
FIG. 1.9A
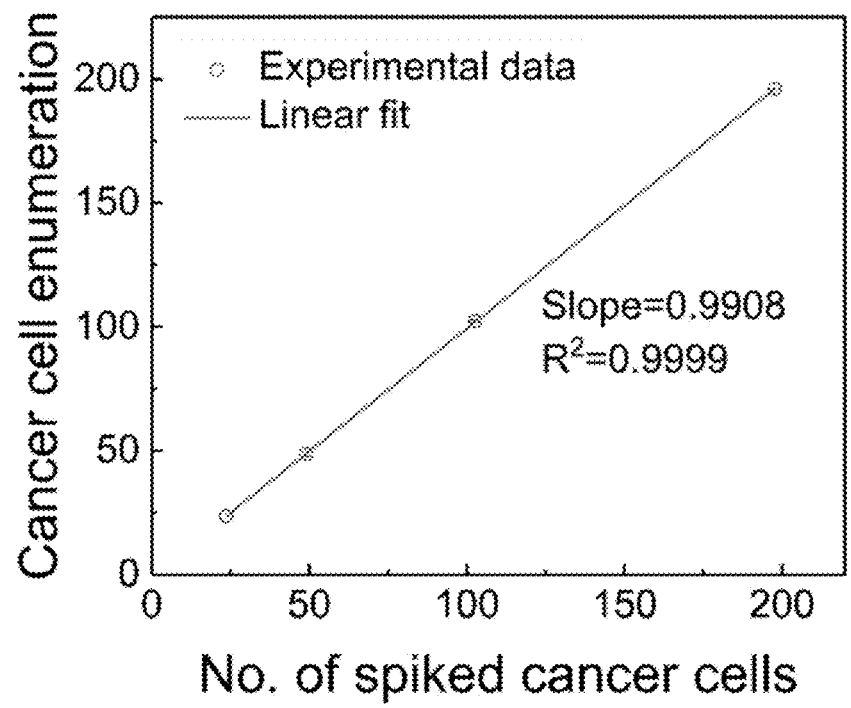
FIG. 1.9B

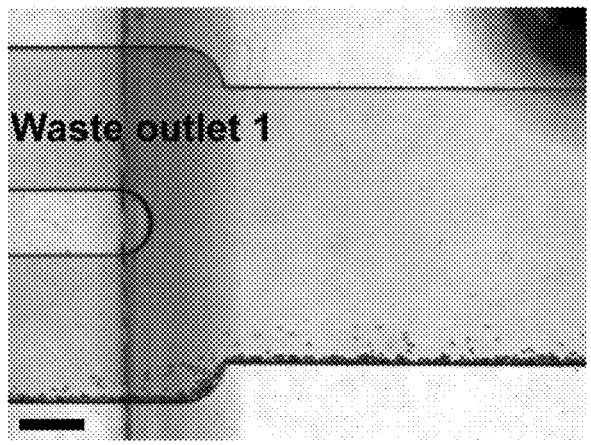
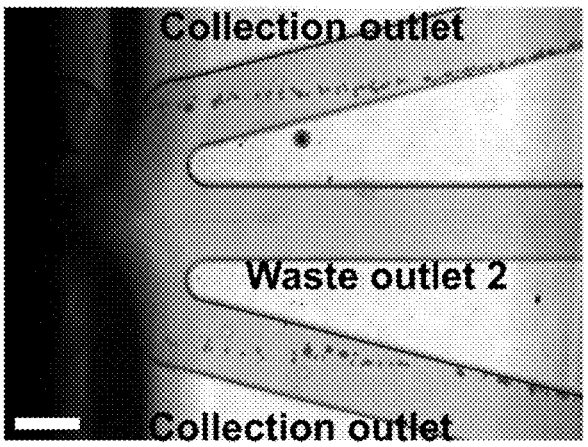
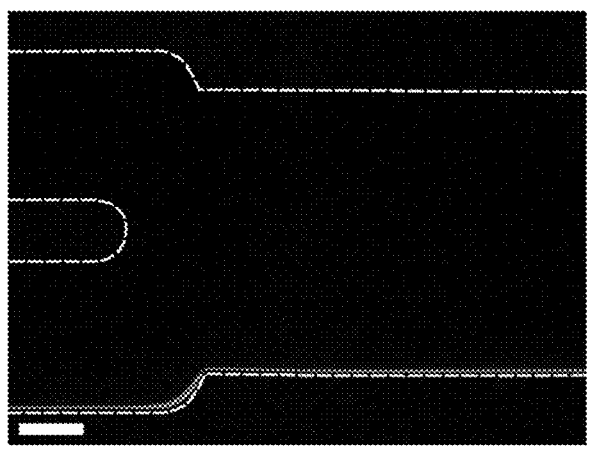
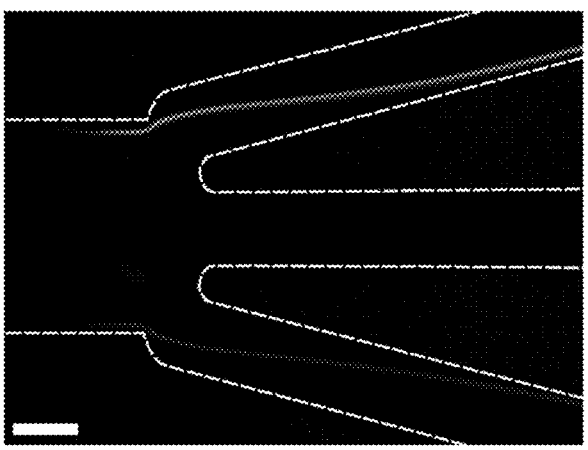
*FIG. 1.10A*          *FIG. 1.10B*

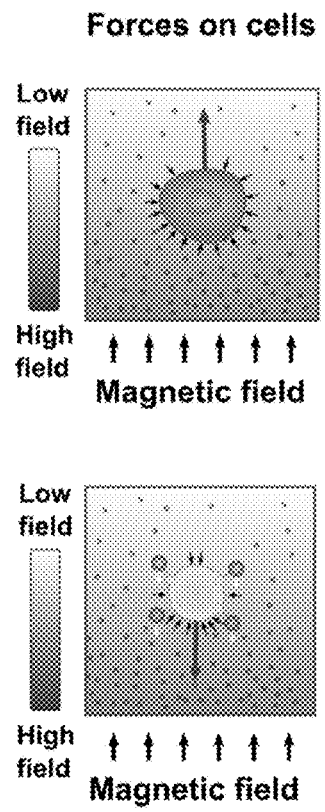
*FIG. 2.1A*
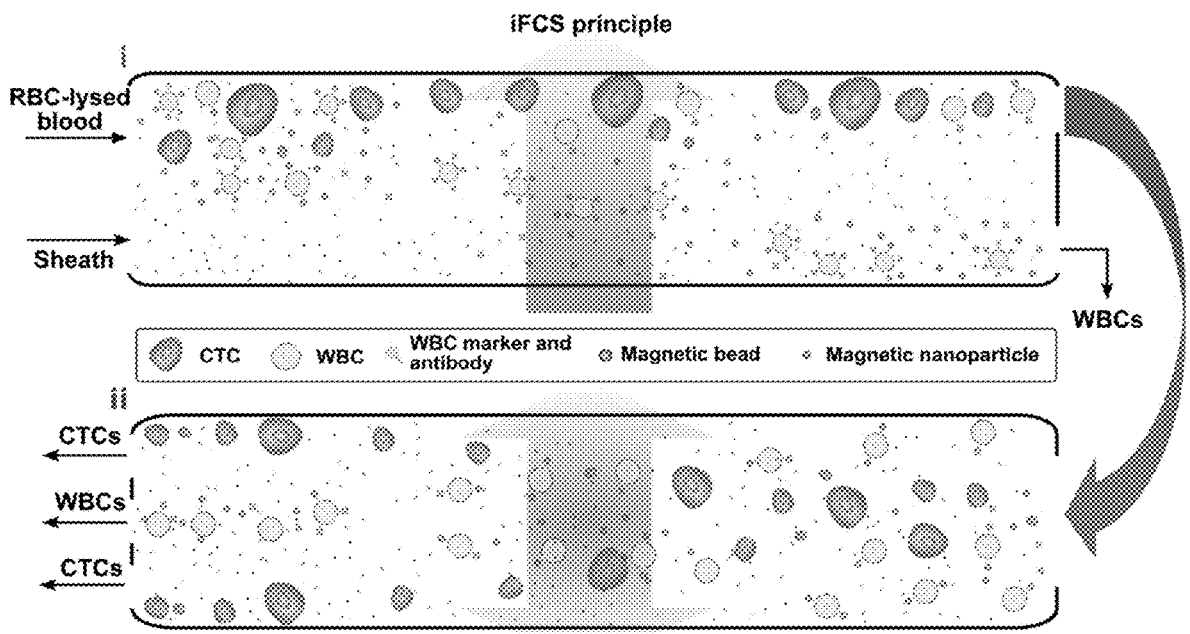
*FIG. 2.1B*

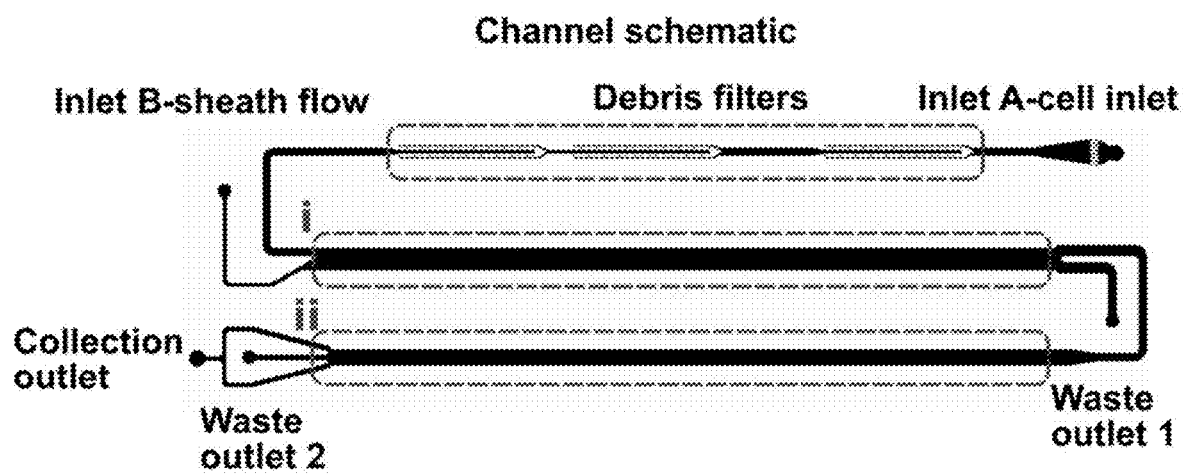
FIG. 2.1C
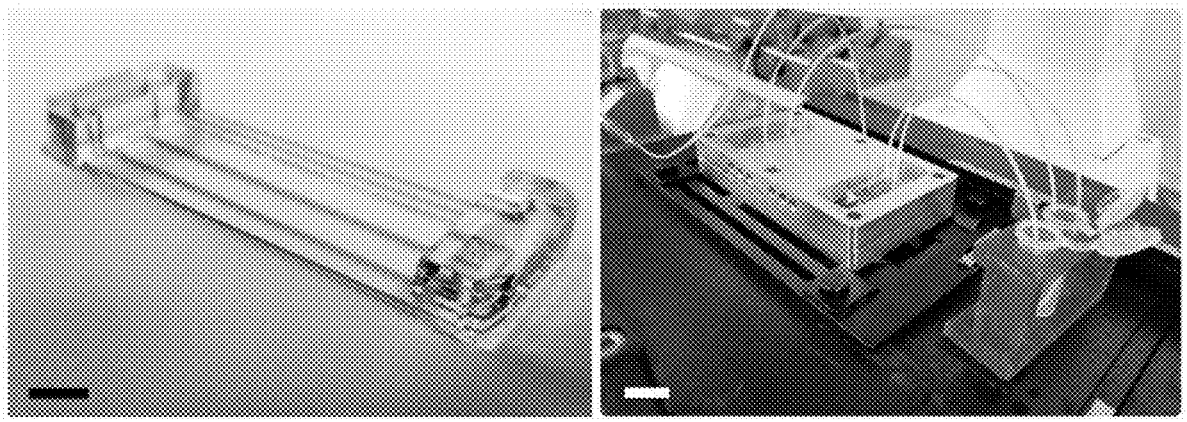
FIG. 2.1D

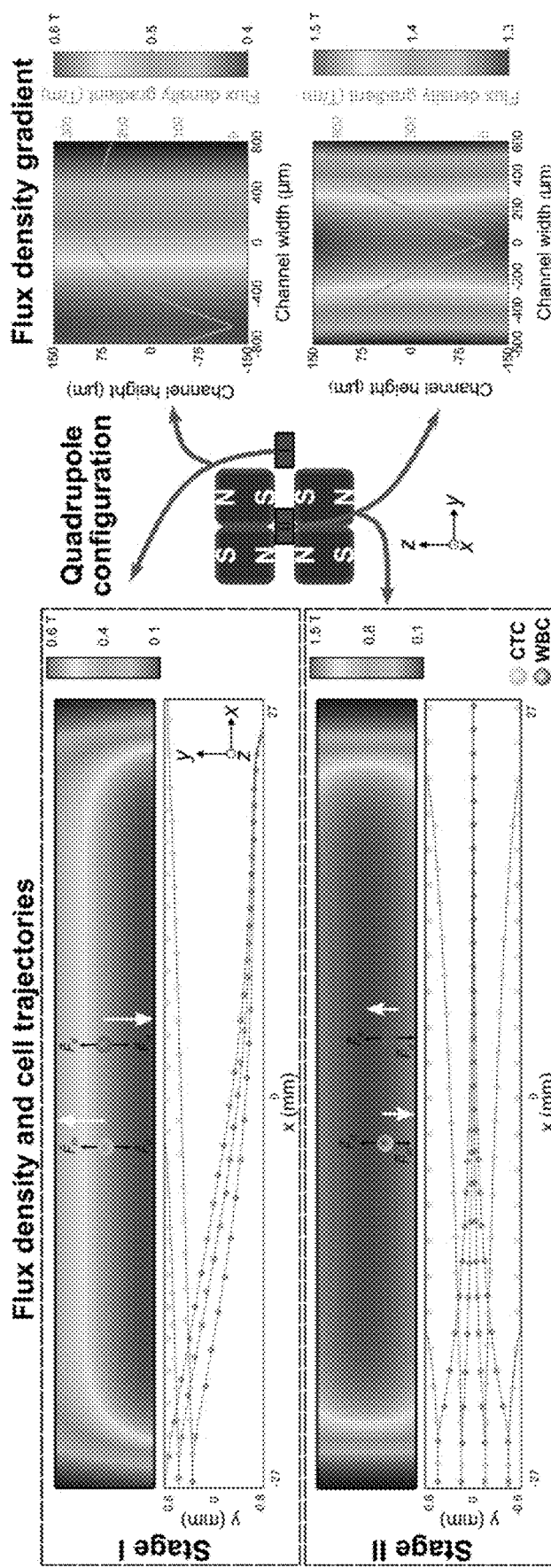
FIG. 2.2A

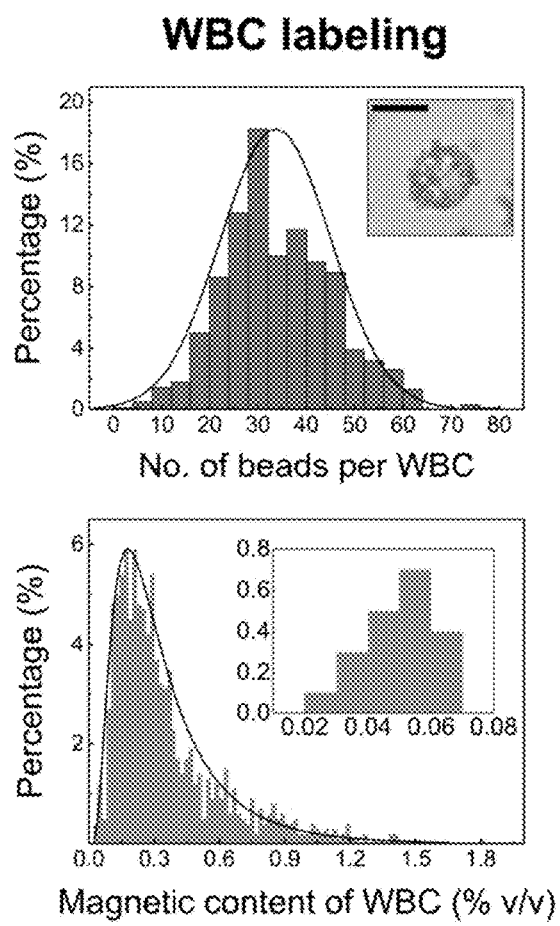
*FIG. 2.2B*
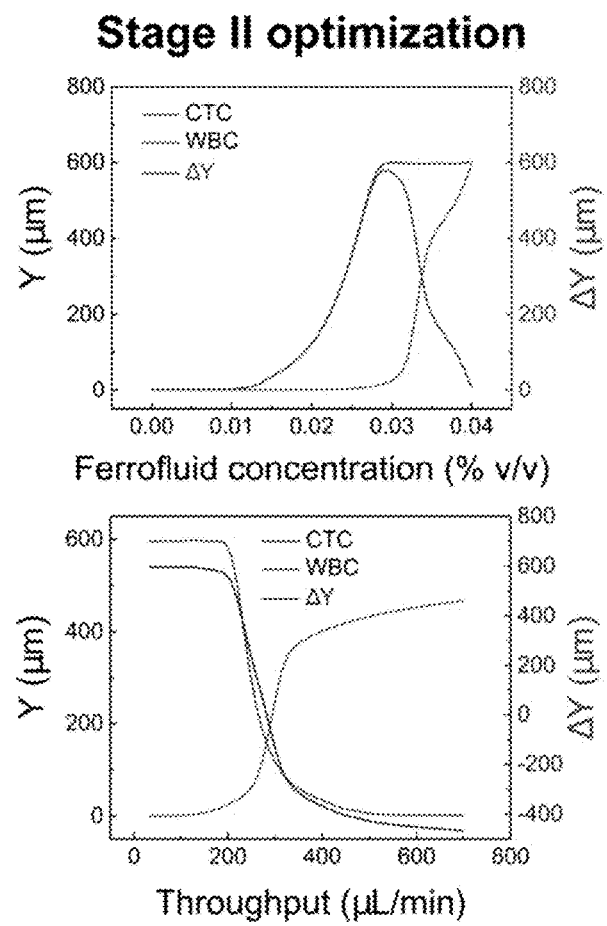
*FIG. 2.2C*

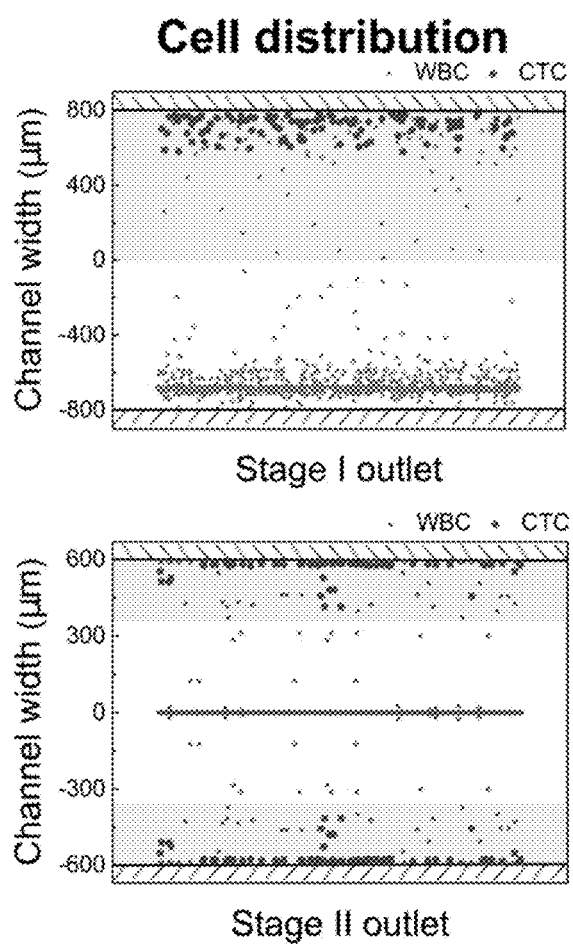
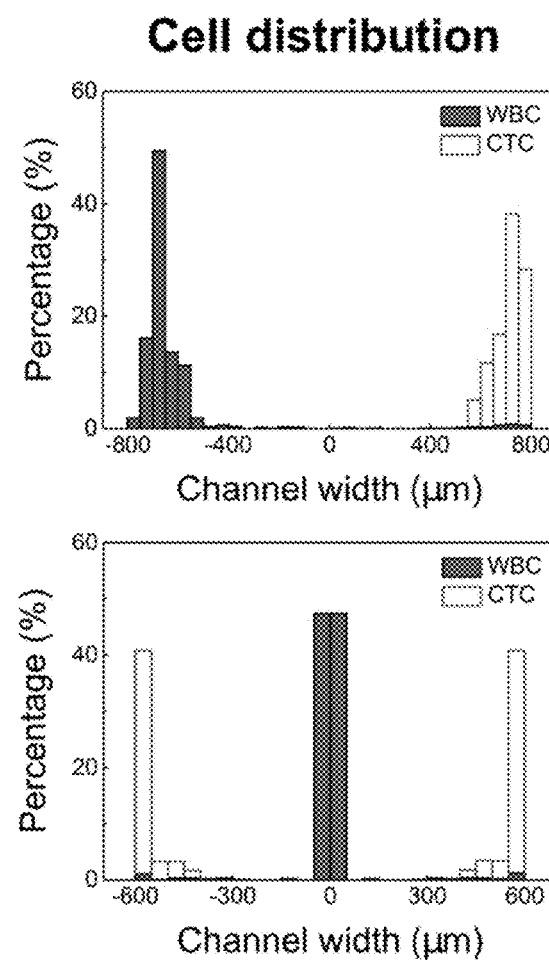
FIG. 2.2D
FIG. 2.2E

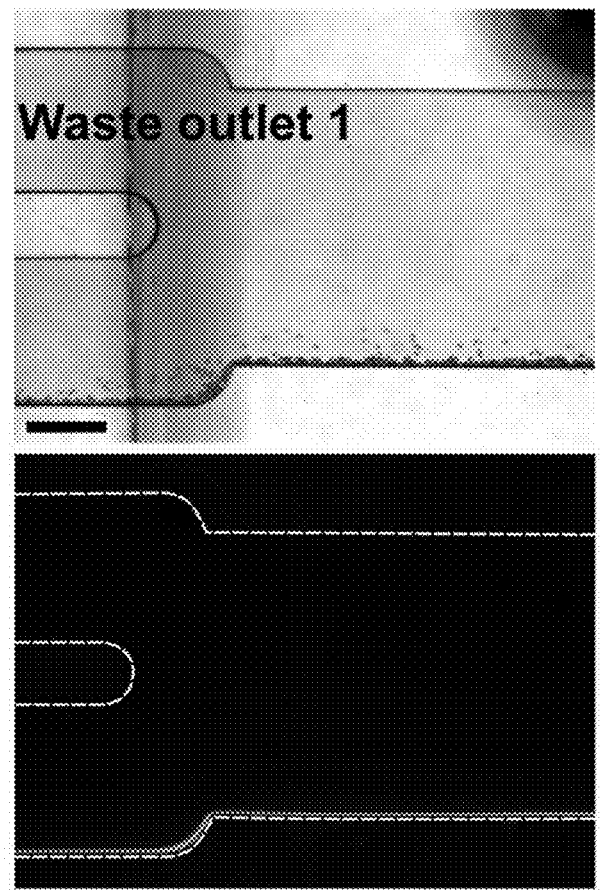 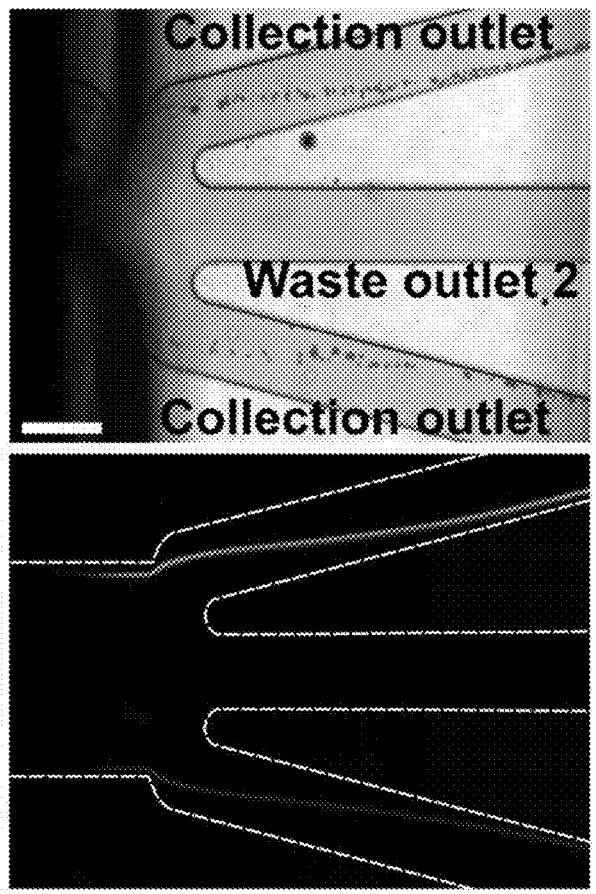
FIG. 2.3A    FIG. 2.3B

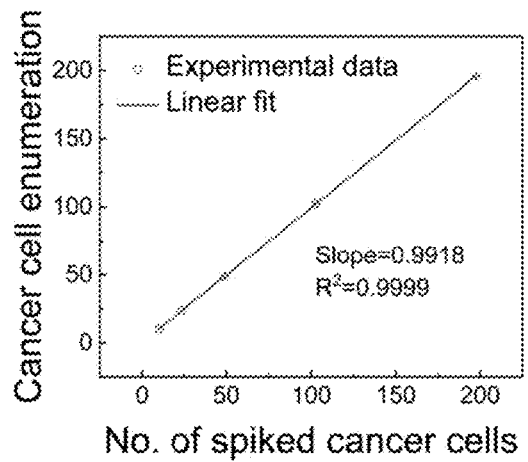
*FIG. 2.3C*
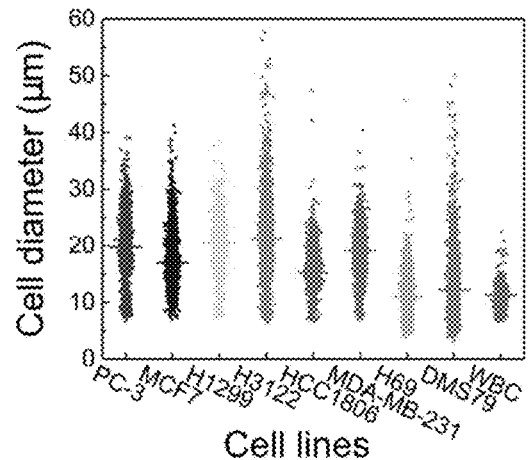
*FIG. 2.3D*
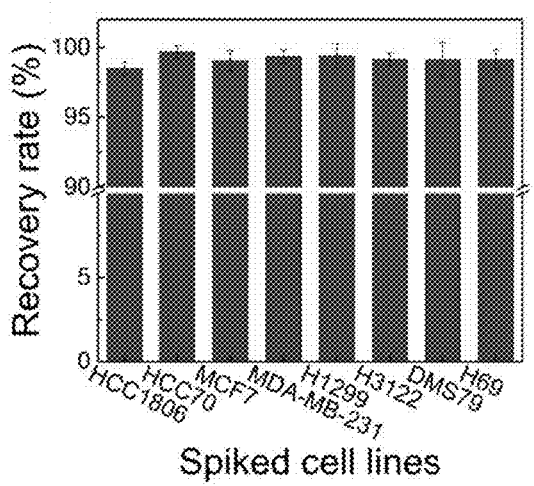
*FIG. 2.3E*
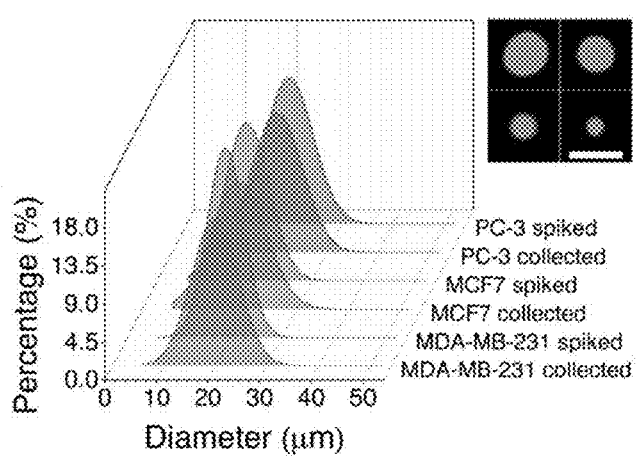
*FIG. 2.3F*

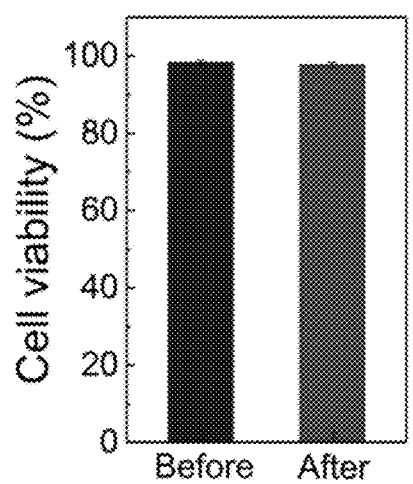
*FIG. 2.3G*
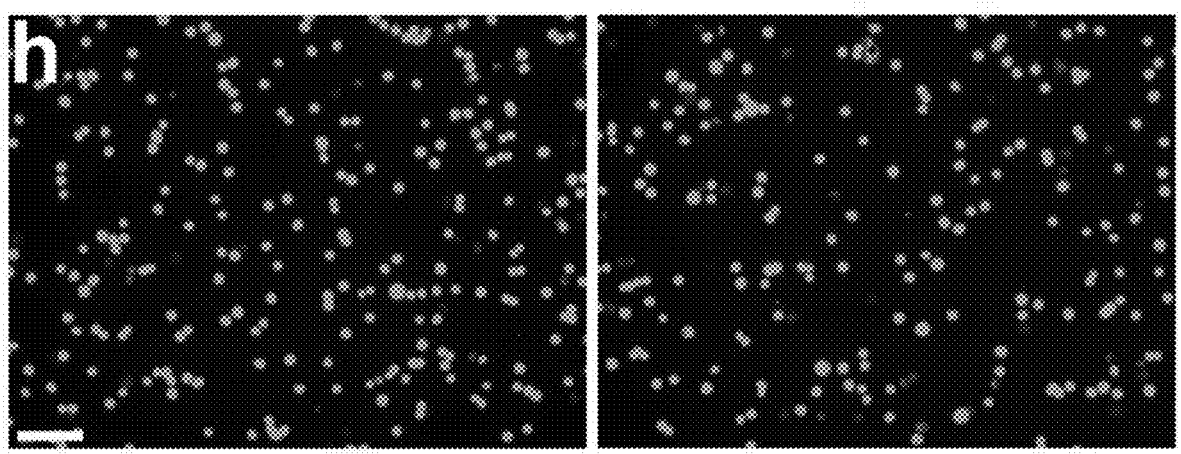
*FIG. 2.3H*
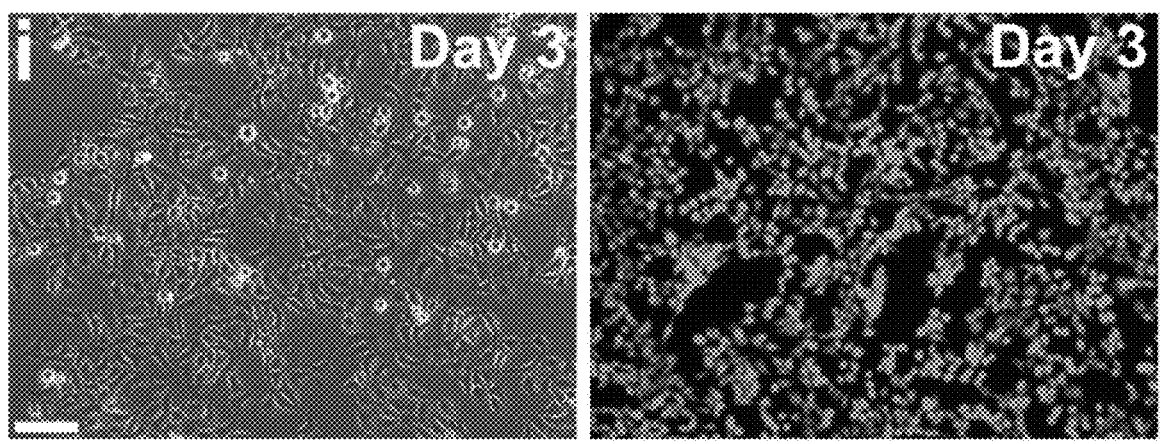
*FIG. 2.3I*

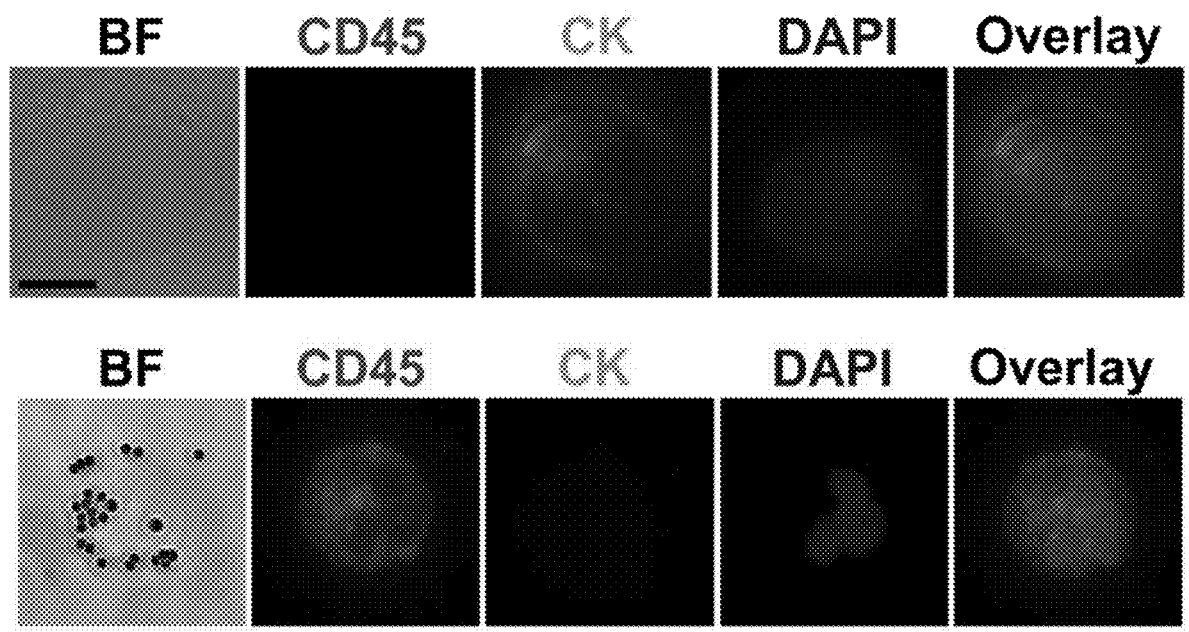
FIG. 2.3J

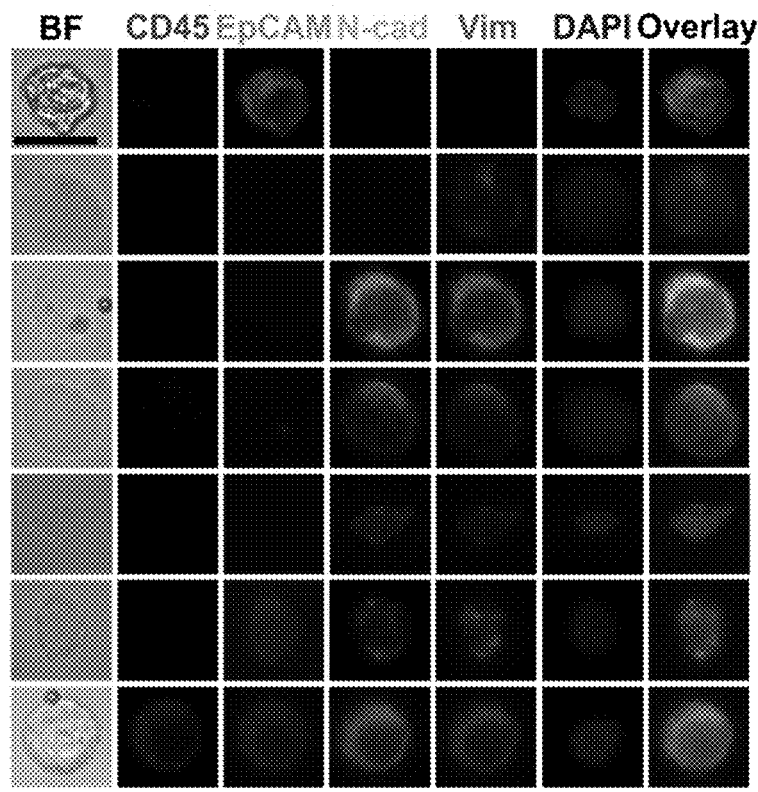
*FIG. 2.4A*
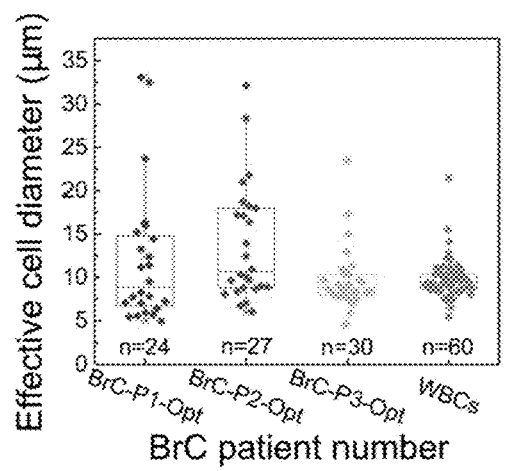
*FIG. 2.4B*
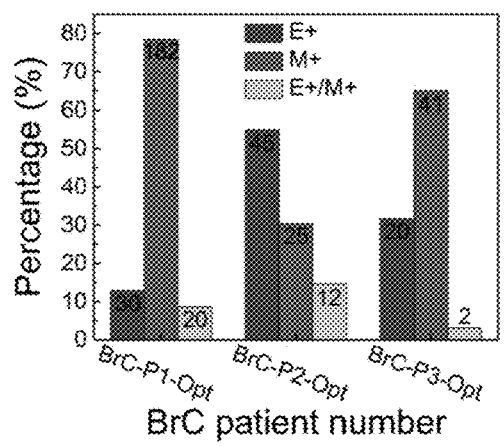
*FIG. 2.4C*

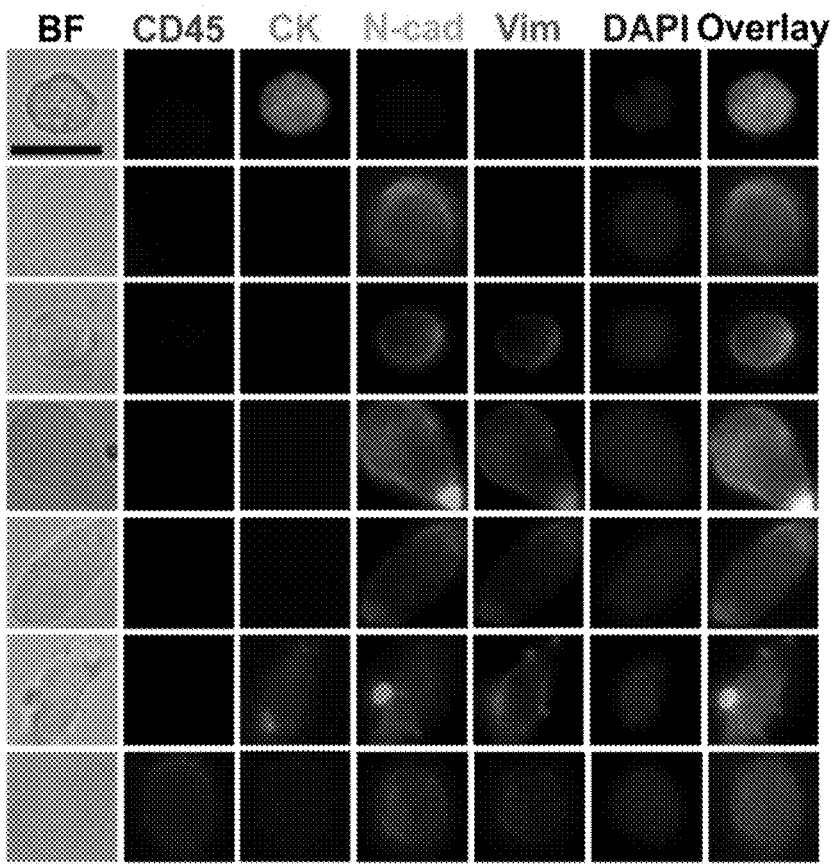
*FIG. 2.5A*
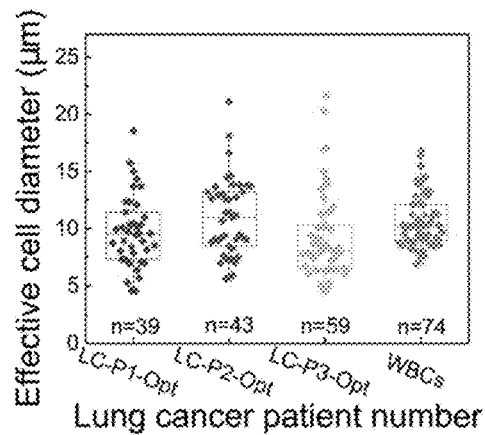
*FIG. 2.5B*
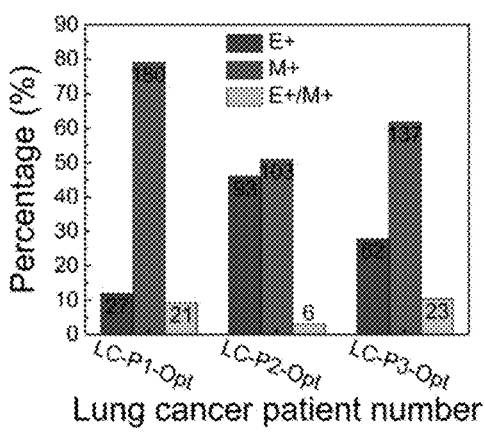
*FIG. 2.5C*

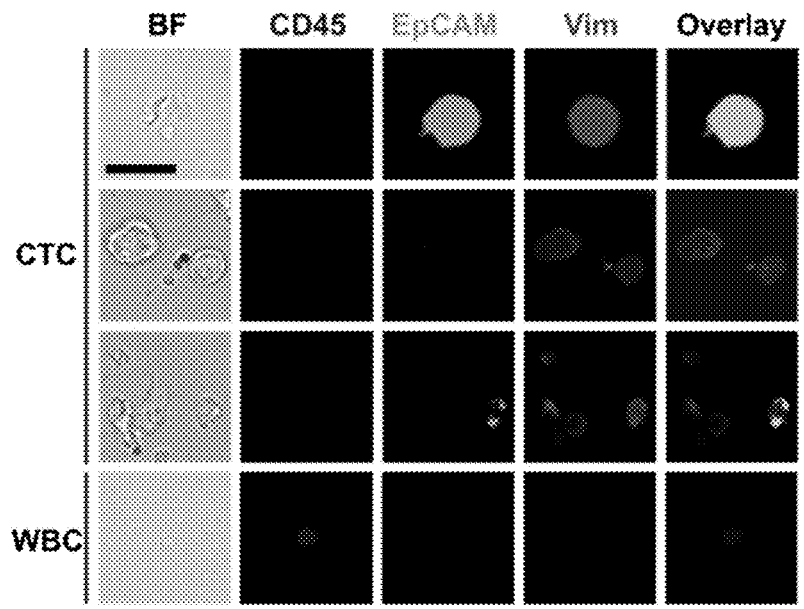
*FIG. 2.6A*
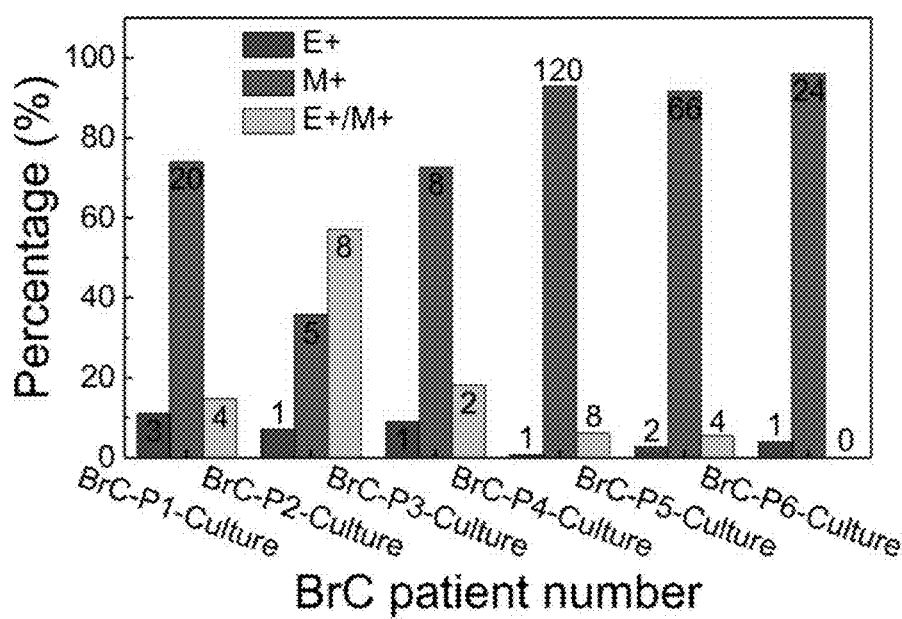
*FIG. 2.6B*

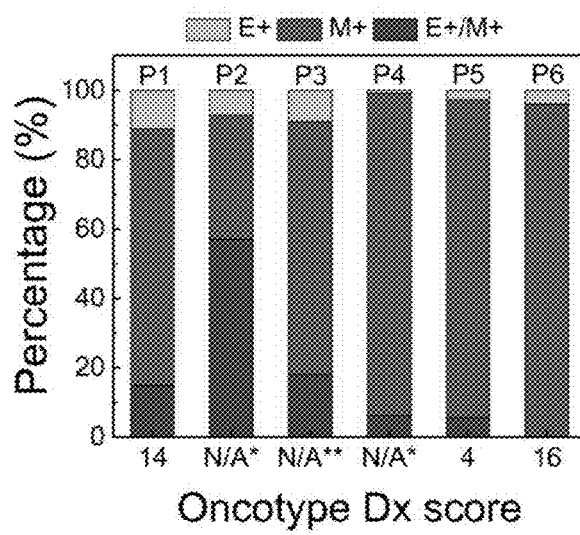
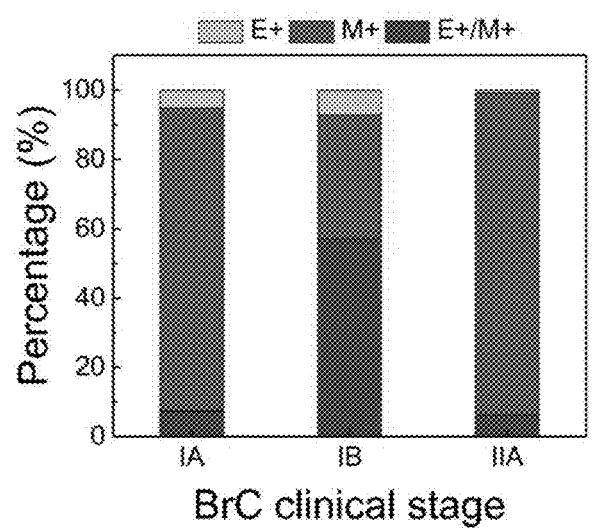
*FIG. 2.6C*  *FIG. 2.6D*
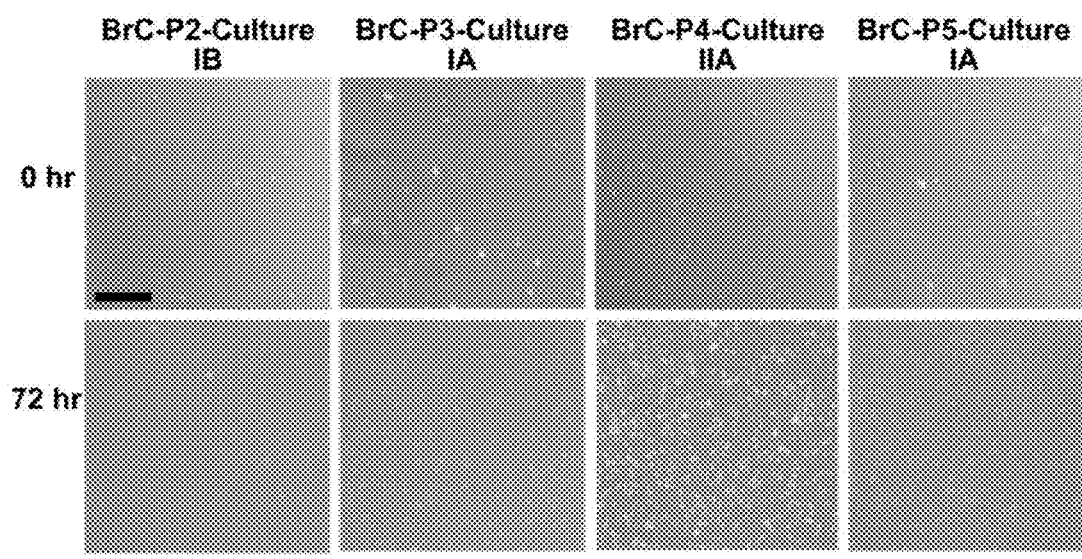
*FIG. 2.6E*

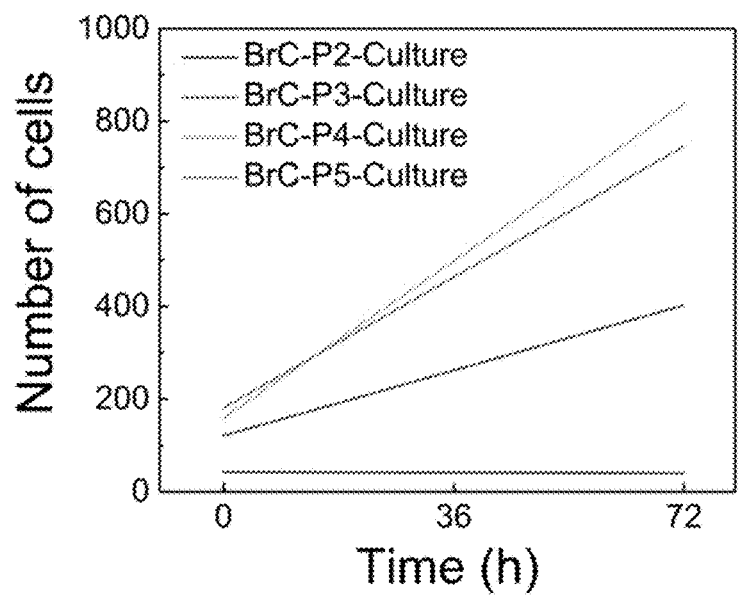
FIG. 2.6F
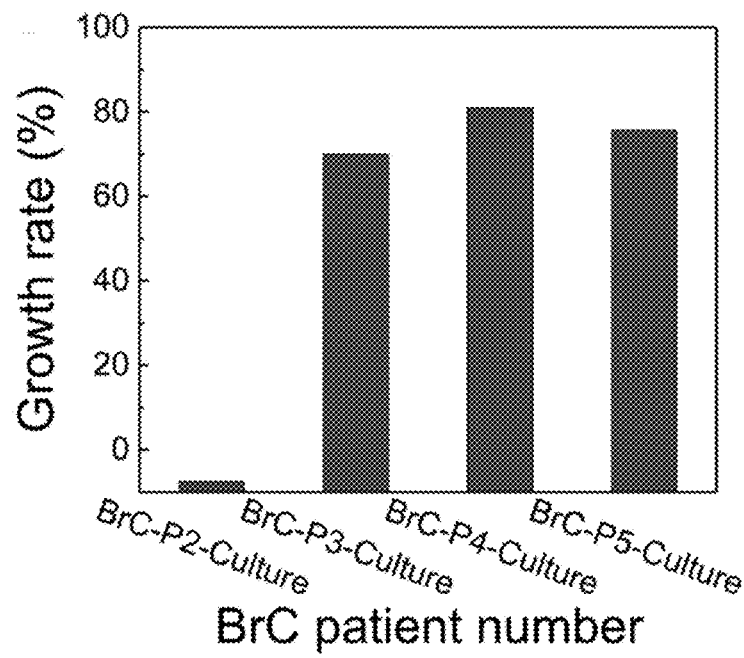
FIG. 2.6G

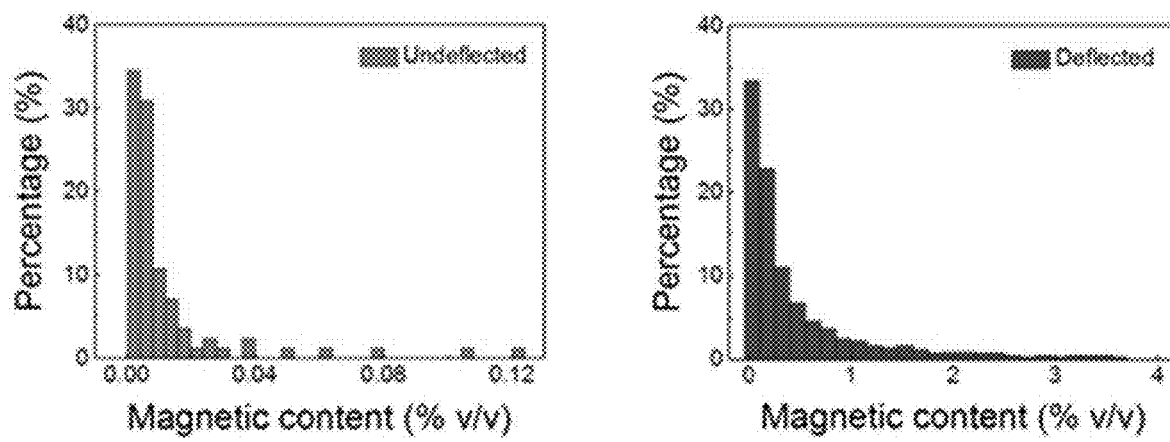
FIG. 3.1A
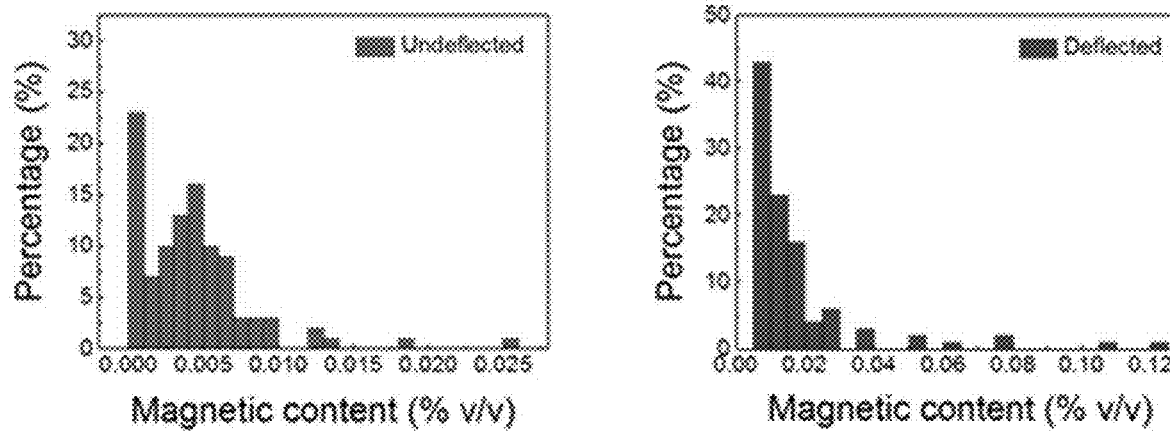
FIG. 3.1B

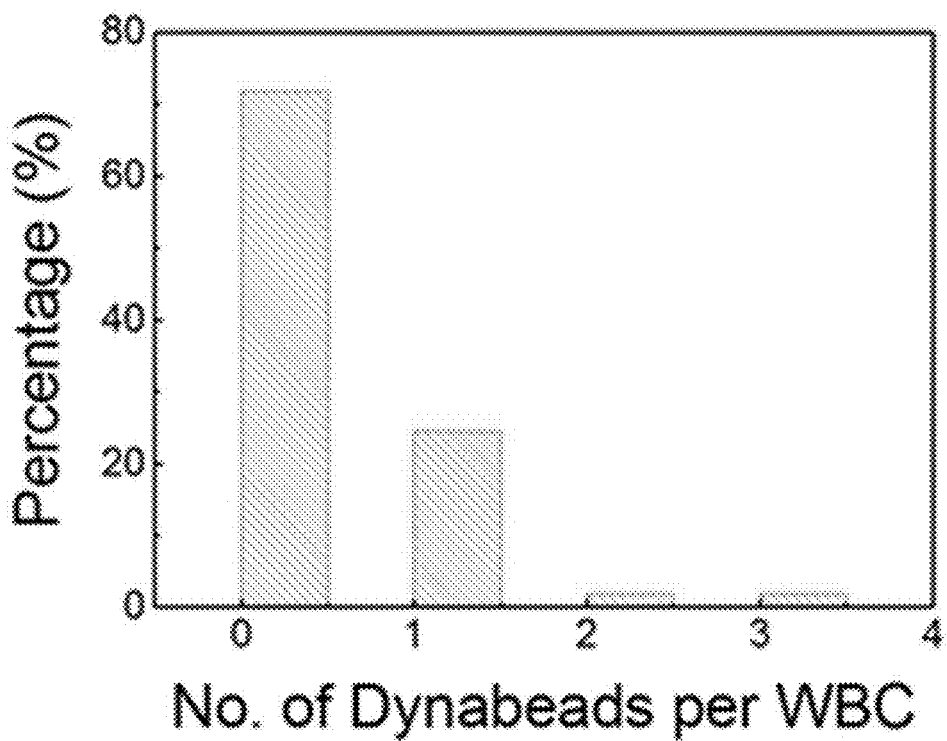
*FIG. 3.2*
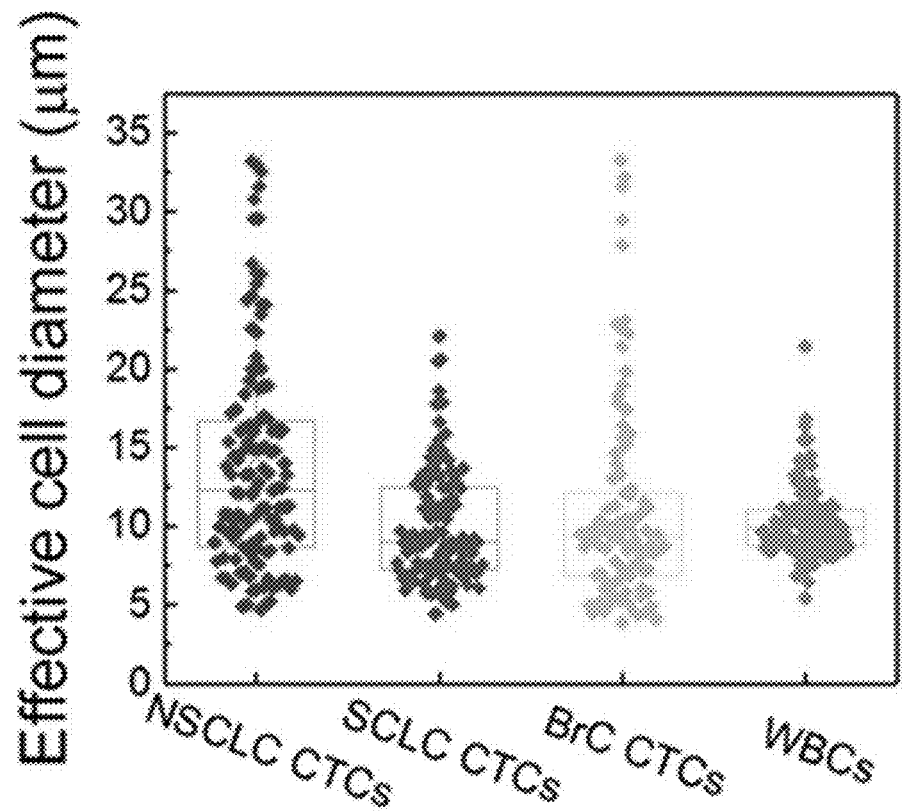
*FIG. 3.3*

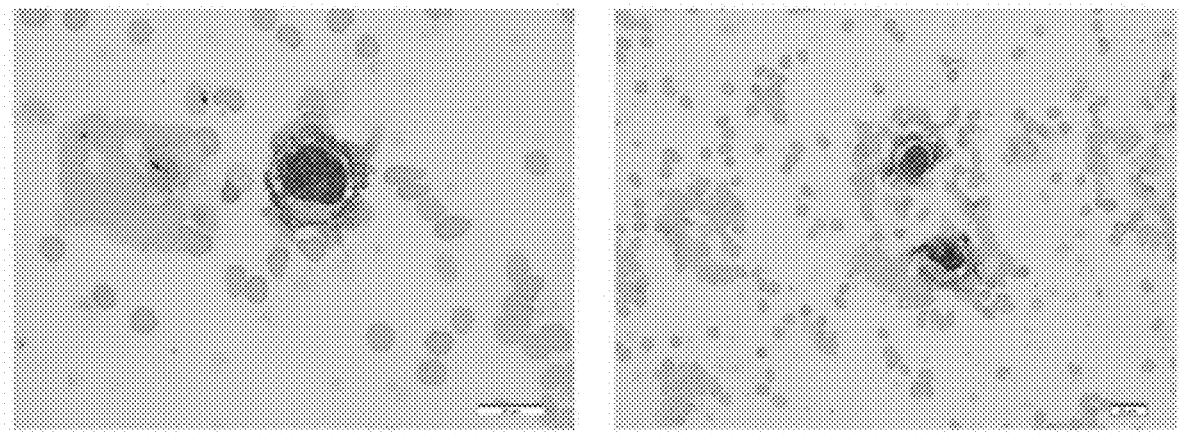
FIG. 3.4
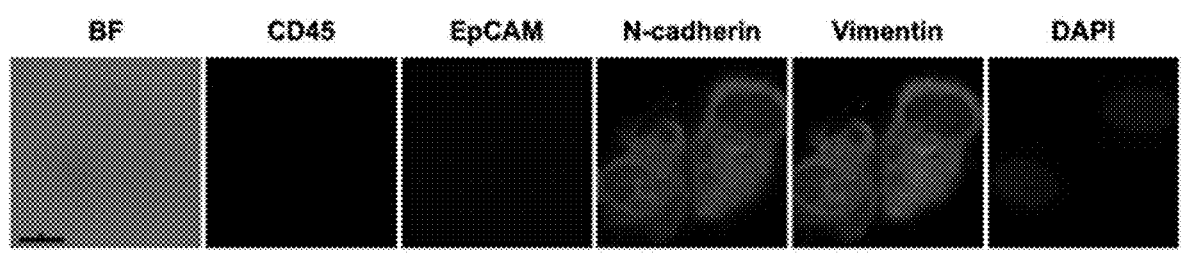
FIG. 3.5A
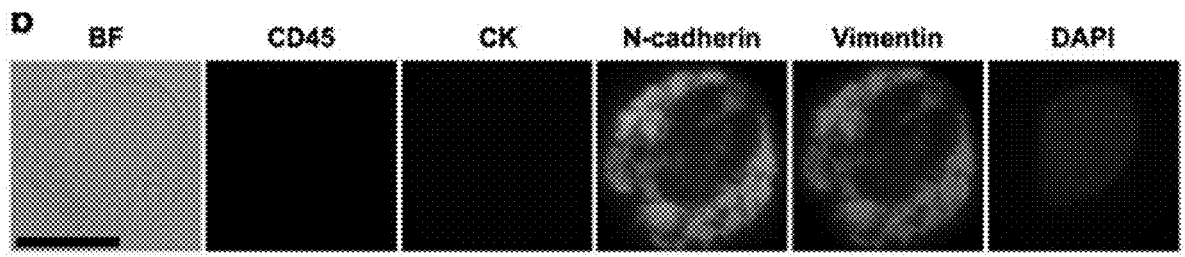
FIG. 3.5B

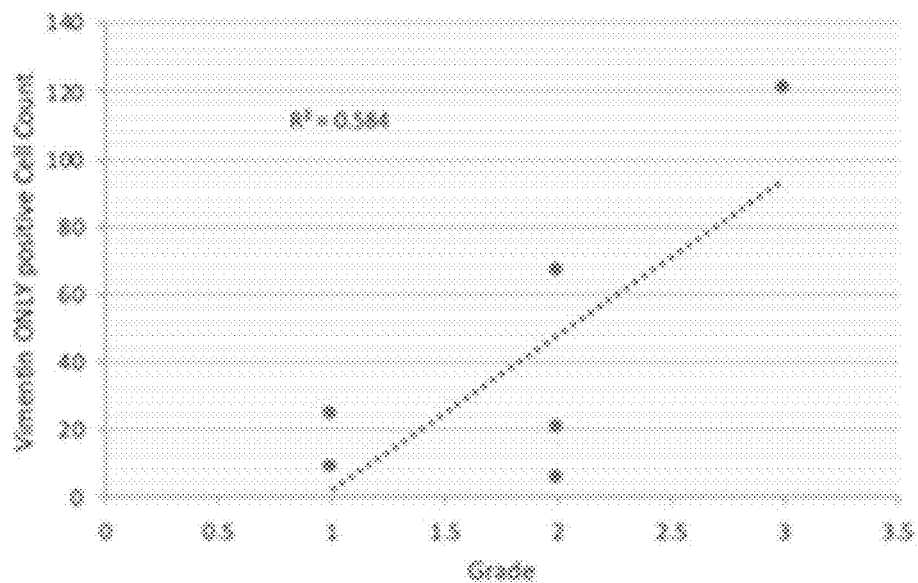
FIG. 3.6A
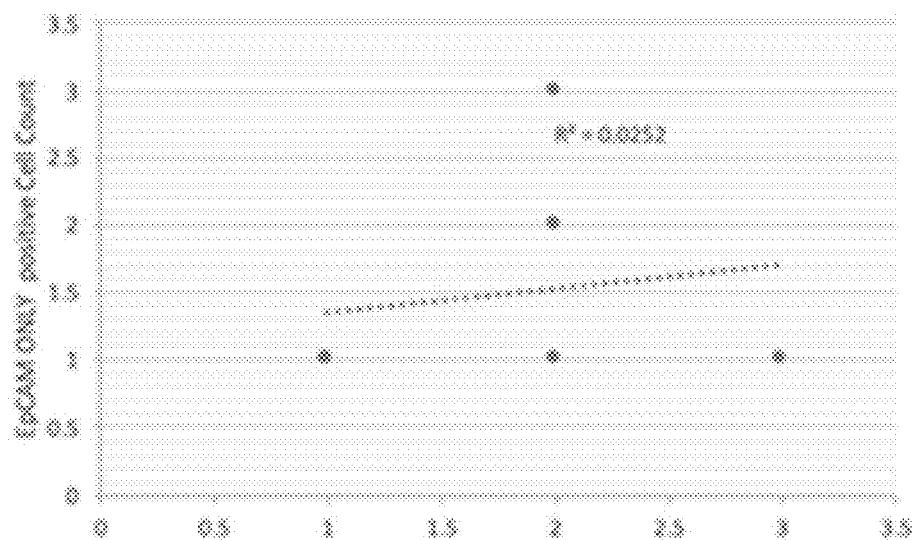
FIG. 3.6B
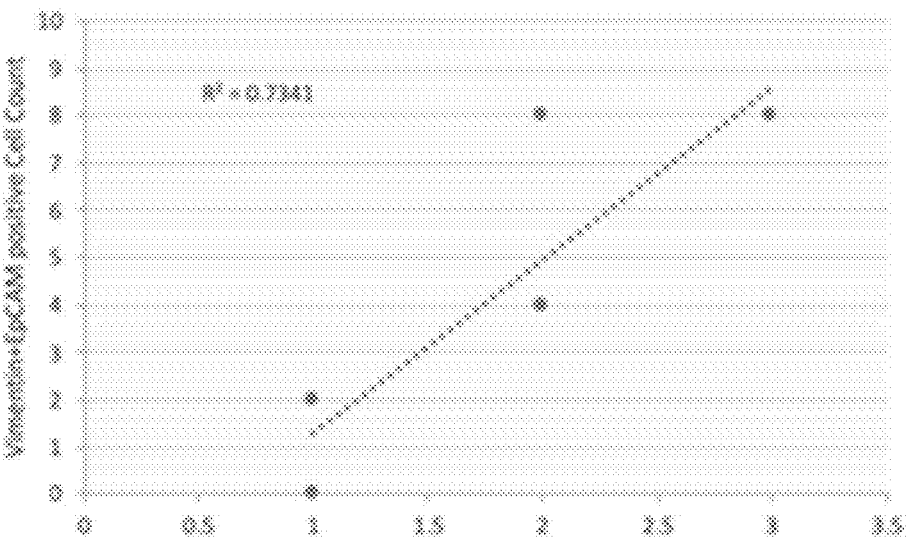
FIG. 3.6C

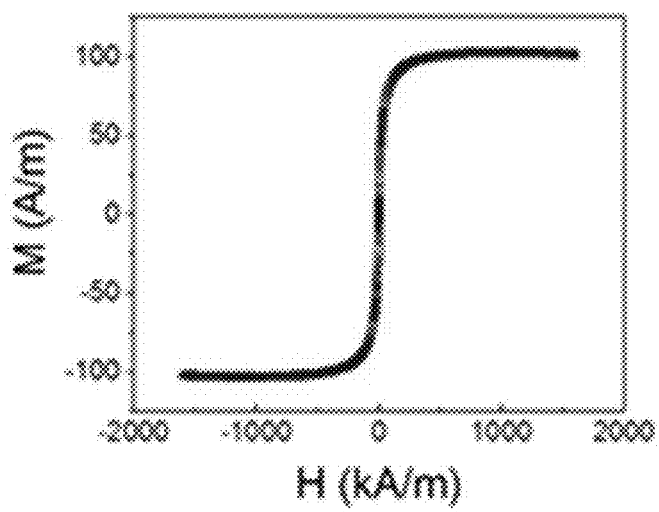
*FIG. 3.7A*
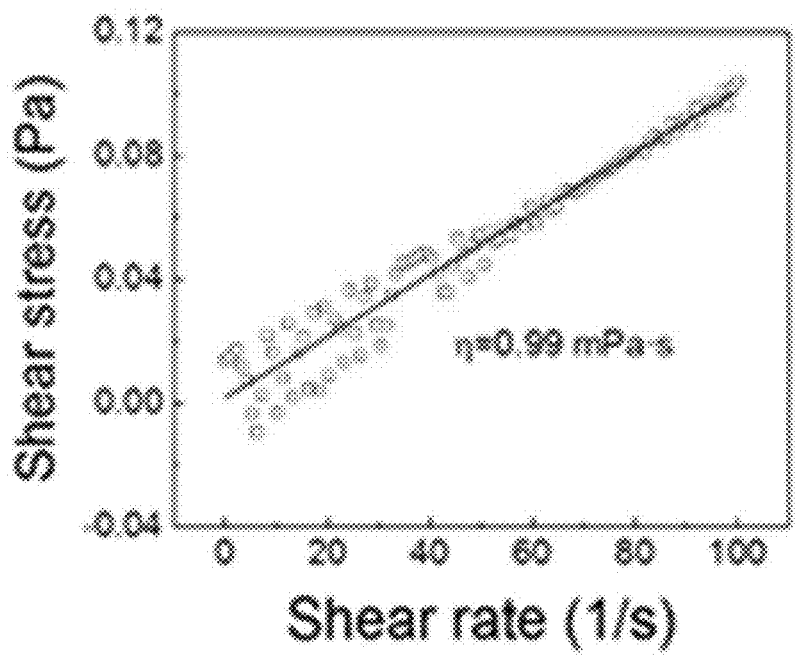
*FIG. 3.7B*
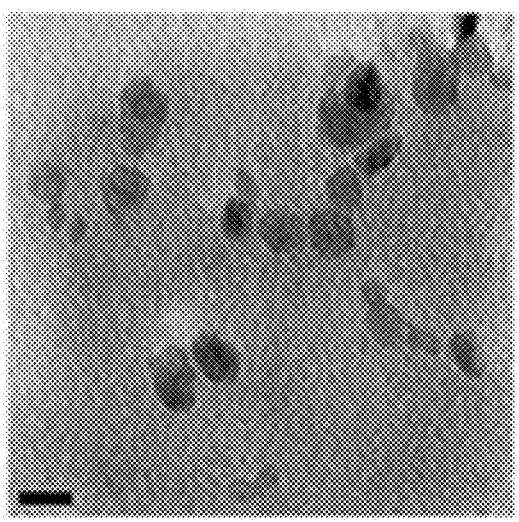
*FIG. 3.7C*

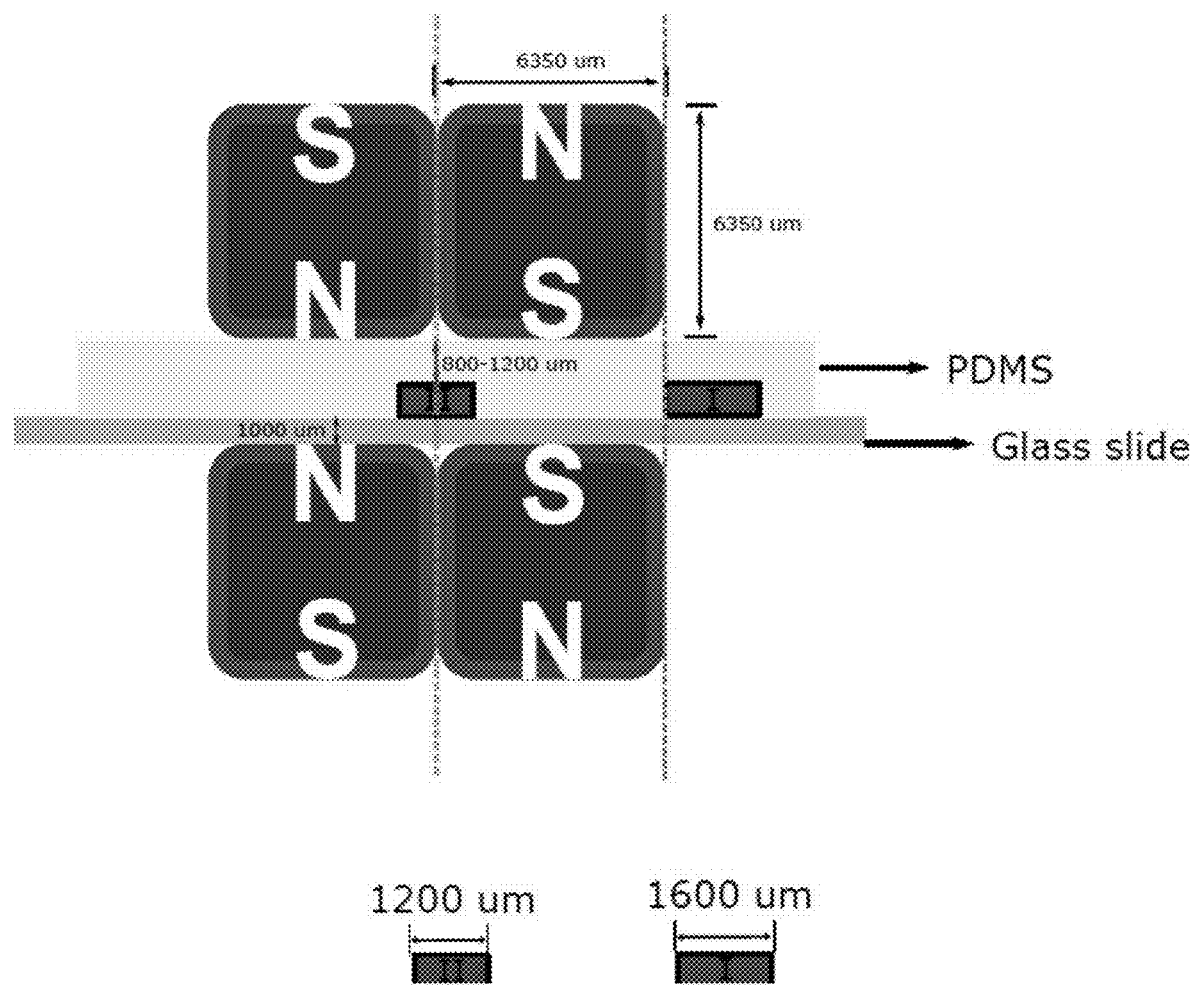
FIG. 3.8

DEVICES AND METHODS FOR SEPARATING CIRCULATING TUMOR CELLS FROM BIOLOGICAL SAMPLES

CROSS-REFERENCE TO RELATED APPLICATIONS

This application claims priority to, and the benefit of, U.S. provisional application entitled "MICROFLUIDIC MAGNETIC CELL SORTER FOR BREAST CANCER CIRCULATING TUMOR CELLS" having Ser. No. 62/668,355, filed May 8, 2018 and U.S. provisional application entitled "DEVICES AND METHODS FOR SEPARATING CIRCULATING TUMOR CELLS FROM BIOLOGICAL SAMPLES" having Ser. No. 62/826,539, filed Mar. 29, 2019, both of which are incorporated by reference in their entirety. This application is also a continuation-in-part of and claims benefit of co-pending PCT application entitled "DEVICES AND METHODS FOR SEPARATING CIRCULATING TUMOR CELLS FROM BIOLOGICAL SAMPLES" having International Application No. PCT/US18/45294, filed Aug. 4, 2018, which claims priority to U.S. provisional application entitled "CELL SEPARATION OF TUMOR CELLS" having Ser. No. 62/541,552, filed Aug. 4, 2017, all of which are incorporated by reference in their entirety.

STATEMENT REGARDING FEDERALLY SPONSORED RESEARCH OR DEVELOPMENT

This invention was made with government support under award 1150042 and award 1359095 and 1659525 awarded by the National Science Foundation and award R21GM104528 awarded by the National Institutes of Health and award UL1TR002378 awarded by the National Center for Advancing Translational Sciences of the National Institutes of Health. The government has certain rights in the invention.

TECHNICAL FIELD

The present disclosure generally relates to microfluidics and uses thereof.

BACKGROUND

Circulating tumor cells (CTCs) are cancer cells that are detached from primary solid tumors and carried through the vasculature to potentially seed distant site metastases in vital organs, representing the main cause of death in cancer patients. Molecular assessments of CTCs not only could benefit basic cancer research, but also might eventually lead to a more effective cancer treatment. However, one major limitation has been the limited availability of viable CTCs for investigations, due in part to the small patient blood volumes that are allowable for research, which usually yielded less than 100 CTCs from 1 mL of whole blood. As a result, technologies are needed in order to separate these rare cells from blood, and important performance criteria for these technologies include the ability to process a significant amount of blood quickly (e.g., throughput ~7.5 mL h$^{-1}$), a high recovery rate of CTCs, a reasonable purity of isolated cancer cells, and cell integrity for further characterization.

Label-based CTC separation technologies were developed to selectively enrich a subset of CTCs from blood, primarily through the use of specific biological markers including epithelial cell adhesion molecule (EpCAM) (FIG. 1A). These antigen-based labels were a rate-limiting factor in effective CTC separation, as the inherent heterogeneity of CTCs render these technologies ineffective for general use. The vast array of various biomarkers that might or might not be expressed, and which cannot be predicted to remain expressed in CTCs undergoing Epithelial-to-Mesenchymal Transitions (EMT) are cumbersome and confounding in these label-based methods. Furthermore, most label-based technologies do not conveniently enable comprehensive molecular analysis of separated CTCs because they are either dead or immobilized to a surface. Thus, a variety of label-free methods have been developed to exploit specific physical markers in order to deplete non-CTCs in blood and thereby enrich cancer cells. While such methods may be used to separate CTCs based upon, for example, size, the existence of large white blood cells, such as monocytes, that may have overlapping sizes with CTCs complicate these label-free methods and reduce the purity of the sample obtained. Other devices have attempted to incorporate two or more of these methods, but still suffer from the time-consuming and laborious sample preparation due to the complications discussed above for labeling CTCs.

There remains a need for improved devices and methods for separating circulating tumor cells that overcome the aforementioned deficiencies.

SUMMARY

In various aspects, microfluidic devices and methods of using microfluidic devices are provided that overcome one or more of the aforementioned deficiencies. The devices and methods can combine filters, sheathing separation, and flow focusing to provide for high throughput cell separation without the need for labeling the CTCs.

The present disclosure provides cell separation system and devices for enriching circulating tumor cells in a biological sample. In aspects, the system includes a plurality of magnetic microbeads for conjugation to white blood cells in the sample, a biocompatible superparamagnetic sheathing composition, and a multi-stage microfluidic device comprising first, second, and third microfluidic channels, and comprising one or more magnetic sources, the device configured to remove waste particles from the sample, remove a plurality of magnetically conjugated white blood cells from the sample, and to enrich circulating tumor cells in the sample. In embodiments of the systems of the present disclosure, included are a plurality of magnetic microbeads adapted for conjugation to white blood cells in the biological sample and not for conjugation with the circulating tumor cells configured to provide a magnetically labeled biological sample having a majority of the white blood cells in the biological sample conjugated to one or more magnetic microbeads. In aspects of systems of the present disclosure, the biocompatible superparamagnetic sheathing composition comprises a plurality of magnetic nanoparticles and a biocompatible surfactant, the biocompatible superparamagnetic sheathing composition adapted to be combined with a biocompatible carrier fluid to make a biocompatible superparamagnetic sheathing fluid.

In various aspects, the multi-stage microfluidic device of systems of the present disclosure includes: (i) a filter section comprising a first microfluidic channel, a first fluid inlet, and one or more filters along a length of the first microfluidic channel, wherein the first fluid inlet is configured to receive the magnetically labeled biological sample, and wherein the one or more filters are configured to remove a first plurality of waste particles from the magnetically labeled biological sample; (ii) a first separation stage comprising a second microfluidic channel fluidly connected to the first microfluidic channel and having a second fluid inlet to receive the biocompatible superparamagnetic sheathing fluid, and a first fluid outlet at an end of the second microfluidic channel and offset from a central diameter of the second microfluidic channel, wherein the second microfluidic channel is configured to combine the magnetically labeled biological sample from the first filter section with the biocompatible superparamagnetic sheathing fluid; (iii) a second separation stage comprising a third microfluidic channel fluidly connected to the second microfluidic channel and having a second fluid outlet and at least a first circulating tumor cell outlet and second circulating tumor cell outlet; and (iv) one or more magnetic sources adjacent to the multi-stage microfluidic device. In aspects, the one or more magnetic sources are configured to produce: (a) a non-uniform magnetic field along the second microfluidic channel having a component sufficiently perpendicular to a length of the second microfluidic channel to cause a plurality of white blood cells conjugated to the magnetic beads to be deflected into the first fluid outlet; and (b) a substantially symmetric magnetic field having a field maximum along a length of the third microfluidic channel sufficient to cause the white blood cells conjugated to the magnetic beads in the third microfluidic channel to be focused toward a center of the third microfluidic channel and to exit the channel via the second fluid outlet and to cause circulating tumor cells to be deflected towards an outer portion of the third microfluidic channel and to exit the channel via the first or second circulating tumor cell outlet.

The present disclosure also provides multi-stage microfluidic devices for enriching circulating tumor cells in a biological sample. In various embodiments, the devices of the present disclosure include: (i) a filter section comprising a first microfluidic channel, a first fluid inlet, and one or more filters along a length of the first microfluidic channel, wherein the first fluid inlet is configured to receive a biological sample comprising circulating tumor cells and white blood cells, wherein a majority of the white blood cells in the biological sample are conjugated to magnetic microbeads, and wherein the one or more filters are configured to remove a first plurality of waste particles from the biological sample; (ii) a first separation stage comprising a second microfluidic channel fluidly connected to the first microfluidic channel and having a second fluid inlet to receive a biocompatible superparamagnetic sheathing fluid, and a first fluid outlet at an end of the second microfluidic channel opposite the second fluid inlet and offset from a central diameter of the second microfluidic channel, wherein the second microfluidic channel is configured to combine the biological sample from the first filter section with the biocompatible superparamagnetic sheathing fluid, and wherein the biocompatible superparamagnetic sheathing fluid comprises a plurality of magnetic nanoparticles and a biocompatible surfactant suspended in a biocompatible carrier fluid; (iii) a second separation stage comprising a third microfluidic channel fluidly connected to the second microfluidic channel and having a second fluid outlet and at least a first circulating tumor cell outlet and second circulating tumor cell outlet; and (iv) one or more magnetic sources adjacent to the multi-stage microfluidic device and configured to produce: (a) a non-uniform magnetic field along the second microfluidic channel having a component sufficiently perpendicular to a length of the second microfluidic channel to cause a plurality of white blood cells conjugated to the magnetic beads to be deflected into the first fluid outlet; and (b) a substantially symmetric magnetic field having a field maximum along a length of the third microfluidic channel sufficient to cause the white blood cells conjugated to the magnetic beads in the third microfluidic channel to be focused toward a center of the third microfluidic channel and to exit the channel via the second fluid outlet and to cause circulating tumor cells to be deflected towards an outer portion of the third microfluidic channel and to exit the channel via the first or second circulating tumor cell outlet.

Methods of enriching circulating tumor cells in a biological sample comprising a plurality of components are also provided in the present disclosure. According to various aspects, the method comprises: combining the biological sample with a plurality of magnetic microbeads adapted to conjugate to white bloods cells such that a majority of white blood cells in the sample become conjugated to at least one magnetic microbead to produce a magnetically labeled biological sample; introducing the magnetically labeled biological sample into the first fluid inlet of a microfluidic device according the present disclosure; introducing the biocompatible superparamagnetic sheathing fluid into the second fluid inlet of the microfluidic device, such that the magnetically labeled biological sample combines with the biocompatible superparamagnetic sheathing fluid to produce a combined fluid sample; and causing the combined fluid sample to flow along the first microfluidic channel, the second microfluidic channel, and the third microfluidic channel such that a majority of the magnetic microbeads and white blood cells are deflected to the first or second fluid outlet and a majority of the circulating tumor cells from the biological sample are collected in the one or more circulating tumor cell outlets.

The present disclosure also provides methods of enriching circulating tumor cells in a sample of whole blood, where the whole blood comprises unlabeled rare cells and white blood cells. In various aspects, the method includes: (i) adding a plurality of magnetic beads to the sample to produce a magnetically labeled sample, wherein a majority of the white blood cells are associated with the magnetic beads and wherein the magnetic beads do not conjugate to the unlabeled rare cells; (ii) filtering the magnetically labeled sample in a filter section of a microfluidic device to produce a filtered sample by removing large debris from the magnetically labeled sample; (iii) separating at least a portion of the white blood cells that are associated with the magnetic beads by flowing the filtered sample in a first separation stage of the microfluidic device through a sheath flow in a biocompatible superparamagnetic sheathing fluid in a non-uniform magnetic field to produce a first enriched sample; and (iv) isolating a majority of the unlabeled rare cells by flowing the first enriched sample through a channel in a second separation stage of the microfluidic device with a substantially symmetric focused magnetic field such that a majority of any remaining white blood cells associated with the magnetic beads are focused towards a center of the channel and to a central channel outlet and the majority of the unlabeled rare cells are collected from one or more peripheral channel outlets.

Other systems, methods, devices, features, and advantages of the devices and methods will be or become apparent to one with skill in the art upon examination of the following drawings and detailed description. It is intended that all such additional systems, methods, devices, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1.1A is a schematic illustration of traditional label-based magnetophoresis for CTC separation, in which rare cells were targeted via specific biomarkers such as epithelial cell adhesion molecule (EpCAM) through functionalized magnetic particles in order to pull these cells through magnetic force towards magnetic field maxima in a continuous-flow manner. FIG. 1.1B is a schematic illustration of label-free ferrohydrodynamic cell separation (FCS) for CTCs. Large rare cells in ferrofluid experience large magnetic buoyance force and will be pushed towards magnetic field minimum FIG. 1.1C is a schematic of integrated ferrohydrodynamic cell separation (iFCS) for CTC separation. In iFCS, RBC-lysed blood and biocompatible ferrofluid were processed in a single straight channel. CTCs of different size and labelled WBCs were pushed toward two different directions, resulting in a spatial separation at the end of the iFCS device. FIG. 1.1D is a photograph of a prototype iFCS device filled with dye and a permanent magnet. FIG. 1.1E is a top-view of the iFCS device with labels of inlets, outlets. FIG. 1.1F is a simulation of magnetic flux density and particle trajectories of magnetic particles and non-magnetic particles in channel (L×W×H, 57.80 mm×0.90 mm×0.15 mm)

FIGS. 1.2A-1.2I show optimization of iFCS device via simulation and beads calibration. A 3D model was developed to simulate particle trajectories and validated by comparing simulation and experimental results. Numerical optimization of final position Y, separation distance ΔY, and the expected range (standard deviation) at the end of the channel was conducted with different parameters: (FIGS. 1.2A, 1.2D, and 1.2G) throughput, (FIGS. 1.2B, 1.2E, and 1.2H) ferrofluid concentration, and (FIGS. 1.2C, 1.2F, and 1.2I) magnetic field gradient. Ferrofluid concentration was fixed at 0.292% for FIG. 1.2A, FIG. 1.2D, FIG. 1.2G, FIG. 1.2C, FIG. 1,2F, and FIG. 1.2I. Magnetic field gradient was fixed at 132 T m$^{-1}$ for FIGS. 1.2A, 1.2D, and 1.2G. Throughput was fixed at 100 μL min$^{-1}$ for FIGS. 1.2B, 1.2E, 1.2, 1.2C, 1.2F, and 1.2I. FIGS. 1.2D, 1.2E, and 1.2F were simulated particles positions and corresponding standard deviations. FIGS. 1.2G, 1.2H, and 1.2I were normalized particle distributions in experiment.

FIGS. 1.3A-1.3F demonstrate iFCS applied to multiple beads separation. FIG. 1.3A shows average separation distance between non-magnetic beads and magnetic beads. Non-magnetic beads (20.3 μm, 8.0 μm and 5.7 μm) and magnetic beads (11.8 μm) were spiked into 0.292% ferrofluid at throughput between 10 and 350 μL min$^{-1}$. The magnetic field gradient was fixed at 132 T m$^{-1}$. FIG. 1.3B illustrates simulated and experimental separation distance between 8.0 μm non-magnetic beads and 11.8 μm magnetic beads at low ferrofluid concentration between 0.01% and 0.1%, and flow rate between 10 and 210 μL min$^{-1}$. The magnetic field gradient was fixed at 132 T m$^{-1}$. FIG. 1.3C illustrates particle trajectories of 8.0 μm non-magnetic beads at the flow rate of 100 μL min$^{-1}$. A ferrofluid with its concentration of 0.049% (v/v) was used; the magnetic field gradient was fixed at 132 T m$^{-1}$. Scale bar: 200 μm. FIG. 1.3D shows that, in absence of magnetic fields, all of the beads (20.3 and 8.0 μm non-magnetic beads, and 11.8 μm magnetic beads) were randomly distributed in the channel. Scale bar: 200 μm. FIG. 1.3E illustrates that, when magnetic fields were present, non-magnetic beads (20.3 and 8.0 μm) will be collected from outlet 1. Most of the magnetic beads (11.8 μm) will be collected at outlet 3, and the rest can be identified in outlet 2. Scale bar: 200 μm. FIG. 1.3F is an image of collected beads from 3 outlets. The red fluorescent signal comes from 8.0 μm non-magnetic beads and the yellow fluorescent signal comes from 11.8 μm magnetic beads. Scale bar: 200 μm.

FIGS. 1.4A-1.4C demonstrate size of cancer cell lines and labelling results of WBCs. FIG. 1.4A illustrates the size distribution of different cancer cell lines—Prostate (PC-3), Breast (MCF-7, MDA-MB-231, HCC1806) and Lung (H1299, H3122, H69, DMS79), and white blood cells from healthy donor. FIG. 1.4B illustrates the number of magnetic beads (dynabeads) per white blood cell (n=1000). The average is 34±11 dynabeads per WBC. Insect is a WBC labelled with 45 beads. FIG. 1.4C illustrates the percentage of magnetic content in labelled WBCs. The volume fraction of magnetic content in dynabeads is 11.5%, the magnetic content for labelled WBC was calculated based on volume fraction.

FIGS. 1.5A-1.5F show iFCS applied to cancer cells separation. Certain numbers of PC-3 prostate cancer cells and 1×10$^6$ WBCs were spiked into 1 mL ferrofluid with concentration of 0.049% (v/v). The cell mixture was processed at the flow rate of 100 μL min$^{-1}$; the magnetic field gradient was fixed at 132 T m$^{-1}$. FIG. 1.5A shows bright field and fluorescent images of 1×10$^5$ PC-3 cancer cells and WBCs separation process. Green signal comes from PC-3 cancer cells and red signal comes from WBCs Scale bar: 500 μm. FIG. 1.5B illustrates collected PC-3 from outlet 1. FIG. 1.5C shows normalized size distributions of spiked and collected cancer cells from outlet 1 for PC-3, MCF-7 and MDA-MB-231. FIG. 1.5D shows magnetic beads enumeration on collected WBCs from outlet 1 with different concentration of ferrofluid. FIG. 1.5E illustrates recovery rate and purity for different cancer cell lines (~100 cells per mL). Recovery rate of 97.9±1.0%, 97.6±1.0%, 98.8±1.4%, 99.4±0.6%, 98.7±0.6%, 95.0±1.2%, 95.9±1.3% and 99.7±0.6% were achieved for MCF-7, MDA-MB-231, HCC1806, H1299, H3122, DMS79, H69 and PC-3 cell lines, respectively. The corresponding purities are 212.0±1.3%, 23.5±0.7%, 25.2±1.5%, 23.1±0.9%, 22.2±0.9%, 24.2±1.7%, 21.7±0.8% and 23.3±0.4%, respectively. Error bars indicate standard deviation, n=3. FIG. 1.5F illustrates a series of experiments with different number of spiked PC-3 cancer cells (100, 250, 500, 1000 and 2000). An average recovery rate of 98.8% (linear fit, R$^2$=0.9998) was achieved for PC-3 cancer cells.

FIGS. 1.6A-1.6C illustrate an embodiment of an iFCS device design and operating principle. FIG. 1.6A is a top-view of the FCSv2 device with labels of inlets, debris filters and outlets. The arrow indicates the direction of magnetic field during device operation. The device integrates 3 stages into one single device for biomarker- and size-independent CTC enrichment. Stage one filters out large cell debris. As illustrated in FIG. 1.6B, stage 2 depletes the unbound magnetic beads and WBCs bound with beads into waste outlet 1 (FIG. 1.6B ii). FIG. 1.6B iii illustrates that stage 3 continuously deflects unlabeled CTCs into collection outlet, while at the same time focuses WBCs bound with bead into waste outlet 2. FIG. 1.6C is a digital image of the embodiment of the microfluidic device illustrated in FIG. 1.6A sandwiched between device holders, which include top and bottom magnet arrays repelling each other and are secured with screws and nuts. The thickness of channel is 250 µm. The width of stage 2 is 1600 µm and width of stage 3 is 1200 µm.

FIG. 1.7 illustrates an embodiment of a microfluidic device of the present disclosure sandwiched between the two device holders, which include top and bottom magnet arrays repelling each other and secured with screws and nuts. The center of the stage 3's microchannel (see FIG. 1.6A) is aligned exactly with the center of the magnet arrays.

FIG. 1.8 illustrates a simulation result demonstrating that the magnetic field is stronger in the center of the stage 3 region of the device illustrated in FIG. 1.6A. As a result, the magnetically labeled white blood cells and free magnetic beads are focused in the center of the channel and are collected through the waste outlet. At the same time, any unlabeled cells, including circulating tumor cells are deflected into two sides of the channel and are collected through collection outlets. Whole blood is labeled and lysed by RBC lysing buffer before it is processed with the FCSv2. Leukocyte-specific biotinylated antibodies (anti-CD45, anti-CD66b and anti-CD16) and magnetic Dynabeads are added to the blood sample for incubation.

FIG. 1.9A illustrates the recovery rate of separated cancer cells for different cancer cell lines at the flow rate of 12 mL/h. recovery rates of 98.46±0.50%, 99.68±0.46%, 99.05±0.75%, 99.35±0.46%, 99.40±0.85%, 99.13±0.49%, 99.11±1.25%, and 99.11±0.74% are achieved for HCC1806 (breast cancer), HCC70 (breast cancer), MCF7 (breast cancer), MDA-MB-231 (breast cancer), H1299 (non-small cell lung cancer), H3122 (non-small cell lung cancer), DMS79 (small cell lung cancer), and H69 (small cell lung cancer) cell lines, respectively. FIG. 1.9B illustrates a series of spike-in separation experiments in which a certain number (20, 50, 100, and 200) of HCC70 breast cancer cells are spiked into 1 mL of labeled white blood cells. An average recovery rate is 99.08%.

FIGS. 1.10A-1.10B illustrate bright field and fluorescence image of spiked MDA-MB-231 breast cancer cells (labeled with CellTracker Green) during the separation process confirmed the cancer cell trajectories at the end of stages 2 and 3 in FIGS. 1.10A-1.10C. Scale bars: 500 µm.

FIGS. 2.1A-2.1D illustrate an integrated ferrohydrodynamic cell separation (iFCS) system and its working principle. FIG. 2.1A (top) is a schematic of an unlabeled circulating tumor cell (CTC) experiencing "diamagnetophoresis" in a colloidal magnetic nanoparticle suspension (ferrofluids) and moving towards the minima of a non-uniform magnetic field. Magnetization of the unlabeled CTCs $M_{CTC}$ is near zero and less than its surrounding ferrofluids $M_{fluid}$. The diamagnetic body force on the cell is generated from magnetic nanoparticle induced pressure imbalance on the cell surface, and is proportional to cell volume. FIG. 2.1A (bottom) is a schematic of a magnetic bead labeled white blood cell (WBC) experiencing both "diamagnetophoresis" from its cell surface and "magnetophoresis" from its attached beads in a ferrofluid and moving towards the maxima of a non-uniform magnetic field due to the fact that "magnetophoresis" outweighs "diamagnetophoresis". Magnetization of the WBC-bead conjugates $M_{WBC-bead}$ is larger than its surrounding ferrofluid medium $M_{fluid}$. Color bar indicates relative amplitude of the magnetic field. Red arrows show the direction of cell movement, small black arrows on cell surface show the direction of magnetic nanoparticle induced surface pressure on cells, while white arrows show the magnetophoretic force on magnetic beads. FIG. 2.1B illustrates two enrichment stages were integrated into a single iFCS device to achieve cell size variation-inclusive and tumor antigen-independent enrichment of viable CTCs, and simultaneous depletion of contaminating WBCs. Prior to device processing, WBCs in blood were labeled with magnetic microbeads through leukocyte surface biomarkers so that the overall magnetization of the WBC-bead conjugates was larger than surrounding ferrofluids. Magnetization of the unlabeled CTCs was less than ferrofluids. In the first stage, a magnetic field gradient was generated to push unlabeled and sheath-focused CTCs to remain at the upper boundary of a microchannel, while attract unbound magnetic microbeads and WBCs labeled with ≥3 microbeads towards a waste outlet. A significant percentage of magnetic beads and WBCs were depleted before the second stage to alleviate potential bead aggregation. In the second stage, a symmetric magnetic field with its maximum at the middle of the channel was used to attract remaining WBC-bead conjugates towards to the channel center for fast depletion, and direct unlabeled CTCs towards the upper and lower boundaries for collection. Green arrows with gradients indicate the distribution of magnetic fields in each stage. FIG. 2.1C illustrates a top-view of an embodiment of an iFCS microchannel. The microchannel includes a filter that removes large than ~50 µm debris, a first and second stage for CTC enrichment and WBC depletion. FIG. 2.1D is a digital image of prototype microchannel (left) and assembled iFCS device with four permanent magnets in quadrupole configuration inside a holder (right). The microfluidic device and permanent magnets were placed within an aluminum manifold during its operation. Scale bars: 1 cm.

FIGS. 2.2A-2.2E illustrate system optimizations of an embodiments of iFCS devices for high recovery (>99%) of viable and rare CTCs (down to ~10 cells $mL^{-1}$) with low WBC contamination (~500 cells $mL^{-1}$) at 12 mL $h^{-1}$ throughput. FIG. 2.2A illustrates optimization of magnetic flux density and its gradient in microchannels. Using four permanent magnets in a quadrupole configuration shown here, maximal flux density of up to 0.6 T in the first stage (top), and up to 1.5 T in the second stage (bottom) in x-y plane (z=0) were obtained. Cell trajectories shows that in the first stage WBCs (11.7 µm in diameter) labeled with ≥3 beads and unbound magnetic beads were continuously depleted into a waste outlet, while CTCs (15 µm in diameter) moved to the second stage. In the second stage, remaining WBCs labeled with <3 beads were further depleted, leaving CTCs at both upper and lower channel walls for collection. Cell flow rate of 200 µL $min^{-1}$ was used for simulation. Maximal magnetic flux density gradient is 256 T $m^{-1}$ in the first stage (top) and 625 T $m^{-1}$ in the second stage (bottom) in y-z plane (x=0) were obtained. Schematic of magnetic ($\vec{F}_m$) and hydrodynamic drag ($\vec{F}_d$) forces on cells and their moving direction (white arrows; endpoints of white arrows indicting the equilibrium/final positions of cells) are overlaid on top of magnetic flux density plots. FIG. 2.2B illustrates optimization of magnetic bead functionalization of WBCs. Top: distribution of number of magnetic Dynabeads per WBC (n=1000). On overage 34±11 Dynabeads are conjugated onto a single WBC. Inset is a WBC labeled with multiple Dynabeads. Scale bar: 10 µm. Bottom: Magnetic content in labeled WBCs. More than 99.9% of WBCs are labeled with at least one bead, resulting in a 0.026% volume fraction of magnetic materials. This percentage value was used in subsequent optimization of ferrofluid concentration in order to minimize WBC contamination at device's outlets. FIG. 2.2C Optimizations of CTC recovery and WBC depletion (proportional to separation distance ΔY) were conducted on parameters including ferrofluid concentration (top) and device throughput (bottom). An optimal ferrofluid concentration is found to be 0.028%, while the optimal throughput to process clinically relevant amount of blood is 200 μL min$^{-1}$. In this optimization, magnetic flux density and its gradient are the same as in a, bead functionalization of WBCs is the same as in FIG. 2.2B. FIG. 2.2D Visualization of CTC and WBC distributions at the end of microchannels in the first (top) and second (bottom) stages. CTCs were given a size range of 3-32 μm in diameter, while WBCs were given a size range of 5-25 μm in diameter. After the first stage, the majority of WBCs were depleted while all CTCs, regardless of their sizes, moved to the second stage. After the second stage, all CTCs were collected with a minimal number of WBCs contamination/carryover. Yellow areas indicate either transfer channel to the second stage or the collection outlets, while white areas indicate waste outlets. FIG. 2.2E illustrates quantification of CTC and WBC distributions at the end of microchannels in the first (top) and second (bottom) stages. Results show that 96.35% of initial WBCs were depleted after the first stage while all CTCs are preserved, including CTCs that are as small as 3 μm in diameter (top). After the second stage, 3.6% of initial WBCs were further depleted and still all CTCs are preserved (bottom). Overall, after two stages, 99.95% of WBCs are depleted from initial samples and all CTCs are preserved. Simulation parameters of d and e include: cell flow rate of 200 μL min$^{-1}$, ferrofluid with concentration of 0.028%, magnetic flux density of 0.64 T and 1.5 T for stage I and stage II, flux density gradient of 256 T m$^{-1}$ and 625 T m$^{-1}$ for stage I and stage II.

FIGS. 2.3A-2.3J illustrate validation of prototype iFCS devices using cultured cancer cells spiked into WBCs, for over 99% of cancer cell recovery with minimal WBC contamination (~500 cells mL$^{-1}$) at clinically relevant spike ratio (down to ~10 cells mL$^{-1}$) and throughput (12 mL h$^{-1}$). FIG. 2.3A illustrates visualization of cancer cell enrichment and WBCs depletion (top: bright field; bottom: epifluorescence). In the first stage of the device, magnetic force attracted labeled WBCs and unbound beads toward waste outlet 1, while unlabeled cancer cells moved continuously into the second stage. Cancer cells were labeled with green fluorescence. Scale bar: 500 μm. FIG. 2.3B demonstrates that, in the second stage, magnetic force deflected unlabeled cancer cells from cell mixture toward upper and lower collection outlets. At the same time, labeled WBCs were focused into the middle of the channel and depleted into waste outlet 2. Top: bright field; bottom: epifluorescence. Scale bar: 500 μm. Dashed lines in fluorescent images indicate the boundaries of the microchannel. FIG. 2.3C illustrates spike-in results from iFCS devices show high recovery (99.18%) of cancer cells. A series of spike-in enrichment experiments in which a certain number (10, 25, 50, 100, and 200) of HCC70 breast cancer cells were spiked into 1 mL of labeled WBCs to emulate clinically relevant CTC concentration at a cell-processing throughput of 12 mL h$^{-1}$. An average recovery rate of 99.18% was achieved ($R^2$=0.9999, n=3). FIG. 2.3D illustrates size distribution of 8 cancer cell lines and WBCs. Both cancer cells and WBCs are polydispersed with overlapping sizes, highlighting the need of iFCS development to enrichment CTCs in an antigen-independent and size inclusive manner. Mean diameter and standard deviations are listed in Table 2.2. FIG. 2.3E is a graph illustrating recovery rates of spiked cancer cells (~100 cells per mL) from the cancer cell lines, including two small cell lung cancer (SCLC) lines, at a flow rate of 12 mL h$^{-1}$. Recovery rates of 98.46±0.50%, 99.68±0.46%, 99.05±0.75%, 99.35±0.46%, 99.40±0.85%, 99.13±0.49%, 99.11±1.25%, and 99.11±0.74% were achieved for HCC1806, HCC70, MCF7, MDA-MB-231, H1299, H3122, DMS79 (SCLC), and H69 (SCLC) cell lines, respectively (n=3). FIG. 2.3F illustrates size distribution of spiked and recovered cancer cells after iFCS process, conducted in a single stage iFCS device. iFCS was able to preserve cancer cells of all sizes. Mean diameter and standard deviations of spiked and recovered cancer cells are listed in Table. 2.3. Inset: recovered PC-3 prostate cancer cells showed polydispersity in diameters. Smallest recovered PC-3 cells had a diameter of 6.64 μm. Scale bar: 20 μm. FIG. 2.3G illustrates short-term cell viability comparison before and after the iFCS process. Cell viability of HCC1806 breast cancer cells before and after enrichment is determined to be 98.30±0.56% and 97.69±0.70%, with little change. FIG. 2.3H shows representative images of Live/Dead staining for before (left) and after (right) enrichment. Calcein AM (green, live cells) and EhD-1 (red, dead cells) channels were merged. Scale bar: 100 μm. FIG. 2.3I shows representative images of cultured HCC1806 breast cancer cells after enrichment on $3^{rd}$d day. A Live/Dead staining of the cultured cells on day 3 shows excellent cell viability. Scale bar: 100 μm. FIG. 2.3J shows immunofluorescence images of an intact spiked HCC1806 cancer cell (left panel) and an intact white blood cell conjugated with multiple magnetic beads (right panel). Three channels including CK (green), CD45 (red), and DAPI (blue) were used. Scale bar: 10 μm. All error bars indicate s.d., n=3.

FIGS. 2.4A-2.4C illustrate variation in CTC sizes and heterogeneity of CTC surface antigen expressions from breast cancer patient samples (first cohort, n=3). FIG. 2.4A represent bright field and immunofluorescent images of 7 selected individual CTCs enriched from 3 breast cancer (BrC) patients. Five channels were used in immunofluorescent staining, including leukocyte marker CD45 (red), epithelial CTC marker EpCAM (green), mesenchymal CTC markers N-cadherin (N-cad, cyan) and vimentin (Vim, magenta), and nucleus marker DAPI (blue). White blood cells were identified as CD45+/EpCAM-/N-cad-/Vim-/DAPI+, while CTCs were identified as either EpCAM+/CD45-/DAPI+ (epithelial positive), or N-cad+/Vim+/CD45-/DAPI+ (mesenchymal positive), or EpCAM+/N-cad+/Vim+/CD45-/DAPI+ (both epithelial and mesenchymal positive). Scale bar: 10 μm. FIG. 2.4B is a graph representing quantitative analysis of the effective diameter (maximum feret diameter of cells from their bright field images) of individual CTCs and WBCs enriched from 3 breast cancer patients' samples. Randomly selected CTCs from these patients revealed a high polydispersity of cell sizes. CTCs from patient 1 (breast cancer, stage IIIA, BrC-P1-Opt) had diameters of 11.99±7.87 μm (n=24; mean±s.d.; smallest 4.95 μm; largest 33.11 μm); CTCs from patient 2 (breast cancer, stage IA, BrC-P2-Opt) had diameters of 13.73±6.76 μm (n=26; mean±s.d.; smallest 6.00 μm; largest 32.10 μm); CTCs from patient 3 (breast cancer, stage IA, BrC-P3-Opt) had diameter of 9.67±3.60 μm (n=30; mean±s.d.; smallest 4.51 μm; largest 23.48 μm). WBCs pooled from 3 breast cancer patients had diameter of 9.83±2.27 μm (n=60; mean±s.d.; smallest 5.48 μm; largest 21.45 μm) FIG. 2.4C is a graph representing analysis of surface antigens expression of individual CTCs from 3 breast cancer patients' samples revealed a high heterogeneity of epithelial and mesenchymal characteristics in these cells. Cells from each patient are grouped into three categories (columns): epithelial positive (E+: EpCAM+/CD45-/DAPI+), mesenchymal positive (M+: N-cad+/Vim+/CD45-/DAPI+), both epithelial and mesenchymal positive (E+/M+: EpCAM+/N-cad+/Vim+/CD45−/DAPI+). Numbers in each column indicate the absolute number of cells in each category. For BrC-P1-Opt, 12.93% of CTCs was epithelial positive, 78.45% of CTCs was mesenchymal positive, and 8.62% was both epithelial and mesenchymal positive. For BrC-P2-Opt, 54.88% of CTCs was epithelial positive, 30.49% of CTCs was mesenchymal positive, and 14.63% was both epithelial and mesenchymal positive. For BrC-P3-Opt, 31.75% of CTCs was epithelial positive, 65.08% of CTCs was mesenchymal positive, and 3.17% was both epithelial and mesenchymal positive.

FIGS. 2.5A-2.5C illustrate variation in CTC sizes and heterogeneity of CTC surface antigen expressions from lung cancer patient samples (second cohort, n=3). FIG. 2.5A represents bright field and immunofluorescent images of 7 selected individual CTCs enriched from 3 lung cancer (LC) patients. Five channels were used in immunofluorescent staining, including leukocyte marker CD45 (red), epithelial CTC marker CK (green), mesenchymal CTC markers N-cadherin (N-cad, cyan) and vimentin (Vim, magenta), and nucleus marker DAPI (blue). White blood cells were identified as CD45+/CK−/N-cad−/Vim−/DAPI+, while CTCs were identified as either CK+/CD45−/DAPI+ (epithelial positive), or N-cad+/Vim+/CD45−/DAPI+ (mesenchymal positive), or CK+/N-cad+/Vim+/CD45−/DAPI+ (both epithelial and mesenchymal positive). Scale bar: 10 μm.

FIG. 2.5B is a graph illustrating quantitative analysis of the effective diameter (maximum feret diameter of cells from their bright field images) of individual CTCs and WBCs enriched from 3 lung cancer patients' samples. Randomly selected CTCs from these patients revealed a high polydispersity of cell sizes. CTCs from patient 1 (NSCLC, stage IV, LC-P1-Opt) had diameters of 9.73±3.11 μm (n=39; mean±s.d.; smallest 4.59 μm; largest 18.52 μm); CTCs from patient 2 (SCLC, stage IV, LC-P2-Opt) had diameters of 10.98±3.41 μm (n=43; mean±s.d.; smallest 5.61 μm; largest 21.13 μm); CTCs from patient 3 (SCLC, stage IV, LC-P3-Opt) had diameter of 9.23±3.67 μm (n=59; mean±s.d.; smallest 4.55 μm; largest 21.67 μm). WBCs from 3 lung cancer patients had diameter of 10.58±2.27 μm (n=74; mean±s.d.; smallest 6.86 μm; largest 16.83 μm) FIG. 2.5C illustrates analysis of surface antigens expression of individual CTCs from 3 lung cancer patients' samples revealed a high heterogeneity of epithelial and mesenchymal characteristics in these cells. Cells from each patient are grouped into three categories (columns): epithelial positive (E+: CK+/CD45−/DAPI+), mesenchymal positive (M+: N-cad+/Vim+/CD45−/DAPI+), both epithelial and mesenchymal positive (E+/M+: CK+/N-cad+/Vim+/CD45−/DAPI+). Numbers in each column indicate the absolute number of cells in each category. For LC-P1-Opt, 11.84% of CTCs was epithelial positive, 78.95% of CTCs was mesenchymal positive, and 9.21% was both epithelial and mesenchymal positive. For LC-P2-Opt, 46.04% of CTCs was epithelial positive, 50.99% of CTCs was mesenchymal positive, and 2.97% was both epithelial and mesenchymal positive. For LC-P3-Opt, 27.93% of CTCs was epithelial positive, 61.71% of CTCs was mesenchymal positive, and 10.36% was both epithelial and mesenchymal positive.

FIGS. 2.6A-2.6G illustrate correlation between clinical stages, growth rates of CTC culture, Oncotype Dx scores and heterogeneity of CTC surface antigen expressions in early stage breast cancer patients (third cohort, n=6) FIG. 2.6A represents bright field and immunofluorescent images of 3 representative CTCs and 1 WBC enriched from breast cancer patients. Cells were subjected to multiplexed immunofluorescence assessment with cell-type specific markers detected with distinct wavelength channels, including leukocyte marker CD45 (blue), epithelial CTC marker EpCAM (green), mesenchymal CTC marker vimentin (Vim, red). White blood cells were identified as CD45+/EpCAM−/Vim−, while CTCs were identified as EpCAM+/Vim−/CD45− (epithelial positive), EpCAM−/Vim+/CD45− (mesenchymal positive), or EpCAM+/Vim+/CD45− (both epithelial and mesenchymal positive). Scale bar: 10 μm. FIG. 2.6B is a graph illustrating relative counts of CTC subtypes by surface antigen expression from 6 breast cancer patients' samples. Cells from each patient are grouped into three categories (columns): epithelial positive (E+: EpCAM+/Vim−/CD45−), mesenchymal positive (M+: EpCAM−/Vim+/CD45−), both epithelial and mesenchymal positive (E+/M+: EpCAM+/Vim+/CD45−). Numbers in each column indicate the absolute number of cells in each category. FIG. 2.6C illustrates proportional components of CTC profiles for breast cancer patients, Oncotype Dx scoring indicated for each patient. Scores for P2, P3 and P4 patients are not available because their clinical stages are either too high (*confirmed metastasis) or too low (**non-invasive carcinoma/DCIS). FIG. 2.6D is a graph illustrating the average proportional components of CTC subtypes are shown with respect to clinical staging. FIG. 2.6E are representative images of primary cell culture of iFCS device output over a 72-hour period. NCCN staging for each BrC patient is represented next to the patient designation. Scale bar: 200 μm. FIG. 2.6F is a graph illustrating combined total number of cells quantified from primary cell culture imaging for each BrC patient at 0 hours and the change in counts at 72 hours. FIG. 2.6G illustrates growth rate of cells in primary culture for each BrC patient ((cell number at 72 hr−cell number at 0 hr)/cell number at 72 hr).

FIGS. 3.1A-3.1B illustrate magnetic content of cells at various stages in an embodiment of a device of the present disclosure. FIG. 3.1A illustrates magnetic content of undeflected (left) and deflected (right) white blood cells (WBCs) at stage I. FIG. 3.1B illustrates magnetic content of undeflected (left) and deflected (right) WBCs at stage II.

FIG. 3.2 is a graph illustrating the average number of Dynabeads per white blood cell (WBC) after cell enrichment. The device carried over on average 533±34 WBCs per 1 milliliter of blood processed. Much of the carryover was derived from WBCs that were either not labeled or labeled with just one magnetic bead.

FIG. 3.3 illustrates the size distribution of clinical CTCs from non-small cell lung cancer (NSCLC) patients, small cell lung cancer (SCLC) patients, and breast cancer (BrC) patients. Details are listed in Table 2.4.

FIG. 3.4 are images of cytopathological staining of spiked HCC1806 cancer cells after enrichment. Scale bars: 20 μm.

FIG. 3.5A shows bright field and immunofluorescent images of CTCs enriched from breast cancer patient. Five channels were used in immunofluorescent staining, including leukocyte marker CD45 (red), epithelial CTC marker EpCAM (green), mesenchymal CTC markers N-cadherin (N-cad, cyan) and vimentin (Vim, magenta), and nucleus marker DAPI (blue). FIG. 3.5B illustrate bright field and immunofluorescent images of CTC enriched from lung cancer patients. Five channels were used in immunofluorescent staining, including leukocyte marker CD45 (red), epithelial CTC marker CK (green), mesenchymal CTC markers N-cadherin (N-cad, cyan) and vimentin (Vim, magenta), and nucleus marker DAPI (blue). Scale bars: 10 μm.

FIGS. 3.6A-3.6C illustrate correlation of the numbers of each CTC subtype with tumor grade in third cancer patient cohort.

FIG. 3.7A illustrates magnetization of the as-synthesized ferrofluid. Solid lines are the fitting of the experimental date to the Langevin function. Saturation magnetization of this ferrofluid was 0.104 kA m$^{-1}$, corresponding to a 0.028% volume fraction or concentration. FIG. 3.7B is a rheological plot of the ferrofluid. The viscosity of ferrofluid was measured to be 0.99 mPa·s. FIG. 3.7C is a transmission electron microscopy (TEM) image of the maghemite nanoparticles. Scale bar: 10 nm.

FIG. 3.8 is a schematic illustration of a magnet array according to an embodiment of multi-stage microfluidic device of the present disclosure showing orientation of the magnet array relative to a first separation stage and second separation stage of the device.

DETAILED DESCRIPTION

In various aspects, microfluidic devices and methods of using microfluidic devices are provided for separating and/or enriching circulating tumor cells (CTCs) in a biological sample such as whole blood. The methods do not involve labeling of the CTCs and are capable of high throughputs with high levels of retention and separation of the circulating tumor cells.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Embodiments of the present disclosure will employ, unless otherwise indicated, techniques of biochemistry, molecular biology, microfluidics, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Although any methods and materials similar or equivalent to those described herein can also be used in the practice or testing of the present disclosure, the preferred methods and materials are now described. Functions or constructions well-known in the art may not be described in detail for brevity and/or clarity.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims.

The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" indicates that the subsequently described event or circumstance can or cannot occur, and that the description includes instances where said event or circumstance occurs and instances where it does not.

As used herein, "kit" refers to a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" refers to documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

A "biocompatible" substance or fluid, as described herein, indicates that the substance or fluid does not adversely affect the short-term viability or long-term proliferation of a target cell within a particular time range.

Microfluidic Devices & Systems and Methods of Use Thereof

In various aspects, microfluidic devices, systems, kits, and methods of using multi-stage microfluidic devices are provided for high throughput sorting, separation, and/or enrichment of circulating tumor cells (CTCs) and other unlabeled rare cells in a biological sample such as blood, where the CTCs or other rare cells do not need to be labeled.

Although microfluidics-based methods have been explored as a new avenue to enrich and study CTCs for the past decade, previous approaches were based on the use of specific tumor antigens (marker-dependent) or cell size threshold (cell size-dependent) for enrichment, and suffered disadvantages due to limitations of these approaches. For example, marker-dependent methods that relied on EpCAM or other combination of tumor cell surface antigens were rendered ineffective due to inherent heterogeneity of tumor subtypes. The significant difference among various markers and their expression levels in CTCs undergoing EMT was difficult to predict, resulting in incomplete recovery of CTCs from clinical samples. Cell size-dependent methods, on the other hand, based on a presumed size difference between blood and cancer cells, proved largely ineffective because a significant percentage of CTCs in circulation were comparable or smaller than blood cells. Measurements of white blood cells (WBCs) and cultured cancer cells revealed that there was a significant size overlap between the two, and an appreciable percentage (e.g., ~35% for DMS 79 and H69 small cell lung cancer cell lines) of cancer cells were smaller than ~10 μm. In addition, clinically isolated CTCs were reported to be as small as ~6 μm. As a result, few cell size-dependent methods could achieve complete recovery and low WBC contamination simultaneously. Furthermore, due to their fragile nature, CTCs need to be processed with gentle enrichment conditions to keep their viability and tumorigenic capability for downstream studies. Thus, new devices and methods are needed that can enrich viable CTCs regardless of their surface antigens and size profiles.

In some aspects, a multi-stage microfluidic device is provided for enriching CTCs in a biological sample. The device can include at least three stages, although there may be more in some embodiments. Therefore, the terms first, second, third and so-on, when used to describe the stages, should not be considered limiting on the total number of stages but is used for simplicity to describe the relative ordering of the stages. Additional stages, not explicitly described, may in some aspects appear before the first stage.

Embodiments of the present disclosure include a cell separation system and/or kit for enriching CTCs in a biological sample. In embodiments, the cell separation system/kit can include a plurality of magnetic micro beads adapted for conjugation to white blood cells in the biological sample and not to the CTCs, a biocompatible superparamagnetic sheathing fluid or composition including a plurality of magnetic nanoparticles, and a multi-stage microfluidic device for magnetically separating the CTCs from the biological sample. The systems/devices of the present disclosure allow enrichment of CTCs are size independent and do not require labeling the CTCs.

In embodiments the plurality of magnetic microbeads can include various biocompatible magnetic materials, such as, but not limited to iron oxide based magnetic material (e.g., magnetite ($Fe_3O_4$), maghemite ($Fe_2O_3$), or combinations of these. The magnetic materials for the microbeads should be non-toxic to cells. The magnetic microbeads of the present disclosure are adapted for conjugation with white blood cells (WBCs) such that the microbeads bind/conjugate with WBCs in the sample and do not substantially bind/associate with the CTCs in the sample (e.g., they do not specifically bind/conjugate/associate with the CTCs or other components present in the sample other than WBC's, and any non-specific association with CTCs, if present, is insignificant/negligible). In embodiments the magnetic microbeads are functionalized for specific binding to WBCs, such as by surface-functionalization with one or more binding agent(s) for specific binding to WBCs but that will not substantially bind the CTCs (e.g., streptavidin/avidin conjugated to biotinylated white blood cell-specific antibodies). In embodiments the magnetic microbeads comprise streptavidin coated magnetic Dynabeads (Life Technologies, Carlsbad, Calif.). In embodiments, the streptavidin coated magnetic beads are further conjugated to white-blood cell specific antibodies for specific binding to white blood cells. Examples of white blood cell-specific antibodies include, but are not limited to anti-CD45, anti-CD66b and anti-CD16, and combinations thereof (while other antibodies can be used, a combination of the above antibodies will target substantially all WBC's present in a blood sample).

In embodiments, the biological sample is whole blood. In embodiments, the sample is whole blood that has been treated with a lysis buffer to lyse/remove red blood cells. In embodiments, the biological sample is combined with the magnetic microbeads prior to introduction to the device of the present disclosure to produce a magnetically labeled biological sample, such that the WBCs in the sample are substantially conjugated to magnetic microbeads prior to introduction. In embodiments, about 95% to 99.9%, or more of the white blood cells are conjugated to one or more magnetic microbeads. In embodiments, a majority of white blood cells in the magnetically labeled sample are conjugated to about 1 or more magnetic microbeads. In embodiments, a majority of white blood cells in the magnetically labeled sample are conjugated to about 1 to about 60 magnetic microbeads. In embodiments, the white blood cells in the magnetically labeled sample are conjugated to an average of about 20-50 magnetic microbeads. As used herein, the terms "magnetically labeled biological sample" and "magnetically labeled sample" refer to embodiments described above where a biological sample is combined with magnetic microbeads adapted for specific conjugation with WBC's and not to CTC's or other components of the sample, which are not substantially associated with the magnetic microbeads or otherwise magnetically labeled. Thus the terms "magnetically labeled biological sample" and "magnetically labeled sample" should not be interpreted to indicate any magnetic labeling of any other components of the biological sample other than the WBCs.

In embodiments, the biocompatible superparamagnetic sheathing fluid (also periodically referred to herein as a "ferrofluid") of the present disclosure is a colloidal suspension of magnetic nanoparticles, coated by a biocompatible surfactant and suspended in a carrier fluid. The ferrofluid of the present disclosure is biocompatible and non-toxic to CTCs. In embodiments, the magnetic nanoparticles are a non-toxic magnetic material, such as, but not limited to iron oxide materials (e.g., magnetite ($Fe_3O_4$), maghemite ($Fe_2O_3$), and combinations of these. In embodiments, the magnetic nanoparticles are iron oxide particles (e.g., maghemite ($Fe_2O_3$)). Materials such as iron, cobalt, cobalt ferrite, and FePt are potentially toxic to cells, but could potentially be used if first rendered biocompatible/nontoxic by biocompatible coatings, etc. The magnetic nanoparticles can have a diameter of about 1-20 nm. In embodiments they have an average diameter of about 8-12 nm (e.g., about 11 nm). In embodiments, the magnetic nanoparticles are coated in a biocompatible surfactant to reduce agglomeration and to increase biocompatibility. In embodiments, the biocompatible surfactant can include electric double layer surfactant, polymer surfactant, inorganic surfactant, or a combination thereof. In embodiments, the surfactant is polymethyl methacrylate-polyethylene glycol (PMMA-PEG). In embodiments, the carrier medium can include biocompatible carrier fluids, such as, but not limited to, water, salt solution, or a combination. In embodiments, the carrier medium is a balanced salt solution, such as Hank's balanced salt solution (HBSS). In an embodiment, the biocompatible superparamagnetic sheathing fluid includes maghemite nanoparticles ($Fe_2O_3$) coated with polymethyl methacrylate-polyethylene glycol (PMMA-PEG) and 10% (v/v) 10× Hank's balanced salt solution (HBSS). In embodiments, the pH is about 7, and the osmotic pressure is close to that of a biological (e.g., human) cell. In embodiments, the ferrofluid concentration (volume fraction of magnetic particles) is about 0.01% to 0.04% and intervening ranges. For instance, in embodiments the ferrofluid concentration can be about 0.024 to 0.033% (v/v). In embodiments the concentration is about 0.028%. The viscosity of the biocompatible superparamagnetic sheathing fluid varies based on the concentration of magnetic particles, the surfactant chosen, as well as the carrier fluid. In embodiments, the viscosity of the ferrofluid is about 0.95 mPa·s to 1.1 mPa·s. In embodiments of systems or kits of the present disclosure, the kit/system may include the fully prepared biocompatible superparamagnetic sheathing fluid as described above, and/or a prepared biocompatible superparamagnetic sheathing fluid along with instructions for diluting the fluid with additional carrier fluid to adjust the concentration/volume fraction of magnetic nanoparticles in the sheathing fluid. In embodiments, systems or kits of the present disclosure may include a biocompatible superparamagnetic sheathing composition that includes the plurality of magnetic nanoparticles and instructions for combining the magnetic nanoparticles/biocompatible superparamagnetic sheathing composition with a biocompatible surfactant and biocompatible carrier fluid to make a biocompatible superparamagnetic sheathing fluid of the present disclosure. In embodiments, systems/kits of the present disclosure can include the plurality of magnetic nanoparticles and the biocompatible surfactant (separately or mixed (e.g., such that the surfactant coats the magnetic nanoparticles) and instructions for combining the biocompatible superparamagnetic sheathing composition with a biocompatible carrier fluid to make a biocompatible superparamagnetic sheathing fluid of the present disclosure.

The multi-stage microfluidic devices of the present disclosure are adapted for use with the biocompatible superparamagnetic sheathing fluids and the magnetic microbeads for enrichment of CTCs from a biological sample. Embodiments of the multi-stage microfluidic devices include a filter section, a first separation stage, and a second separation stage (in description of embodiments of the device in parts of the present disclosure, these three sections may also be referred to as a first, second, and third stage).

In embodiments of multi-stage microfluidic devices of the present disclosure the filter section can include a first microfluidic channel, a first fluid inlet, and one or more filters along a length of the first microfluidic channel. The first fluid inlet is configured to receive the biological sample, where the biological sample has been combined with the magnetic microbeads prior to introduction to the multi-stage microfluidic device such that a majority of the white blood cells in the biological sample are conjugated to one or more magnetic microbeads. This can be referred to as the magnetically labeled sample and/or magnetically conjugated biological sample. In embodiments, the one or more filters are configured to remove a first plurality of waste particles from the biological sample (e.g., large particulate/agglomerated matter in the sample). After the first filter section, the filtered biological sample proceeds to the first separation stage.

In embodiments of multi-stage microfluidic devices of the present disclosure the first separation stage includes a second microfluidic channel fluidly connected to the first microfluidic channel and having a second fluid inlet to receive the biocompatible superparamagnetic sheathing fluid at a first end, and a first fluid outlet at a second end. In such embodiments, the second microfluidic channel is configured to combine the magnetically labeled biological sample from the first filter section with the biocompatible superparamagnetic sheathing fluid from the second fluid inlet. It is also contemplated that, in embodiments, the biocompatible superparamagnetic sheathing fluid can be combined with the biological sample and the magnetic microbeads prior to introduction to the device instead of introduced after the filter stage via a second fluid inlet. Thus, in embodiments, the first separation stage may not include a second fluid inlet. In other embodiments, a second fluid inlet may be located in the filter section before or after the filters. The first separation stage is fluidly connected to the second separation stage. The second separation stage includes a third microfluidic channel fluidly connected to the second microfluidic channel and having a second fluid outlet and at least a first and second circulating tumor cell outlet.

The multi-stage microfluidic devices of the present disclosure also include one or more magnetic sources adjacent to the multi-stage microfluidic device. The magnetic source(s) are configured to produce a non-uniform magnetic field along the second microfluidic channel. The magnetic field distribution is non-uniform along one or more dimensions (e.g., length, width, and/or height) of the second microfluidic channel. In embodiments, magnetic source(s) are configured to produce a non-uniform magnetic field along the length, width, and/or height of the second microfluidic channel. In embodiments, the magnetic field has a component sufficiently perpendicular to the length of the second microfluidic channel to cause a plurality of white blood cells conjugated to the magnetic beads to be deflected into the first fluid outlet. The non-uniform magnetic field also focuses the CTCs (which are not magnetically labeled) away from the first fluid outlet and toward the second separation stage/third microfluidic channel. The magnetic source(s) are also configured to produce a substantially symmetric magnetic field along the third microfluidic channel, where the substantially symmetric magnetic field has a field maximum along a length of the third microfluidic channel sufficient to cause the white blood cells conjugated to the magnetic beads in the third microfluidic channel to be focused toward a center of the third microfluidic channel and to exit the channel via the second fluid outlet and to cause circulating tumor cells to be deflected towards an outer portion of the third microfluidic channel and to exit the channel via the first and/or second circulating tumor cell outlet.

In embodiments, the multi-stage microfluidic device has a serpentine shape. In embodiments, the filter section has a first end and a second end fluidly connected by the first microfluidic channel, where the first fluid inlet is fluidly connected to the first microfluidic channel at the first end, and the one or more filters are located between the first and second end of the first microfluidic channel. In embodiments, the first separation stage has a third end and fourth end fluidly connected by the second microfluidic channel, where the third end is connected to the second end of the first microfluidic channel of the filter section by a first u-shaped channel, where the second fluid inlet is fluidly connected to the second microfluidic channel at the third end and the first fluid outlet is fluidly connected to the second microfluidic channel at the fourth end. In embodiments, the second separation stage has a fifth end and a sixth end fluidly connected by the third microfluidic channel, where the fifth end is connected to the fourth end of the second microfluidic channel of the first separation stage by a second u-shaped channel, where the second fluid outlet is fluidly connected to the third microfluidic channel at the sixth end and configured to receive materials flowing through a central portion of the third microfluidic channel. In embodiments, the first and second circulating tumor cell outlets are each fluidly connected to the third microfluidic channel at the sixth end and offset from the center of the channel and configured to receive material flowing near the outer portion of the channel. In embodiments the first and second u-shaped channels located between the first filter section and the first separation stage and between the first separation stage and second separation stage, respectively, provide the serpentine shape to the multi-stage microfluidic device. As used herein, "u-shaped" indicates a general u-shape but which may have a variety of configurations (e.g., rounded, squared, or even angular). In embodiments the U-shape channel has an angle of curvature of about 120° to about 180°.

In embodiments of the microfluidic device of the present disclosure, the first fluid outlet is offset from a central diameter of the second microfluidic channel and configured to receive white blood cells conjugated to magnetic beads and unconjugated magnetic beads flowing on one side of the second microfluidic channel (e.g., due to deflection from the non-uniform magnetic field produced by the one or more magnetic sources).

In embodiments, the magnetic source is a magnet or magnetic array. In embodiments, the magnetic source is a first magnet array and a second magnet array arranged in a quadrupole configuration such that the first magnet array and the second magnet array are oriented to repel each other, one embodiment of which is illustrated in FIG. 3.8. In embodiments, the second separation stage (e.g., third stage) is sandwiched between the first magnet array and the second magnet array and oriented such that the length of the third microfluidic channel is centrally aligned between the first magnet array and the second magnet array. In embodiments, the magnetic source is located about 800 to 1200 µm from the third microfluidic channel. In embodiments, one magnetic array is about 800-1200 µm from the top of the third microfluidic channel (second separation stage), and the second magnetic array is about 1000 µm from the bottom of the third microfluidic channel. In embodiments, the second microfluidic channel of the first separation stage (e.g., second stage) is offset from the magnetic source such that the magnetic source provides a non-uniform magnetic field. In embodiments, the magnetic source is the same first and second magnet array arranged in a quadrupole configuration sandwiching the third microfluidic channel, but the second microfluidic channel runs along a side of the magnetic array, such that the second microfluidic channel is not centrally aligned between the first and second magnet array. In embodiments, the second and third microfluidic channels are substantially parallel; thus there is the same distance above and below the channels from the magnetic source as set forth above for the third microfluidic channel e.g., 800-1200 µm), yet the lateral distance of the magnets from the center of the second microfluidic channel is greater as illustrated in FIG. 3.8.

In embodiments of the microfluidic device of the present disclosure, the one or more magnetic sources produce a flux density of about 0.3-0.8 T (e.g., 0.4 to 0.6 T) in the first separation stage and about 1-1.8 T (e.g., 1.3 to 1.5 T) in the second separation stage. In embodiments, the one or more magnetic sources produce a flux density gradient that ranges from about 4 to 256 T m-1 in the first separation stage and from about 0-625 T m-1 in the second separation stage, wherein the flux density gradient is lower towards the center of the third microfluidic channel of the second separation stage than at the outer portion, such that the magnetically conjugated WBC's are deflected toward the second fluid outlet.

In embodiments, one or more of the first microfluidic channel, the second microfluidic channel, and the third microfluidic channel have a thickness of about 100 µm to about 500 µm. In embodiments, the thickness of the microfluidic channels can range from about 100 µm to 500 µm, etc. In embodiments the thickness of the channel is about 300 µm.

In embodiments, the second microfluidic channel has a width of about 500 µm to 5000 µm, about 1200 µm to 2000 µm, about 1400 µm to 1800 µm, or about 1600 µm, and the third microfluidic channel has a width of about 500 µm to 5000 µm, about 800 µm to 1600 µm, about 1000 µm to 1400 µm, or about 1200 µm. In embodiments, the second microfluidic channel has an optimized width of about 1600 µm, and the third microfluidic channel has an optimized width of about 1200 µm. The widths of the second and third microfluidic channels was optimized based on a combination of operating parameters, including magnetic flux density, operational flow rates, concentration of the superparamagnetic fluid, and the like. In embodiments, the microfluidic channels can have a length of about of 52000-57000 µm.

In embodiments, the second microfluidic channel has an optimized length of 55000 µm, with an acceptable range of 52000-57000 µm, and the third microfluidic channel has an optimized length of 55000 µm, with an acceptable range of 52000-57000 µm.

In embodiments of the microfluidic device of the present disclosure, the circulating tumor cells that exit via the first and/or second circulating tumor cell outlet comprise about 95% or more, 97%, or more, or 99% or more of the total number of circulating tumor cells present in the biological sample inserted into the first fluid inlet when in operation.

The present disclosure also includes methods of using the microfluidic devices of the present disclosure and the systems of the present disclosure (e.g., microfluidic device plus biocompatible superparamagnetic sheathing fluid and magnetic microbeads) to enrich CTCs in a biological sample. In some aspects, the methods are capable of isolating a majority of the unlabeled rare cells. In some aspects, the unlabeled rare cells are circulating tumor cells in a whole blood sample, and the majority of the circulating tumor cells comprises about 90%, about 95%, about 97%, about 99%, or more of the circulating tumor cells as compared to a total number of circulating tumor cells present in the biological sample inserted into the first fluid inlet when in operation.

In some aspects, the biological sample includes whole blood, wherein the whole blood includes a plurality of components. In some aspects, the plurality of components comprises magnetically labelled white blood cells, and wherein at least 95%, at least 98%, at least 99%, at least 99.9%, or more of the white blood cells are not collected in the one or more circulating tumor cell outlets as compared to a total number of white blood cells present in the whole blood inserted into the first fluid inlet when in operation. This can mean, for instance, that at least 95%, at least 98%, at least 99%, at least 99.9%, or more of the white blood cells are collected in one or more of the filters, the first fluid outlet, and the second fluid outlet as compared to a total number of white blood cells present in the whole blood inserted into the first fluid inlet when in operation. This can result in, for example, that at least 90%, 92%, 95%, or more of the unlabeled rare cells are collected in the one or more circulating tumor cell outlets as compared to a total number of unlabeled rare cells present in the whole blood inserted into the first fluid inlet when in operation.

Methods are provided for enriching, separating, or isolating unlabeled rare cells such as circulating tumor cells from a sample, e.g. a biological sample such as whole blood. In some aspects, the biological sample is or includes whole blood. In some embodiments the biological sample includes whole blood treated with a lysis buffer to lyse red blood cells as described above. In some aspects, the biological sample includes about 1 to 1000 circulating tumor cells per milliliter of the biological sample, including both natural samples and samples spiked with CTCs for research purposes. In embodiments, the biological sample comprises about 1-10 circulating tumor cells per milliliter of the biological sample. Examples of the circulating tumor cells can include those selected from the group consisting of a primary cancer cell, a lung cancer cell, a prostate cancer cell, a breast cancer cell, a pancreatic cancer cell, and a combination thereof.

The methods can include enriching circulating tumor cells in a sample of whole blood, wherein the whole blood includes unlabeled rare cells and white blood cells, the method including: (i) adding a plurality of magnetic beads to the sample to produce sample having magnetically labeled WBCs, wherein at least some of the white blood cells are associated with the magnetic beads; (ii) filtering the magnetically labeled sample in a microfluidic device to produce a filtered sample by removing large cell debris from the magnetically labeled sample; (iii) separating at least a portion of the white blood cells that are associated with the magnetic beads by flowing the filtered sample through a sheath flow in a nonuniform magnetic field to produce a first enriched sample; and (iv) isolating a majority of the unlabeled rare cells by magnetic flow focusing the first enriched sample in a microfluidic channel.

In embodiments, methods of enriching CTCs in a biological sample of the present disclosure include combining the biological sample (e.g., a sample from a biological host; e.g., a sample having a plurality of components) with a plurality of magnetic microbeads adapted to conjugate to white bloods cells such that a majority of white blood cells in the sample become conjugated to at least one magnetic microbead and then introducing the magnetically labeled biological sample (including the magnetic microbeads and magnetic microbead-conjugated WBCs) into the first fluid inlet of a microfluidic device and combining the magnetically labeled biological sample with a biologically compatible superparamagnetic fluid, introduced via the second fluid inlet, wherein the magnetically labeled sample and the superparamagnetic fluid are introduced at a flow rate sufficient to cause the biological sample to flow along the first microfluidic channel, the second microfluidic channel, and the third microfluidic channel such that a majority of the magnetic microbeads and white blood cells are deflected to the first or second fluid outlet and a majority of the circulating tumor cells from the biological sample are collected in the one or more circulating tumor cell outlets.

In embodiments, the biological sample is a sample from an animal host (e.g., a mammal, human, etc.). In embodiments, the biological sample is a fluid having a plurality of components (e.g., cells, fluids, etc.) (e.g., blood, urine, saliva, exudate, homogenized tissue in a biocompatible fluid, etc.). In embodiments, the biological sample is from a human. In embodiments, the biological sample is whole blood or whole blood that has been treated with lysis buffer to lyse red blood cells. In embodiments, the biological sample is whole blood, or RBC lysed blood from a human host having cancer or suspected of having cancer.

In embodiments of methods of the present disclosure, the flow rate of the fluids/samples (e.g., the magnetically labeled biological sample, the combined magnetically labeled sample and superparamagnetic fluid, etc.) in the microfluidic device is about 10-400 microliters per minute, or any intervening range. In embodiments, the flow rate is 10-250 microliters per minute. In some embodiments, the flow rate is about 0.6 to 24 milliliters of the fluids per hour, and intervening ranges, e.g., about 0.6 to 15 ml/hr.

Untreated biological samples have various amounts of circulating tumor cells, dependent on the type of cancer, the stage of cancer, other cancer treatments, etc. In general, un-spiked samples from a host have about 1-10 circulating tumor cells/ml of the biological sample. However, for research purposes, sometimes samples are spiked with additional CTCs. Also the level of CTCs can be higher depending on the tumor grade of a host. Thus, in embodiments, the biological sample can have from about 1 to about 1000 circulating tumor cells/ml of biological sample. It will be understood that for research purposes even higher amounts of circulating tumor cells may be present in a sample and still be within the scope of the present disclosure. However, unlike some previous methods, the present methods/devices/systems are able to detect/enrich CTCs from a sample having 10 or fewer CTCs/ml of biological sample.

In embodiments, the CTCs can include, but are not limited to, a primary cancer cell, a lung cancer cell, a prostate cancer cell, a breast cancer cell, a pancreatic cancer cell, and a combination thereof.

Methods of the present disclosure for enriching CTCs in a sample of whole blood (or RBC-lysed whole blood), where the whole blood comprises unlabeled rare cells and white blood cells, include adding a plurality of magnetic beads to the sample to produce a magnetically labeled sample, where a majority of the white blood cells are associated with the magnetic beads and wherein the magnetic beads do not conjugate to the unlabeled rare cells; filtering the magnetically labeled sample in a microfluidic device to produce a filtered sample by removing large cell debris from the magnetically labeled sample; separating at least a portion of the white blood cells that are associated with the magnetic beads by flowing the filtered sample through a sheath flow in a biocompatible superparamagnetic sheathing fluid in a nonuniform magnetic field to produce a first enriched sample; and then isolating a majority of the unlabeled rare cells by flowing the first enriched sample through a channel with a substantially symmetric focused magnetic field such that a majority of any remaining white blood cells associated with the magnetic beads are focused towards a center of the channel and to a central channel outlet and the majority of the unlabeled rare cells are collected from one or more peripheral channel outlets.

The methods can include introducing the biological sample/magnetically labeled biological sample, which is preferably combined with the biocompatible magnetic microbeads prior to introduction, into the first fluid inlet of a microfluidic device described herein at a flow rate sufficient to cause the biological sample to flow along the microfluidic channel(s) of the device such that a majority of the circulating tumor cells from the biological sample are collected in the one or more circulating tumor cell outlets. In embodiments the magnetically labeled biological sample can also be combined with the superparmagentic fluid prior to introduction into the device. The methods can include introducing a biocompatible ferrofluid, which may include mixing the biological sample with the ferrofluid in the device as well as the use of the ferrofluid as a sheathing fluid flow in the operation of the device.

The methods are devices are capable of high throughput. In some aspects, the throughput is about 6 milliliters to about 25 milliliters of the biological sample per hour. In some aspects, the flow rate is about the flow rate is about 10 μL to about 600 μL per minute.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: iFCS Technology and Device (Medium Magnetic Field Gradient, One-Stage, Sheath-Free)

Circulating tumor cells (CTCs) contains abundant information regarding the location, type and stage of cancer and have significant implications in both diagnostic target and guiding personalized treatment. The traditional isolation technologies rely on the properties of CTCs such as antigens (e.g., epithelial cell adhesion molecule or EpCAM) or size to separate them from blood. Integrated—ferrohydrodynamic cell separation (iFCS), a size-independent and marker-independent method, can isolate cancer cells with large size distribution in biocompatible ferrofluids with a throughput 6 mL h$^{-1}$, an average recovery rate of 97.9%, and an 99.95% WBC depletion. We performed systematic parametric studies of key factors influencing the performance of iFCS and determined parameters for high-throughput, high recovery rate and high purity CTC separation. We then tested and validated the performance of the method with cancer cells from 8 cultured cancer cell lines and 3 different types of cancer. The mean recovery rate of non-small cancer cells from RBC-lysed blood using this technology was 98.7%. This method was also validated with small lung cancer cells and the mean recovery rate was 95.5%.

Integrated Ferrohydrodynamic Cell Separation (iFCS) Working Principle

In the case of label-based magnetophoresis (FIG. 1.1A), magnetization of the particles $\vec{M}_p$ is larger than the surrounding fluid medium $\vec{M}_f$, therefore the magnetic force will point toward magnetic field maxima (FIG. 1.1A). On the other hand, for label-free negative magnetophoresis, magnetization of the diamagnetic particles $\vec{M}_P$ is smaller than the surrounding ferrofluid medium $\vec{M}_f$, therefore the magnetic force will point toward magnetic field minima (FIG. 1.1B). Integrated ferrohydrodynamic cell separation (iFCS) scheme integrates both label-based magnetophoresis and label-free negative magnetophoresis in a single device (FIGS. 1.1D and 1.1E) under non-uniform magnetic field. Particles and/or cells of magnetization larger than surrounding medium and smaller than surrounding medium will move in different direction in the device, as shown in FIGS. 1.1C and 1.1F, resulting in separation of particles and/or cells based on their relative magnetization to the fluid medium.

Simulation and Calibration with Microbeads

In order to test the validity of working principle, we compared simulated trajectories of microbeads with experimental ones that were obtained from imaging 15.0-μm-diameter non-magnetic beads (NMB) and 11.8-μm-diameter magnetic beads (MB) in an iFCS device. From the trajectories, we calculated the deflection in the y-direction, denoted as Y, and separation distance between the two types of beads, denoted as ΔY. The simulation results were carried out using different parameters including throughput (10-600 μL min$^{-1}$), ferrofluid concentration (0-1.0%, v/v) and magnetic field gradient (20-280 T m$^{-1}$). The goal here was to optimize the separation of non-magnetic beads from magnetic beads, which translated to maximizing both Y and ΔY simultaneously. Experimental conditions for calibration were the same as those in simulation. We extracted Y and ΔY at the end of the channel and used them to compare simulation and experimental results.

We first optimized the throughput of the device. Both simulation and experimental results (FIG. 1.2A) showed a monotonically decreasing trend for ΔY as the throughput increased. Both simulation (FIG. 1.2D) and experimental results (FIG. 1.2G) indicated widely distributed trajectories for 11.8 μm magnetic bead, and completely deflected trajectories for 15.0 μm non-magnetic beads at high flow rate. The second parameter we optimized was ferrofluid concentration. In general, a higher ferrofluid concentration resulted large magnetic force on non-magnetic beads, leading to a larger deflection in the y-direction. However, the Y value of magnetic beads (magnetic content is 0.737% v/v in this case) decreased as ferrofluid concentration increased, and increased when the concentration was larger than 0.737% (FIGS. 1.2E and 1.2H), resulting a smaller separation distance ΔY (FIG. 1.2B). It should be noted that a portion of magnetic beads were trapped at the bottom of channel when ferrofluid concentration was low. The last parameter that we chose to optimize was magnetic field gradient, whose value changed as we adjusted the distance between the magnet and the channel. FIGS. 1.2C and 1.2F showed that, in both simulation and calibration, when the magnetic field gradient increased, the overall deflection Y for both beads increased too. This is because the magnetic force on beads was determined in part by the gradient. The larger the field gradient, the larger the magnetic force. On the other hand, the separation distance decreased when the gradient was too weak to deflect beads. As a result, we chose a field gradient of 132 T m$^{-1}$ for following experiments.

To achieve high throughput, recovery rate and purity, we chose a throughput of 100 μL min$^{-1}$, ferrofluid concentration of 0.049% (v/v) and magnetic field gradient of 132 T m$^{-1}$. With optimized parameters, we run a series of experiments with 20.3 and 8.0 μm (red fluorescent) non-magnetic beads and 11.8 μm (yellow fluorescent) magnetic beads. All the beads are randomly distributed near the inlet. Without magnetic field, there are no separation (FIG. 1.3D) and they start to deflect under the non-uniform magnetic field (FIG. 1.3E). Non-magnetic beads were collected from outlet 1, as shown in FIGS. 1.3C and 1.3E. on the other hand, magnetic beads were collected from outlet 2 and 3, as shown in FIG. 1.3F.

Verification of iFCS for High-Throughput and High-Recovery Spiked Cancer Cells Separation.

In order to show the size-independent characteristic of iFCS device, we measured the size of cancer cell lines before separation. The size distributions of various cancer cell lines and white blood cells are presented in FIG. 1.4A. There is large size overlap between cancer cell lines and white blood cells (WBCs), which was the main challenge in existing label-free cancer cell separation methods. For example, the minimum size of PC-3 cell line was measured to be around 8 μm. This makes it challenging to enrich small PC-3 cancer cells from WBCs, because they have overlapping sizes (FIG. 1.4A).

In addition, we measured the number of dynabeads on each labeled WBC (n=1000). Human whole blood was obtained from healthy donors according to a protocol approved by Institutional Review Board (IRB) at University of Georgia. Calculated the amount of biotinylated antibody and magnetic beads required based on the WBC count. Used 100 fg/WBC for anti-CD45, anti-CD16 (BioLegend, San Diego, Calif.), and anti-CD66b (Life Technologies, Carlsbad, Calif.). Each WBC were labeled with 125 magnetic beads (Dynabeads Myone streptavidin T1, Life Technologies, Carlsbad, Calif.). Dynabeads were washed twice with 0.01% TWEEN 20 in PBS, then washed with 0.1% BSA in PBS and resuspended in PBS. The whole blood was firstly labeled with antibodies for 30 min and lysed by RBC lysis buffer (eBioscience, San Diego, Calif.) for 7 min at room temperature. Cell mixtures were centrifuged for 5 min at 800×g and the pellet were suspended in PBS with Dynabeads. Incubate the tube for 25 min on the rocker. Added ferrofluid and 0.1% (v/v) Pluronic F-68 non-ionic surfactant (Thermo Fisher Scientific, Waltham, Mass.) to achieve the same volume with whole blood and keep mixing for 5 more minutes. The number of dynabeads on each WBC were counted with microscope and the average was 34±11 dynabeads per WBC (FIG. 1.4B). The magnetic content in dynabeads was 11.5% (v/v). Based on the size of WBCs and the number of labeled dynabeads, we calculated the magnetic content in each WBC (FIG. 1.4C). About 99.5% of WBCs had magnetic content larger than 0.05% (v/v). Under optimized experimental conditions (throughput=100 μL min$^{-1}$, ferrofluid concentration=0.049%, and field gradient=132 T m$^{-1}$), we collected about 99% spiked cancer cells and remove >99.5% WBCs.

We performed a series of experiments with spiked cancer cells of cultured cell lines and WBCs based on optimal parameters. We first studied the performance of iFCS using spiked PC-3 prostate cancers in WBCs. The concentration of DAPI stained WBCs, labeled with dynabeads, was 1×10$^6$ cells mL$^{-1}$; CTCs were simulated by spiking ~1×10$^4$ Cell-Tracker Green stained PC-3 cancer cells into 1 mL of WBCs. FIG. 1.5A indicated that all the cells were randomly distributed at the inlet of the device, then started to deflect when they entered the magnetic field region and were completely separated at the outlets. PC-3 cells collected from collection outlet had polydisperse sizes, as shown in FIG. 1.5B. To future validate the size-independent characteristics of iFCS, we repeated the experiments with MCF-7 and MDA-MB-231 cancer cells under the same conditions. The size distributions of each cell line were extremely similar before and after iFCS processing (FIG. 1.5C, Table 1.1). WBCs collected from collection outlet were also identified by counting the number of dynabeads on their surface (FIG. 1.5D). The average number of dynabeads per WBC increased as the ferrofluid concentration increased.

TABLE 1.1

Statistics about spiked and collected cancer cells under optimized experimental conditions.

| Cancer cell line | Minimum diameter (spiked, μm) | Minimum cell diameter (collected, μm) | average diameter (spiked, μm) | average diameter (collected, μm) |
|---|---|---|---|---|
| MCF-7 | 7.0 | 6.6 | 17.5 ± 4.3 | 18.8 ± 5.3 |
| MDA-MB-231 | 7.0 | 7.0 | 19.1 ± 3.6 | 19.9 ± 4.6 |
| PC-3 | 8.1 | 6.6 | 19.9 ± 4.6 | 20.4 ± 4.9 |

We characterized the iFCS device with 6 types of cancer cells under optimized conditions with ~100 cell mL$^{-1}$ spike ratio. As shown in FIG. 1.5E and Table 1.2, the average recovery rates of 97.9±1.0%, 97.6±1.0%, 98.8±1.4%, 99.4±0.6%, 98.7±0.6%, and 99.7±0.6% were achieved for MCF-7, MDA-MB-231, HCC1806, H1299, H3122 and, PC-3 cell lines, respectively. The corresponding purities of separated cancer cells for each cell line were 22.0±1.3% (MCF-7), 23.5±0.7% (MDA-MB-231), 25.2±1.5% (HCC1806), 23.1±0.9% (H1299), 22.2±0.9 (H3122), and 23.3±0.4 (PC-3), confirming the robustness of the iFCS device for cancer cell separation. We further validated the device with small lung cancer cells. The average recovery rates of 95.0±1.2% and 95.9±1.3% were achieved for DMS79 and H69 cell lines, respectively. A series of spike-in experiment, in which a certain number PC-3 cells (100, 250, 500, 1000, 2000) and 1 million WBCs were spiked into 1 mL ferrofluid, were carried out to validate that the device has the potential to process clinically relevant blood samples (FIG. 1.5F). An average recovery rate of 98.8% was achieved in the iFCS for this particular prostate cancer cell line.

TABLE 1.2

Cancer cell separation under optimized conditions. ~100 cancer cells and 1 × 10$^6$ WBCs were spiked into 1 mL of ferrofluid with concentration of 0.049% (v/v). The recovery rate was defined as the ratio of the number of cancer cells collected from outlet 1 over the total number of spiked cancer cells from all outlets. The purity was defined as the number of identified cancer cells over the total number of cells (WBCs + cancer cells) from outlet 1. Data are expressed as mean ± standard deviation (s.d.), n = 3.

| Cancer cell line | Cancer cell type | Measured minimum diameter (μm) | Measured Average diameter (μm) | No. of spiked cancer cells | No. of cancer cells (outlet 1) | No. of cells (outlet 2 & 3) | Recovery rate | No. of WBCs | Purity |
|---|---|---|---|---|---|---|---|---|---|
| MCF-7 | Breast | 7.0 | 17.5 | 110 ± 9 | 108 ± 8 | 2 ± 1 | 97.9 ± 1.0 | 384 ± 2 | 22.0 ± 1.3 |
| MDA-MB-231 | Breast | 7.0 | 19.1 | 110 ± 7 | 108 ± 7 | 3 ± 1 | 97.6 ± 1.0 | 354 ± 6 | 23.5 ± 0.7 |
| HCC1806 | Breast | 6.7 | 15.4 | 109 ± 4 | 108 ± 5 | 1 ± 2 | 98.8 ± 1.4 | 324 ± 6 | 25.2 ± 1.5 |
| H1299 | Lung | 7.2 | 20.4 | 101 ± 4 | 100 ± 3 | 1 ± 1 | 99.4 ± 0.6 | 336 ± 4 | 23.1 ± 0.9 |
| H3122 | Lung | 6.7 | 17.7 | 104 ± 3 | 103 ± 3 | 1 ± 1 | 98.7 ± 0.6 | 360 ± 2 | 22.2 ± 0.9 |
| DMS79 | Lung | 3.2 | 12.8 | 118 ± 12 | 112 ± 10 | 6 ± 2 | 95.0 ± 1.2 | 350 ± 4 | 24.2 ± 1.7 |
| H69 | Lung | 4.0 | 11.2 | 106 ± 4 | 102 ± 4 | 4 ± 1 | 95.9 ± 1.3 | 366 ± 7 | 21.7 ± 0.8 |
| PC-3 | Prostate | 8.1 | 19.4 | 99 ± 3 | 99 ± 3 | 0 ± 1 | 99.7 ± 0.6 | 324 ± 1 | 23.3 ± 0.4 |

Example 2: iFCS Technology and Device (High Magnetic Field Gradient, Multiple-Stage, Sheath-Flow)

In this device, we have developed a marker-independent and size-independent integrated ferrohydrodynamic cell separation (iFCS) method, which is biocompatible and could enrich entire rare circulating tumor cells (CTCs) from patient blood with a high throughput and a high recovery rate. The blood samples suspended in ferrofluids (0.03% v/v) are injected into the inlet A and focused by sheath flow through inlet B (ferrofluids with a concentration of 0.03% v/v). The majority of labeled white blood cells (WBCs) and free Dynabeads are depleted into the waste outlet 1 in stage 2. The unlabeled cells and some labeled WBCs, including CTCs, enter the stage 3. The CTCs are then continuously deflected to the two sides of the channel and labeled WBCs and free beads are focused in the center of the channel, as shown in FIGS. 1.6A-1.6C.

The magnet holder consists of top and bottom parts and is secured with screws and nuts. Two magnet arrays repelling each other are placed in the top and bottom holders, respectively. The microfluidic device is sandwiched between the magnet holders and the center of the stage 3's channel is exactly aligned with the center of the magnet arrays (FIGS. 1.6A-1.6C and FIG. 1.7). CTCs enrichment is achieved by inputting red blood cell (RBC)-lysed blood that is pre-labeled with magnetic beads (Dynabeads MyOne Streptavidin T1) targeting WBCs via CD45, CD16 and CD66B surface antigens (FIG. 1.8). We will refer this multiple stage device as FCSv2.

We performed systematic optimization of this method and determined parameters in the microfluidic device that achieved an average recovery rate of 99.16% using 8 different cell lines (HCC1806, HCC70, MCF7, MDA-MB-231, H1299, H3122, DMS79, and H69) from RBC-lysed WBCs, which were labeled with Dynabeads conjugated with leukocyte antibodies. The developed device is able to process 12 mL of blood within one hour. The device achieved an average WBC carryover of 527 WBCs per mL of input blood. Specifically, for each cell line at ~100 cells per mL spike ratio, the recovery rates of cancer cells were 98.46±0.50% (HCC1806 breast cancer), 99.68±0.46% (HCC70 breast cancer), 99.05±0.75% (MCF7 breast cancer), 99.35±0.46% (MDA-MB-231 breast cancer), 99.40±0.85% (H1299 non-small cell lung cancer), 99.13±0.49% (H3122 non-small cell lung cancer), 99.11±1.25% (DMS79 small cell lung cancer), and 99.11±0.74% (H69 small cell lung cancer). To validate that the device has the potential to process clinically relevant blood samples, a series of spike-in experiments in which a certain number of HCC70 breast cancer cells (20, 50, 100, and 200) are spiked into 1 mL of WBCs. As shown in FIGS. 1.9A-1.9B, an average recovery rate of 99.08% is achieved in the FCSv2 device. FIGS. 1.10A-1.10B show the separation of spiked cancer cells (stained with CellTrack Green) at the end of stages 2 and 3.

Example 3: Optimized iFCS System

Introduction

Isolation of circulating tumor cells (CTCs) from blood provides a minimally-invasive alternative into the basic understanding, diagnosis and prognosis of metastatic cancers. The roles and clinical values of CTCs are under intensive investigation, yet most studies are limited by technical challenges in the comprehensive enrichment of intact and viable CTCs with minimal white blood cells contamination. The present example describes a novel, optimized system and method based on contrast of cell magnetization, termed as integrated ferrohydrodynamic cell separation (iFCS), that enriches CTCs in a tumor antigen-independent and cell size variation-inclusive manner, and achieves high-throughput (12 mL h$^{-1}$), high recovery rate (99.16% at down to ~10 cells mL$^{-1}$ spike ratio), low WBC contamination (~500 cells for every one milliliter blood processed) and is biocompatible. This method allows for studies on subtypes of CTCs, and their correlations with clinical and diagnostic variables in small cohorts of cancer patients.

Insights on heterogeneity among circulating tumor cells (CTCs) have significant implications for basic and translational research of metastatic cancer that is responsible for over 90% of cancer related mortality. 1-4 While primary tumor characterization is the most common source of material to predict tumorigenesis, clinically relevant findings would include the ability to predict whether the tumor will likely metastasize and establish lethal colonies of tumors in distal organ sites. Due to inherent heterogeneous composition of primary tumors, needle-biopsies and surgical samples may miss key diagnostic markers that would define metastatic potential of the tumor. Characterizing blood borne circulating tumor cells provides a window into metastasis research as tumor cells are in route to their new niche, where these cells represent disease potential of the tumors to establish multiple sites. 3•4 Hence, CTCs could be a more representative sample of tumor disease potential than a primary tumor biopsy, including a compendium of genetic changes that increase metastatic potential over the course of tumor evolution. Development of innovative technologies that will allow the enrichment and characterization of a complete repertoire of viable CTCs could increase our understanding of metastasis and may lead to novel applications including the creation of in vitro and ex vivo models to experimentally manipulate and screen panels of patient derived tumors.

Three concurrent technical challenges in existing CTC enrichment methods, including the dependence of specific tumor antigens for tumor cell recognition, inability to account for the variation of tumor cell sizes in isolation, and difficulty of keeping CTCs viable and intact for downstream analysis, complicated the study and applications of CTCs. These issues are worsened by the fact that CTCs are extremely rare, estimated at less than 10 tumor cells in every one-milliliter of whole blood. Past studies have showed that CTCs isolated by the US Food and Drug Administration (FDA) approved CellSearch system, identified by epithelial cell adhesion molecules (EpCAM) alone, were associated with poor prognosis in metastatic and localized carcinomas in clinical trials.5-7 However, increasingly CTCs were found to be a rare and heterogeneous population of different phenotypic subtypes,1•8 in which a fraction of original epithelial tumor cells could transition into stem-like mesenchymal cells in a metamorphosis noted as EMT, Epithelial to Mesenchymal Transition.3 This transition may be what gives CTCs the traits of high motility, invasiveness and limitless potential to create a new tumor site, therefore cells that have gone through this transition could possess the greatest threat of metastasis and short-term recurrence.3•4•9 Given the importance of EMT CTCs, the influence of mesenchymal properties on the prolonged survival of CTCs in the circulation, and on their capacity to form metastatic tumors, new methods are urgently needed to allow for a comprehensive enrichment and analysis of viable CTCs.

Microfluidics-based methods have provided a new avenue to enrich and study CTCs for the past decade but were often biased because of the use of specific tumor antigens or cell size threshold in enrichment. Majority of microfluidic methods operated based on either marker-dependent or cell size-dependent principles.10 For example, marker-dependent methods that relied on EpCAM or other combination of tumor cell surface antigens were rendered ineffective due to inherent heterogeneity of tumor subtypes.11 The significant difference among various markers and their expression levels in CTCs undergoing EMT was difficult to predict, resulting in incomplete recovery of CTCs from clinical samples. On the other hand, cell size-dependent methods including those based on filtration,12 dean flow and vortex chip,13•14 depleted blood cells and recovered CTCs that were larger than ~10 μm in diameter, based on a presumed size difference between blood and cancer cells.10 The issue of these methods was that a significant percentage of CTCs in circulation were comparable or smaller than blood cells. Our measurements of white blood cells (WBCs) and cultured cancer cells revealed that there was a significant size overlap between the two, and an appreciable percentage (e.g., ~35% for DMS 79 and H69 small cell lung cancer cell lines) of cancer cells were smaller than ~10 μm. In addition, clinically isolated CTCs were reported to be as small as ~6 μm.15 As a result, few cell size-dependent methods could achieve complete recovery and low WBC contamination simultaneously.10•16 Furthermore, CTCs are fragile and need to be processed with gentle enrichment conditions to keep their viability and tumorigenic capability for downstream studies. In summary, the inherent bias in tumor antigen-dependent and cell size-dependent methods, and the recognition that CTCs are highly rare, heterogeneous and fragile, highlight the need to develop new methods that can enrich viable CTCs regardless of their surface antigen and size profiles.

The device/system developed and described in the present Example addressed the above-mentioned challenges through the development of a novel CTC enrichment method that is based on contrast of magnetic properties of cells, termed as integrated ferrohydrodynamic cell separation (iFCS). This method is tumor antigen-independent and cell size variation-inclusive; it allows for simultaneous depletion of WBCs and enrichment of viable CTCs, resulting in complete recovery of intact and viable CTCs with minimal WBC contamination that were suitable for clinical applications. In developing this method, we performed systematic parametric studies of key factors influencing the performance of iFCS and determined parameters for high-throughput (12 mL h$^{-1}$), high recovery rate (99.16% at down to ~10 cells mL$^{-1}$ spike ratio), low WBC contamination (~500 cells for every one milliliter blood processed) and biocompatible enrichment (cell viability of 97.69±0.70% after enrichment) of CTCs from the blood of cancer patients. iFCS was first validated with cancer cells from 8 cultured cell lines of 3 different types of cancer. Mean recovery rate of cancer cells from red blood cell (RBC)-lysed blood using this method was 99.16%. The prototype iFCS device carried over on average 533±34 WBCs per 1 mL of blood processed. Enriched cancer cells had excellent short-term viability, and intact capability to proliferate to confluence. Clinically, iFCS was first used to study cell size variation and surface antigen expression heterogeneity of CTCs enriched from 3 breast cancer patients and 3 lung cancer patients. This study revealed a high degree of variation in CTC sizes. 55.4% of patient derived CTCs possessed an effective diameter of less than 10 μm, and there was a significant overlap in sizes between CTCs and WBCs. The study also showed heterogeneity of epithelial and mesenchymal characteristics in patient CTCs' surface antigen expression. These results highlighted the need for tumor antigen-independent and cell size variation-inclusive methods such as iFCS. We also used iFCS at a remote site (Henry Ford Health System, Detroit, Mich.) to investigate whether variable counts of CTC subtypes would correlate with clinical and diagnostic variables. We found, within a small cohort (n=6) of early stage breast cancer patients, that mesenchymal and EMT subtypes of CTCs had a higher correlation to tumor grade than epithelial subtype.

Methods

Model of iFCS and its validation. We developed an analytical model used in this study to simulate cell trajectories in three-dimensional (3D) manner.18, 19 It could predict 3D transport of diamagnetic cancer cells and magnetic WBCs in ferrofluids inside a microfluidic channel coupled with permanent magnets. The magnets produced a spatially non-uniform magnetic field that led to a magnetic force on the cells. Trajectories of the cells in the device were obtained by (1) calculating the 3D magnetic force via an experimentally verified and analytical distribution of magnetic fields as well as their gradients, together with a nonlinear Langevin magnetization model of the ferrofluid and (2) solving governing equations of motion using analytical expressions of magnetic force and hydrodynamic viscous drag force in MATLAB (Math Works Inc., Natick, Mass.).

Synthesis and characterization of ferrofluids. Maghemite nanoparticles (10.91±4.86 nm) were synthesized by a chemical co-precipitation method as previously described.19 Size and morphology of maghemite nanoparticles were characterized via transmission electron microscopy (TEM; FEI, Eindhoven, the Netherlands). Magnetic properties of the ferrofluid were measured at room temperature using a vibrating sample magnetometer (VSM; MicroSense, Lowell, Mass.). The viscosity of ferrofluids was characterized with a compact rheometer (Anton Paar, Ashland, Va.) at room temperature. Ferrofluid characterization data are illustrated in FIGS. 3.7A-3.7C.

Cell culture and sample preparation. Cancer cell lines (ATCC, Manassas, Va.) including four breast cancer cell lines (HCC1806, HCC70, MCF7 and MDA-MB-231), two NSCLC cell lines (H1299 and H3122), two SCLC cell lines (DMS79 and H69), and one prostate cancer cell line (PC-3) were used in this study. Cell lines were cultured following manufacturer's recommended protocol. Cancer cells were fluorescently stained with CellTracker Green (Life Technologies, Carlsbad, Calif.) before each use. Cells were counted with a Nageotte counting chamber (Hausser Scientific, Horsham, Pa.) to determine the exact number of cells per μL. Desired cancer cells (10, 25, 50, 100 or 200) were spiked into 1 mL of labeled WBCs.

Ferrofluid biocompatibility. Short-term cell viability after iFCS was examined using a Live/Dead assay (Life Technologies, Carlsbad, Calif.). For long-term proliferation, separated HCC1806 cells from an iFCS device were washed three times with culture medium to remove the nanoparticles, and then the cells were suspended in culture medium and seeded into a T25 flask. Cells were then cultured at 37° C. under a humidified atmosphere of 5% CO2. Cellular morphology was inspected every 24 hours.

iFCS device fabrication and assembly. Microfluidic devices were made of polydimethylsiloxane (PDMS) using standard soft lithography techniques. The thickness of the microfluidic channel was measured to be 300 μm by a profilometer (Veeco Instruments, Chadds Ford, Pa.). Device was placed within a custom aluminum manifold that held four NdFeB permanent magnets (K&J Magnetics, Pipersville, Pa.) in a quadrupole configuration. Each magnet was 50.8 mm in length, 6.35 mm in both width and thickness, and had a remanent magnetization of 1.48 T.

Microfluidic experiment setup and procedure. During a typical experiment, a microfluidic device inserted within manifold was placed on the stage of an inverted microscope (Axio Observer, Carl Zeiss, Germany) for observation and recording. Two fluid inputs were controlled by individual syringe pumps (Chemyx, Stafford, Tex.). Blood samples were injected into an inlet of an iFCS device, sheath flow of ferrofluids was injected into a second inlet. Images and videos of cells were recorded with a CCD camera (Carl Zeiss, Germany). After enrichment, cells were collected in a 15-mL centrifuge tube with complete culture media. Fabricated devices were flushed by 70% ethanol for 10 minutes and then primed with 1× phosphate-buffered saline (PBS) supplemented with 0.5% (w/v) bovine serum albumin (BSA) and 2 mM EDTA (Thermo Fisher Scientific, Waltham, Mass.) for 10 minutes before each use.

Patient recruitment and sample processing. Healthy human blood samples were obtained from Clinical and Translational Research Unit of University of Georgia with informed consents according to a protocol approved by Institutional Review Board (IRB) (University of Georgia, STUDY00005431). Healthy donor samples were used for spike-in experiments with cell lines. Cancer patient samples collected at University Cancer and Blood Center (Athens, Ga.) was approved by the IRB (University of Georgia, STUDY00005431) before study initiation and informed consent was obtained from the participants. Cancer patient samples collected at Henry Ford Health System (Detroit, Mich.) was approved by the IRB (Henry Ford Health System, Davis-11564) before study initiation and informed consent was obtained from the participants. All blood samples were collected into either vacutainer K2-EDTA tubes (BD, Franklin Lakes, N.J.) or cell-free DNA BCT (Streck, Omaha, Nebr.) and were processed within 2 hours of blood draw. Detailed patient information and CTC enumeration was listed in Table 2.5. Complete blood count (CBC) reports were obtained to determine the number of WBCs. Whole blood was labeled with leukocyte-specific biotinylated antibodies including anti-CD45 (eBioscience, San Diego, Calif.), anti-CD16 (eBioscience, San Diego, Calif.), and anti-CD66b (BioLegend, San Diego, Calif.) for 30 min. The antibody conjugated blood was lysed by RBC lysis buffer (eBioscience, San Diego, Calif.) for 10 minutes at room temperature. Blood cells were then incubated with streptavidin coated magnetic Dynabeads (Life Technologies, Carlsbad, Calif.) for 30 minutes on a rocker. All the labeling and washing procedures were followed by manufacturer's recommended protocol. Blood cells were finally suspended in the same volume of ferrofluid (0.028% v/v) containing 0.1% (v/v) Pluronic F-68 non-ionic surfactant (Thermo Fisher Scientific, Waltham, Mass.) before processing.

CTC identification. After processing of blood with an iFCS device, cells were immobilized onto a poly-1-lysine coated glass slide with a customized cell collection chamber. The collected cells were fixed with 4% (w/v) paraformaldehyde for 10 minutes and subsequently permeabilized with 0.1% (v/v) Triton X-100 in PBS for 10 minutes. Cells were then blocked with blocking reagent (Santa Cruz Biotechnology, Dallas, Tex.) for 30 minutes. After blocking non-specific binding sites, cells were immunostained with primary antibodies including anti-cytokeratin (CK3-6H5)-FITC (Miltenyi Biotec, Auburn, Calif.) or EpCAM (EBA-1)-Alexa Fluor 488 (Santa Cruz Biotechnology, Dallas, Tex.), Vimentin (V9)-Alexa Fluor 647 (Santa Cruz Biotechnology, Dallas, Tex.), and N-cadherin (13A9)-Alexa Fluor 594. Nuclei were counterstained with DAPI. All samples were also stained with anti-CD45 (H130)-PE (BD Biosciences, San Jose, Calif.) to identify leukocytes. After immunofluorescence staining, cells were washed with PBS and coverslipped with mounting medium for imaging or stored at 4° C.

CTC culture. Primary cells from patient blood after processing with iFCS device were centrifuged at 200×g for 5 minutes at 37° C. and resuspended in RPMI-1640 media with 15% fetal bovine serum (FBS). Cells were cultured in vented T-25 cm2 flask at 37° C. with 5% CO2. Primary cell growth rate was determined over a 72-hour period.

Results

Overview of iFCS.

Integrated ferrohydrodynamic cell separation (iFCS) method uses the following strategy to achieve tumor antigen-independent and cell size variation-inclusive enrichment of viable CTCs and simultaneous depletion of contaminating WBCs, leaving intact CTCs at its device's output with minimal WBC carryover. In this strategy, virtually all WBCs are rendered magnetic by labeling them with magnetic microbeads through a combination of leukocyte biomarkers, while CTCs remain unlabeled. WBC-bead conjugates and CTCs continuously flow through a microfluidic device filled with ferrofluids, a colloidal suspension of magnetic nanoparticles with tunable particle concentration. Magnetization of the ferrofluid $M_{fluid}$, under an external magnetic field, is adjusted to be less than that of WBC-bead conjugates $M_{WBC-bead}$, so that unlabeled CTCs with a close to zero magnetization $M_{CTC}$, regardless of their sizes, are pushed towards a magnetic field minima due to a phenomenon known as "diamagnetophoresis" (FIG. 2.1A, top),17 while WBC-bead conjugates are attracted to a magnetic field maxima through a competition between both "magnetophoresis" and "diamagnetophoresis" (FIG. 2.1A, bottom), and continuously depleted. The strategy integrates both "diamagnetophoresis" and "magnetophoresis" in ferrofluids to enrich the entire repertoire of CTCs from blood regardless of CTCs' surface antigen profile and size profile.

The iFCS-based CTC enrichment strategy relies on the establishment of both "magnetophoresis" and "diamagnetophoresis" of cells immersed in ferrofluids. A magnetic force is generated on magnetic or diamagnetic cells under a non-uniform magnetic field,17

$$\vec{F}_{mag} = \mu_0 V_{cell}[(\vec{M}_{cell} - \vec{M}_{fluid}) \cdot \nabla]\vec{H} \qquad (1)$$

where $\mu_0 = 4\pi \times 10^{-7}$ H m$^{-1}$ is the permeability of free space, $V_{cell}$ is the volume of the cell, $\vec{M}_{cell}$ is its magnetization, $\vec{M}_{fluid}$ is magnetization of the ferrofluid surrounding the cell, and $\vec{H}$ is magnetic field strength at the center of the cell. For cells in ferrofluids under a magnetic field, magnitudes of the magnetization of the cell $M_{cell}$ and the ferrofluid $M_{fluid}$ with superparamagnetic particles in it can be modeled via a Langevin function. From Eq. 1, we learn that the magnetic force directs cells to either a magnetic field maxima or minima depending on the contrast between cell and fluid magnetizations, i.e., the sign of the term $\vec{M}_{cell} - \vec{M}_{fluid}$, and the magnitude of the force is also proportional to the volume of the cells $V_{cell}$.

FIGS. 2.1A-2.1D illustrate the design of a prototype iFCS microfluidic device based on the above principle. We incorporated two enrichment stages in prototype devices, in order to prevent magnetic microbead aggregation due to the use of large number of magnetic beads. Prior to device processing, WBCs in blood were labeled with magnetic microbeads through leukocyte surface biomarkers so that overall magnetization of the WBC-bead conjugates $M_{WBC\text{-}bead}$ was larger than its surrounding ferrofluid medium $M_{fluid}$. Magnetization of the unlabeled CTCs $M_{CTC}$ was close to zero and less than its surrounding ferrofluids $M_{fluid}$. In the first stage (FIG. 2.1B, top), a magnetic field was used to direct unlabeled and sheath-focused CTCs to remain at the upper boundary of a microchannel, while attract unbound magnetic beads and WBCs labeled with ≥3 microbeads towards a waste outlet. This way, a significant percentage of beads and WBCs were depleted before the second stage, so that bead aggregation was minimized (FIG. 3.1A). In the second stage, a symmetric magnetic field with its maximum at the middle of the channel was used to attract remaining WBC-bead conjugates towards to the channel center for fast depletion, while unlabeled CTCs flowing along the upper and lower channel boundaries were collected for analysis at the end of the channel (FIG. 3.1B). This design aimed to enrich all CTCs regardless of their surface antigens and sizes, at the same time remove virtually all WBCs from collection outlets. An example of an arrangement of magnetic sources (in this case, a magnetic array) relative to the first and second separation stages of an exemplary device is illustrated in FIG. 3.8.

A physical model was developed to optimize the prototype device for practical CTC enrichment. CTCs are extremely rare in the blood circulation and hidden among millions of WBCs with similar size. The rate of CTC occurrence was reported to be <10 cells in one milliliter of blood.10•16 In order to optimize iFCS method and objectively evaluate its performance, four metrics were used, including cell-processing throughput, CTC recovery rate, WBC contamination and integrity of enriched cells, which were consistent with reports of existing methods (see Table 2.1). For iFCS, the parameters that affected these four metrics include device geometry, magnetic field and its gradient, magnetic bead labeling efficiency of WBCs, flow rate of cells, and ferrofluid properties. These parameters were coupled and optimized systematically. We created such a model that could predict three-dimensional (3D) trajectories of cells in laminar flow conditions inside the device.18•19 Both magnetic force and hydrodynamic drag force were taken into consideration in simulating the cell trajectories.

Optimization of iFCS for CTC Enrichment.

We optimized iFCS for tumor antigen-independent and cell size variation-inclusive enrichment of CTCs, with a goal of enriching the entire repertoire of viable CTCs with minimal WBC contamination. In quantitative terms, the performance goals for iFCS devices included: (1) a complete CTC recovery rate of >99% at clinically relevant occurrence rate for CTCs (1-10 cells mL$^{-1}$), regardless of their surface antigens and sizes; (2) a minimal WBC contamination of ~500 cells at the device output for every one milliliter blood processed, (3) a blood processing throughput of more than 10 mL h$^{-1}$, and (4) unaffected cell integrity after enrichment, including viability and proliferation. These metrics were chosen as targets after a survey of existing microfluidic CTC enrichment methods (see Table 2.1).

Systematic optimization of iFCS devices focused on the effects of device geometry, magnetic microbeads functionalized per WBC, magnetic field and its gradient, flow rates, as well as ferrofluid concentration on device performance, including throughput, recovery rate and WBC contamination. Firstly, we determined microchannel dimensions for both stages by balancing a clinical goal of processing at least 10 milliliters of blood within one hour, and a goal to maintain laminar flow in the device. Final channel dimensions (first stage: 55×1.6×0.3 mm; second stage: 55×1.2×0.3 mm; L×W×H) were optimized so that the Reynold's number was on the order of 10 when cell flow rate was 12 mL h$^{-1}$, ensuring laminar flow condition and physiologically equivalent shear rates (first stage average: 270.8 s$^{-1}$, range: 63.4-510.4 s$^{-1}$; second stage average: 190.8 s$^{-1}$; range: 54.4-360.5 s$^{-1}$) during CTC enrichment.20 The prototype microchannel and assembled device are shown in FIGS. 2.1C and 2.1D. Secondly, the amplitude of magnetic force on cells is proportional to the amplitude of magnetic field gradient. In order to maximize field gradient, we adopted a quadrupole magnet configuration in the iFCS device that could generate magnetic flux density in the range of 0.5-1.5 T, and magnetic flux density gradient up to 625 T m$^{-1}$ (FIG. 2.2A). Thirdly, number of magnetic microbeads functionalized onto WBCs should be maximized to increase the contrast between WBC-bead conjugates and surrounding ferrofluids. Therefore, we optimized a WBC functionalization protocol by using a combination of three leukocyte surface biomarkers. Streptavidin-coated Dynabeads (1.05 μm, 11.4% Fe$_2$O$_3$ volume fraction) and biotinylated anti-human CD45, CD15 and CD66b antibodies combination were used. Results in FIG. 2.2B show that with antibody and bead concentrations (CD45: 100 fg/WBC, CD15: 75 fg/WBC, CD66b: 75 fg/WBC, magnetic beads: 125/WBC), WBCs were conjugated with 34±11 beads, and >99.9% of WBCs were labeled. Average magnetic content volume fraction of WBCs from bead conjugation was 0.36%, with a minimal value of 0.026%, corresponding to WBCs that were labeled with just one magnetic bead. By choosing a ferrofluid concentration that was in the vicinity of the minimal value of WBCs' magnetic content volume fraction, it became possible to deplete virtually all WBCs.

The remaining optimization focused on the effect of ferrofluid concentration and cell-processing throughput on the performance metrics in the second stage. For this part of optimization, we calculated two outputs—a deflection in the y-direction for cells (see FIG. 2.2A for coordinates), denoted as Y, and a separation distance between WBCs and CTCs, denoted as ΔY. Both outputs were optimized using parameters including ferrofluid concentration (0-0.04% v/v) and throughput (0-700 μL min$^{-1}$, i.e., 0-42 mL h$^{-1}$). The goal was to maximize CTC recovery rate and minimize WBC contamination, which translated to maximizing ΔY and cell-processing throughput simultaneously. FIG. 2.2C shows that separation distance ΔY reached a maximum when using a ferrofluid with 0.028% magnetic volume fraction, and largest throughput that could be achieved without compromising CTC recovery was 200 μL min$^{-1}$ (i.e., 12 mL h$^{-1}$).

In summary, the optimization resulted in following operating parameters for the prototype iFCS devices: magnetic flux density in the range of 0.5-1.5 T, and magnetic flux density gradient up to 625 T m$^{-1}$ via assembling four NdFeB permanent magnets in quadrupole configuration; WBCs conjugated with 34±11 magnetic beads, and over 99.9% WBCs labeled; cell-processing throughput 12 mL h$^{-1}$; and ferrofluid concentration 0.028% (v/v). Microchannels in the device had a thickness of 300 μm and a total length of 55 mm, widths of the microchannels for the first and second stages were 1600 μm and 1200 μm, respectively. Using these parameters, we studied via simulation the recovery rate of CTCs (CTC size range: 3-32 μm in spherical diameter)

spiked into WBCs (WBC size range: 5-25 μm in spherical diameter, 34±11 magnetic beads per cell). We chose the smallest diameter of CTCs to be 3 μm, a value that was almost half the size of smallest reported CTCs from clinical samples,15 in order to test the robustness of the tumor antigen-independent and cell size variation-inclusive enrichment method. FIG. 2.2D shows a distribution of cell locations at the end of each stage. In quantitative terms, FIG. 2.2E reports that 96.35% of initial WBCs that were labeled with ≥3 beads and all unbound beads were depleted after just the first stage while all CTCs were persevered, including the smallest 3 μm ones. After the second stage, 3.60% of initial WBCs that were labeled with 2-3 beads were further removed without affecting CTCs. Overall, these two stages together were predicated to be able to deplete 99.95% of WBCs (corresponding to ~500 WBCs contamination or carryover per 1 milliliter blood processed) and preserve 100% of CTCs regardless of their size profile.

Validation of iFCS with Spiked Cancer Cells in Human Blood.

Using optimized device geometry and operating parameters, we studied cancer cell enrichment in iFCS prototype devices using a total of 8 cultured cancer cell lines that have drastically different average cell sizes and polydispersity, including 4 breast cancer cell (BrC) lines, 2 non-small cell lung cancer cell (NSCLC) lines, and 2 small cell lung cancer cell (SCLC) lines. Performance of the enrichment was evaluated on cell-processing throughput, cell recovery rate, WBC contamination/carryover, and integrity of isolated cells. These results were also compared to simulation for test the robustness of the analytical model. A typical enrichment process can be visualized in FIGS. 2.3A and 2.3B, in which ~100 green fluorescently stained HCC1806 breast cancer cells (cell size range 6-47 μm) were spiked into 1 mL of WBCs and processed in an iFCS device at a flow rate of 12 mL h$^{-1}$. In the first stage (FIG. 2.3A, top: phase contrast; bottom: epifluorescence), magnetic force attracted labeled WBCs and unbound beads toward a waste outlet while unlabeled cells including all CTCs and approximately 3.65% of WBCs were continuously flown to the second stage. No aggregation of magnetic beads or ferrofluids was observed within one hour of operation. In the second stage (FIG. 2.3B, top: phase contrast; bottom: epifluorescence), magnetic forces deflected unlabeled cancer cells from the mixture toward both upper and lower collection outlets. Meanwhile, labeled WBCs were focused to the middle channel and depleted through a waste outlet.

We continued by testing recovery rate and WBC carryover at cancer cell occurrence rates that were clinically relevant. The average rate of recovery for HCC70 breast cancer cells was 99.18% at spike ratios between 10-200 (10, 25, 50, 100, and 200) cells mL$^{-1}$ and showed minimal variations among three repeats (FIG. 2.3C), which was consistent with simulation results. After cell enrichment, the device carried over on average 533±34 WBCs per 1 milliliter of blood processed. Much of the carryover was derived from WBCs that were either not labeled or labeled with just one magnetic bead (FIG. 3.2), which was predicted by simulation results. The level of WBC contamination found in iFCS devices was comparable to the monolithic version of the CTC-iChip (~445 WBCs per 1 mL of blood processed), 21 and lower than other recently reported methods, including magnetic ranking cytometry (2000 WBCs mL$^{-1}$) and previous versions of CTC-iChip (1200 WBCs mL$^{-1}$).8•22•23 After successfully demonstrating low-concentration cancer cell enrichment using HCC70 breast cancer (BrC) cell line, we expanded the characterization of recovery rate in iFCS devices with 7 other types of cancer cell lines, including two SCLC cell lines. A measurement on the cell size of these cells lines and WBCs showed that there was a significant size overlap between WBCs and cancer cells, especially the SCLC lines (FIG. 2.3D and Table 2.2). A noticeable percentage of patient CTCs were smaller than 10 μm (55.4%; FIG. 3.3). This would make the enrichment of cancer cells via size-dependent methods ineffective. However, as shown in FIG. 2.3E, by using iFCS method, recovery rates of 98.46±0.50%, 99.05±0.75%, 99.35±0.46%, 99.40±0.85%, 99.13±0.49%, 99.11±1.25%, and 99.11±0.74% were obtained for HCC1806 (BrC), MCF7 (BrC), MDA-MB-231 (BrC), H1299 (NSCLC), H3122 (NSCLC), DMS79 (SCLC), and H69 (SCLC) cell lines, respectively. The average recovery rate across 8 cancer cell lines was 99.16%, which indicated a complete recovery of spiked cancer cells, including even the SCLC cells, regardless of their size profiles. The size distribution of three cells lines before and after enrichment in a single stage version of the iFCS device further confirmed that iFCS could enrich all cancer cells without a loss of small ones (FIG. 2.3F and Table 2.3).

Ferrofluids and the iFCS enrichment process had little impact on cell viability and intactness, given the extremely low ferrofluid concentration (0.028% v/v) and low shear rate in enrichment. We examined short-term cell viability and long-term cell proliferation of cancer cells following the enrichment process. As shown in FIG. 2.3G, cell viability of HCC1806 breast cancer cells before and after enrichment were determined to be 98.30±0.56% and 97.69±0.70%, respectively, indicating a negligible decrease in cell viability before and after the iFCS process. Representative fluorescence images of cells are shown in FIG. 2.3H. We also studied whether enriched cancer cells continued to proliferate normally. FIG. 2.3I shows the images of enriched HCC1806 breast cancer cells on the third day. They were able to proliferate to confluence and maintain the morphology after the iFCS process. Fluorescence image in FIG. 2.3I also confirmed that cells were viable after the 3-day culture. Enriched cells were intact and suitable for immunofluorescent and cytopathological staining (FIG. 2.3J and FIG. 3.4).

Profiling Cell Size and Surface Antigen Heterogeneity Among CTCs in Cancer Patients iFCS devices were capable of enriching CTCs regardless of their cell size variation and surface antigen heterogeneity from clinical samples of breast cancer patients. We investigated whether the heterogeneous population of CTC cell types enriched from iFCS could potentially yield greater clinical utility. For this purpose, we studied two cohorts of cancer patients (breast cancer and lung cancer). We quantified the numbers and sizes of CTCs overall, then defined and quantified CTC subtypes in each patient and found distinct quantities of CTC subtypes within the patient cohort. We categorized the CTC subtypes based on their expression of cell surface markers for epithelial and mesenchymal cell types.

In the first cohort, we used iFCS devices to process blood samples from 3 breast cancer patients who were recruited and consented from University Cancer and Blood Center (Athens, Ga.) under an approved IRB protocol (University of Georgia, STUDY00005431). These patients are identified as breast cancer optimization cohort (BrC-P#-Opt, in which # indicates the number of patient) in this paper. Peripheral blood was collected from the patients before initiation of treatment. Their blood was first lysed to remove RBCs, and then processed with iFCS devices within 2 hours of blood draw. After iFCS enrichment, enriched cells were stained with epithelial marker (EpCAM), mesenchymal markers (vimentin and N-cadherin), leukocyte marker (CD45) as well as nucleus staining DAPI for their identification. CTCs were identified as epithelial positive (EpCAM+/CD45−/DAPI+), mesenchymal positive (Vim+/CD45−/DAPI+, N-cad+/CD45−/DAPI+ or Vim+/N-cad+/CD45−/DAPI+), or both epithelial and mesenchymal positive (EpCAM+/Vim+/N-cad+/CD45−/DAPI+), while WBCs were identified as CK−/Vim−/N-cad−/CD45+/DAPI+. Results from this study are summarized in FIGS. 2.4A-2.4C. Examples of intact CTCs from device outputs are shown in FIG. 2.4A and FIG. 3.5A. We first learned that the effective diameter of CTCs, defined as maximum feret diameter of cells from bright field images, showed a high degree of polydispersity among these enriched cells. For example, patient 1 of this cohort (BrC-P1-Opt) had an advanced stage breast cancer diagnosis (stage IIIA, pre-surgery). We identified 232 CTCs in 9.0 mL of blood (25 CTCs/mL) from this patient. Effective diameters measured from randomly selected cells (n=24) of this patient were 11.99±7.87 μm (mean±s.d.), where the smallest diameter was 4.95 μm and the largest was 33.11 μm (FIG. 2.4B). We characterized surface antigen expressions using above mentioned markers for 232 cells from this patient. The characterization revealed a high degree of heterogeneity of antigen expressions: 12.93% of them was epithelial positive, 78.45% was mesenchymal positive, and 8.62% was both epithelial and mesenchymal positive (FIG. 2.4C). Patient 2 of this cohort (BrC-P2-Opt) had an early stage breast cancer diagnosis (stage IA, post-surgery). 82 CTCs were identified in 12.0 mL of blood (6 CTCs/mL) from this patient. Effective diameters of CTCs (n=26) again showed high polydispersity (mean±s.d.=13.73±6.76 μm, smallest diameter 6.00 μm, and largest diameter 32.10 μm). Surface antigen expressions of cells (n=82) revealed 54.88% was epithelial positive, 30.49% was mesenchymal positive, and 14.63% was both epithelial and mesenchymal positive. Similarly, a third post-surgery patient (BrC-P3-Opt) with a stage IA breast cancer diagnosis exhibited variations in CTCs' size and heterogeneity among antigen expressions.

Overall, we found a variety of CTC subtypes that were positive for either epithelial or mesenchymal factors alone, or cells that were positive for both factors in this cohort (FIG. 2.4A). The cells that were positive for both factors likely represent CTCs that are in transition between Epithelial and Mesenchymal status, indicating their evolution to more virulent tumor cell phenotypes. We found that each patient had a wide range in sizes of CTC's that overlapped with the size distribution of WBC's (FIG. 2.4B). This indicates that existing cell-size dependent methods could greatly decrease the sensitivity of CTC enrichment, by excluding a large proportion of CTCs. Given the proportion of CTC subtypes in each patient, and the corresponding distribution of cell sizes for each patient, a large proportion of the size-excluded CTC's would have been mesenchymal (FIGS. 2.4B and 2.4C). We also observed that the relative numbers of CTC types varied greatly among patients (FIG. 2.4C). For example, "Patient 1" (BrC-P1-Opt) and "Patient 3" (BrC-P3-Opt) carried predominantly mesenchymal CTCs and "Patient 2" (BrC-P2-Opt) carried predominantly epithelial CTCs. In each case, the relative number of transitioning EMT cells (positive for both epithelial and mesenchymal markers) was the least abundant within patient sample counts; however, the relative number of EMT cells significantly varied among patients. We went on to determine if these variable counts of CTC subtypes would correlate with clinical and diagnostic variables in a third cohort at Henry Ford Health System (Detroit, Mich.). Explicitly, we postulated whether the patients with the highest count of either mesenchymal or EMT cells would also have the most aggressive tumor phenotypes. These results will be discussed after next section.

We extended our study to a second cohort including 3 non-surgical stage IV lung cancer patients. They were recruited and consented from University Cancer and Blood Center (Athens, Ga.) under the same IRB protocol (University of Georgia, STUDY00005431). These patients are identified as lung cancer optimization cohort (LC-P#-Opt, in which # indicates the number of patient). Same blood collection, processing and cell identification approaches were used as for breast cancer cohort, except cytokeratin (CK) replaced EpCAM as the epithelial marker. CTCs were identified as epithelial positive (CK+/CD45−/DAPI+), mesenchymal positive (Vim+/CD45−/DAPI+, N-cad+/CD45−/DAPI+, or Vim+/N-cad+/CD45−/DAPI+), or both epithelial and mesenchymal positive (CK+/Vim+/N-cad+/CD45−/DAPI−), while WBCs were identified as CK−/Vim−/N-cad−/CD45+/DAPI+. Results are summarized in FIGS. 2.5A-2.5C with intact CTCs being shown in FIG. 2.5A and FIG. 3.5B. We learned that CTCs from lung cancer patients were highly variable in cell sizes and antigen expressions too. For example, patient 1 of this cohort (LC-P1-Opt) was diagnosed with advanced stage non-small cell lung cancer (stage IV). 228 CTCs were identified in 9.0 mL of blood (25 CTCs/mL). Effective diameters of CTCs (n=39) were 9.73±3.11 μm (mean±s.d.), where the smallest diameter was 4.59 μm and the largest was 18.52 μm. Surface antigen expression characterization of cells (n=228) showed that 11.84% was epithelial positive, 78.95% was mesenchymal positive, and 9.21% was both epithelial and mesenchymal positive. Data on the second patient (LC-P2-Opt, stage IV small cell lung cancer) and the third patient (LC-P3-Opt, stage IV non-small cell lung cancer) were consistent with this observation. The study on both breast cancer and lung cancer patients shows that CTCs from them are highly variable in cell diameters and in most cases their diameters overlap with contaminating WBCs (FIG. 2.4B and FIG. 2.5B). Furthermore, surface antigen expressions of CTCs are non-uniform across cells, making methods relying solely on cell diameter or antigen expression ineffective. iFCS devices, insensitive to both cell size and antigen variations, are able to enrich CTCs and preserve these variations.

Non-EpCAM Positive Type of CTCs Enriched by iFCS Show Better Correlation with Pathological Variables in Early-Stage Breast Cancer Patients.

In the third cohort, we used iFCS devices at Henry Ford Health System (Detroit, Mich.) to process blood samples from 6 breast cancer patients who were recruited and consented there under an approved IRB protocol (Henry Ford Health System, Davis-11564). These patients are identified as breast cancer culture cohort (BrC-P#-Culture, in which # indicates the number of patient). Peripheral blood was collected from the patients before initiation of treatment. Similar blood collection, processing and cell identification approaches were used as in other cohorts. After iFCS enrichment, enriched cells were stained with epithelial marker (EpCAM), mesenchymal markers (vimentin), leukocyte marker (CD45) for their identification. CTCs were identified as epithelial positive (EpCAM+/CD45−), mesenchymal positive (Vim+/CD45−), or both epithelial and mesenchymal positive (EpCAM+/Vim+/CD45−), while WBCs were identified as CD45+. Results from this study are summarized in FIGS. 2.6A-2.6G. When we compared the number of each CTC subtype with clinical-pathology variables we found interesting correlations that suggest the non-EpCAM positive type of CTCs, defined as vimentin-only positive and both EpCAM and vimentin positive, may have better prediction value with regard to prognosis and diagnosis, relative to epithelial (EpCAM-only positive) CTCs. Specifically, when we correlated the numbers of each CTC subtype with tumor grade, we found that EpCAM-only CTCs were the least correlated with this variable ($R^2$=0.025) while mesenchymal cells (vimentin-only CTCs) were significantly more correlated ($R^2$=0.584). Interestingly, the EMT cells had the highest correlation with grade ($R^2$=0.734), suggesting that the presence of these transitioning cells may indicate the invasiveness and aggressiveness of the primary tumor (FIGS. 3.6A-3.6C).

We also investigated how relative CTC subtype counts correspond with standard clinical diagnostic variables. We observed that of the patients with the 21-gene recurrence risk scores (RS), the patient with highest score (BrC-P6-Culture, RS=16) had the highest proportion of mesenchymal only CTCs and also the lowest proportion of EMT CTCs. This may indicate that the relative numbers of cells in transition vs cells that have completely transitioned to mesenchymal status, may be indicative of metastatic potential. Conversely, the patient with the lowest RS score had the highest proportion of epithelial CTCs and the largest proportion of EMT CTCs (FIG. 2.6C). Of all patients with RS values in this cohort, when we compared these with the relative numbers of CTC subtypes, we found no significant correlation with this test. One limitation of this negative finding is that only 3 out of 6 patients had an indication for ordering the 21-gene recurrence test and therefore we could not determine specific correlation of CTC subtypes with great confidence. As an alternative to recurrence risk scores, we investigated whether relative correspondence of CTC subtypes with clinical stages had a better correlation in these patients with recurrence risk estimates. Similar to our 21-gene recurrence test observations, we found that the patient with the highest tumor stage (IIA) also had the highest proportion of mesenchymal-only CTCs and the lowest proportion of epithelial CTCs (FIG. 2.6D). While the limitations of these comparisons preclude statistical significance, there is a compelling trend of specific CTC subtypes correlated with clinical stage and prognosis among the small subset of patients.

Because iFCS allows us to obtain viable cells, we also cultured CTCs for each patient in a pooled-subtype design, as opposed to subclones of specific subtypes. With these cultures, we investigated the relative percentages of the CTC subtypes in each patient culture and measured the growth rate of the cultures over a 72-hour period. We had variable success with culture growth (FIG. 2.6E) and this corresponded to a variable growth rates within cultures that grew significantly (FIG. 2.6F). Of the patient samples that displayed significant growth curves (BrC-P3-Culture, BrC-P4-Culture, and BrC-P5-Culture) we found their growth rate averaged over 60%. When we compared these growth rates with CTC subtype proportions, we found that the two patients with the highest growth curves had the lowest proportion of both epithelial and EMT CTCs, with the highest relative mesenchymal CTCs (of these we successfully established cultures—patient BrC-P6-Culture had the highest mesenchymal proportion but the line was lost to contamination before a growth curve could be calculated). In a preliminary comparison, we observed that growth rates were positively correlated with the relative proportion of mesenchymal cells ($R^2$=0.289), though not significantly.

Discussion

We developed an iFCS method and its prototype devices for tumor antigen-independent and cell size variation-inclusive enrichment of CTCs from cancer patients. After validations with both spike-in samples and clinical samples, the performance of iFCS devices was determined to be: (1) a close-to-complete CTC recovery rate of 99.16% at clinically relevant occurrence rate for CTCs (1-10 cells mL$^{-1}$), regardless of their surface antigens and sizes; (2) a minimal WBC contamination of 533±34 cells at the device output for every one milliliter blood processed, (3) a blood processing throughput of 12 mL h$^{-1}$, and (4) minimally affected cell integrity after enrichment, including viability and proliferation. We compared iFCS performance to a total of 36 recently reported CTC enrichment methods (Table 2.1) and found iFCS had better combinatorial performance metrics in above-mentioned four categories than existing methods. The only published CTC enrichment method with competing performance was CTC-iChip.21-23 The operation of a most recent version of CTC-iChip—monolithic CTC-iChip,21 integrated three working principles including cell size based deterministic lateral displacement (DLD) to deplete red blood cells, inertial focusing to concentrate nucleated cells, and magnetophoretic separation to enrich CTCs. The size based DLD stage risked depleting CTCs smaller than or of similar size as red blood cells. In our iFCS study, we found that on average 34.5% of CTCs (33.1% for NSCLC CTCs, 36.4% for SCLC CTCs, and 34.6% for BrC CTCs) were less than 8 μm (Table 2.4). With other performance metrics (throughput, WBC contamination, and cell integrity) being similar, iFCS could recover a more comprehensive repertoire of CTCs comparing to monolithic CTC-iChip.

We used iFCS devices to investigate whether heterogeneous populations of CTC cell types could potentially yield clinical utility. From first two cohorts of cancer patients (breast and lung cancers), we discovered a variety of CTC subtypes that were positive for epithelial or mesenchymal biomarkers alone, or cells that were positive for both markers. We also discovered that each patient had a high level of CTC size variation, which overlapped with the size distribution of WBCs. This finding highlights the need to develop tumor cell antigen independent and cell size variation inclusive method for CTC studies.

Our third patient cohort—breast cancer cohort in this study are limited to early-stage cancer patients that had no indication of metastatic disease, which inherently allowed us to test whether iFCS devices would yield biomarkers that can be more informative about potential for disease progression and/or undetected metastatic disease, including micrometastasis. The current clinical standard for utilization of CTCs is to rely on epithelial markers to select for tumor cells from the blood cell components. This EpCAM marker selection completely misses a critical component of the heterogenous CTC profile. By harvesting and characterizing the CTC subtype landscape from liquid biopsy, we can develop a clinical application that assesses the 'range' and relative variation in the numbers of mesenchymal cells, which we have currently shown may correlate with clinical prognostic indicators. For instance, with a single liquid blood biopsy, not only could we potentially detect tumor presence but also may be able to predict staging for the solid primary tumor. This level of diagnostics is usually only accomplished by invasive biopsy or surgery. In our assessment of recurrence score correlations with CTC landscapes, certain patients were not given the recurrence risk testing because their staging was deemed too low. However, once we understand the variable landscapes associated with each stage, recurrence estimates can be made more precisely from the sub-population of CTCs that would eventually evolve and establish distal metastases. In this scenario, as Standard of Care disease management may dictate that low-staged patients are not candidates for recurrence testing, a CTC profile could become a more appropriate indicator of the need for recurrence testing, as opposed to detection of invasive tumor margins pre/post-surgical resection. In addition, while we see that recurrence scores appear not to be correlated to CTC landscape profiles, we consider that the genomic signatures that are used to derive these recurrence risk scores are specific to the primary tumor. The source of tumor material is a core sample, which may not capture the heterogeneity of the most evolved or invasive region of the solid tumor. Therefore, the score may be different and more informative when assessing these metastatic-potential genes from CTCs and/or the leading edge of the tumor. Previous studies have shown that the spatial heterogeneity of cells throughout the tumor are reflective of tumor evolution leading to the most invasive regions and typically have a distinct expression and mutational profile, associated with tumor evolution and coupled disease progression.24-26

The performance of iFCS opens up opportunities in precision medicine which address patient diversity. Specifically, accurately assessing the phenotypes of CTCs can be more reflective of metastatic potential and therefore prognosis. In addition, understanding the mutational profiles within CTCs can assist with creation of personalized cancer vaccines that exploit the distinct functional mutations that may occur in specifically in CTCs (absent in the primary tumor) that subsequently colonize distal metastatic lesions.

REFERENCES

1. Poudineh, M.; Sargent, E. H.; Pantel, K.; Kelley, S. O., Profiling circulating tumour cells and other biomarkers of invasive cancers. *Nat Biomed Eng* 2018, 2, 72-84.
2. Alix-Panabieres, C.; Pantel, K., Clinical prospects of liquid biopsies. *Nat Biomed Eng* 2017, 1.
3. Chaffer, C. L.; Weinberg, R. A., A Perspective on Cancer Cell Metastasis. *Science* 2011, 331, 1559-1564.
4. Lambert, A. W.; Pattabiraman, D. R.; Weinberg, R. A., Emerging Biological Principles of Metastasis. *Cell* 2017, 168, 670-691.
5. Riethdorf, S.; Fritsche, H.; Muller, V.; Rau, T.; Schindibeck, C.; Rack, B.; Janni, W.; Coith, C.; Beck, K.; Janicke, F.; Jackson, S.; Gornet, T.; Cristofanilli, M.; Pantel, K., Detection of circulating tumor cells in peripheral blood of patients with metastatic breast cancer: A validation study of the CellSearch system. *Clin Cancer Res* 2007, 13, 920-928.
6. Romiti, A.; Raffa, S.; Di Rocco, R.; Roberto, M.; Milano, A.; Zullo, A.; Leone, L.; Ranieri, D.; Mazzetta, F.; Medda, E.; Sarcina, I.; Barucca, V.; D'Antonio, C.; Durante, V.; Ferri, M.; Torrisi, M. R.; Marchetti, P., Circulating Tumor Cells Count Predicts Survival in Colorectal Cancer Patients. *J Gastrointest Liver* 2014, 23, 279-284.
7. Bidard, F. C.; Peeters, D. J.; Fehm, T.; Nole, F.; Gisbert-Criado, R.; Mavroudis, D.; Grisanti, S.; Generali, D.; Garcia-Saenz, J. A.; Stebbing, J.; Caldas, C.; Gazzaniga, P.; Manso, L.; Zamarchi, R.; de Lascoiti, A. F.; De Mattos-Arruda, L.; Ignatiadis, M.; Lebofsky, R.; van Laere, S. J.; Meier-Stiegen, F.; Sandri, M. T.; Vidal-Martinez, J.; Politaki, E.; Consoli, F.; Bottini, A.; Diaz-Rubio, E.; Krell, J.; Dawson, S. J.; Raimondi, C.; Rutten, A.; Janni, W.; Munzone, E.; Caranana, V.; Agelaki, S. A.; Almici, C.; Dirix, L.; Solomayer, E. F.; Zorzino, L.; Johannes, H.; Reis, J. S.; Pantel, K.; Pierga, J. Y.; Michiels, S., Clinical validity of circulating tumour cells in patients with metastatic breast cancer: a pooled analysis of individual patient data. *Lancet Oncol* 2014, 15, 406-414.
8. Poudineh, M.; Aldridge, P.; Ahmed, S.; Green, B. J.; Kermanshah, L.; Nguyen, V.; Tu, C.; Mohamadi, R. M.; Nam, R. K.; Hansen, A.; Sridhar, S. S.; Finelli, A.; Fleshner, N. E.; Joshua, A. M.; Sargent, E. H.; Kelley, S. O., Tracking the dynamics of circulating tumour cell phenotypes using nanoparticle-mediated magnetic ranking. *Nat Nanotechnol* 2017, 12, 274-+.
9. Yu, M.; Bardia, A.; Wttner, B. S.; Stott, S. L.; Smas, M. E.; Ting, D. T.; Isakoff, S. J.; Ciciliano, J. C.; Wells, M. N.; Shah, A. M.; Concannon, K. F.; Donaldson, M. C.; Sequist, L. V.; Brachtel, E.; Sgroi, D.; Baselga, J.; Ramaswamy, S.; Toner, M.; Haber, D. A.; Maheswaran, S., Circulating breast tumor cells exhibit dynamic changes in epithelial and mesenchymal composition. *Science* 2013, 339, 580-4.
10. Alix-Panabieres, C.; Pantel, K., OPINION Challenges in circulating tumour cell research. *Nat Rev Cancer* 2014, 14, 623-631.
11. Dasgupta, A.; Lim, A. R.; Ghajar, C. M., Circulating and disseminated tumor cells: harbingers or initiators of metastasis? *Mol Oncol* 2017, 11, 40-61.
12. Lin, H. K.; Zheng, S. Y.; Williams, A. J.; Balic, M.; Groshen, S.; Scher, H. I.; Fleisher, M.; Stadler, W.; Datar, R. H.; Tai, Y. C.; Cote, R. J., Portable Filter-Based Microdevice for Detection and Characterization of Circulating Tumor Cells. *Clin Cancer Res* 2010, 16, 5011-5018.
13. Warkiani, M. E.; Khoo, B. L.; Wu, L. D.; Tay, A. K. P.; Bhagat, A. A. S.; Han, J.; Lim, C. T., Ultra-fast, label-free isolation of circulating tumor cells from blood using spiral microfluidics. *Nat Protoc* 2016, 11, 134-148.
14. Renier, C.; Pao, E.; Che, J.; Liu, H. E.; Lemaire, C. A.; Matsumoto, M.; Triboulet, M.; Srivinas, S.; Jeffrey, S. S.; Rettig, M.; Kulkarni, R. P.; Di Carlo, D.; Sollier-Christen, E., Label-free isolation of prostate circulating tumor cells using Vortex microfluidic technology. *npj Precision Oncology* 2017, 1, 15.
15. Yu, M.; Bardia, A.; Wittner, B.; Stott, S. L.; Smas, M. E.; Ting, D. T.; Isakoff, S. J.; Ciciliano, J. C.; Wells, M. N.; Shah, A. M.; Concannon, K. F.; Donaldson, M. C.; Sequist, L. V.; Brachtel, E.; Sgroi, D.; Baselga, J.; Ramaswamy, S.; Toner, M.; Haber, D. A.; Maheswaran, S., Circulating Breast Tumor Cells Exhibit Dynamic Changes in Epithelial and Mesenchymal Composition. *Science* 2013, 339, 580-584.
16. Alix-Panabieres, C.; Pantel, K., Circulating Tumor Cells: Liquid Biopsy of Cancer. *Clin Chem* 2013, 59, 110-118.
17. Rosensweig, R. E., *Ferrohydrodynamics*. Cambridge University Press: Cambridge, 1985.
18. Zhao, W. J.; Cheng, R.; Jenkins, B. D.; Zhu, T. T.; Okonkwo, N. E.; Jones, C. E.; Davis, M. B.; Kavuri, S. K.; Hao, Z. L.; Schroeder, C.; Mao, L. D., Label-free ferrohydrodynamic cell separation of circulating tumor cells. *Lab Chip* 2017, 17, 3097-3111.
19. Zhao, W. J.; Cheng, R.; Lim, S. H.; Miller, J. R.; Zhang, W. Z.; Tang, W.; Xie, J.; Mao, L. D., Biocompatible and label-free separation of cancer cells from cell culture lines from white blood cells in ferrofluids. *Lab Chip* 2017, 17, 2243-2255.

20. Wirtz, D.; Konstantopoulos, K.; Searson, P. C., The physics of cancer: the role of physical interactions and mechanical forces in metastasis. *Nat Rev Cancer* 2011, 11, 512-22.
21. Fachin, F.; Spuhler, P.; Martel-Foley, J. M.; Edd, J. F.; Barber, T. A.; Walsh, J.; Karabacak, M.; Pai, V.; Yu, M.; Smith, K.; Hwang, H.; Yang, J.; Shah, S.; Yarmush, R.; Sequist, L. V.; Stott, S. L.; Maheswaran, S.; Haber, D. A.; Kapur, R.; Toner, M., Monolithic Chip for High-throughput Blood Cell Depletion to Sort Rare Circulating Tumor Cells. *Sci Rep-Uk* 2017, 7.
22. Ozkumur, E.; Shah, A. M.; Ciciliano, J. C.; Emmink, B. L.; Miyamoto, D. T.; Brachtel, E.; Yu, M.; Chen, P. I.; Morgan, B.; Trautwein, J.; Kimura, A.; Sengupta, S.; Stott, S. L.; Karabacak, N. M.; Barber, T. A.; Walsh, J. R.; Smith, K.; Spuhler, P. S.; Sullivan, J. P.; Lee, R. J.; Ting, D. T.; Luo, X.; Shaw, A. T.; Bardia, A.; Sequist, L. V.; Louis, D. N.; Maheswaran, S.; Kapur, R.; Haber, D. A.; Toner, M., Inertial Focusing for Tumor Antigen-Dependent and -Independent Sorting of Rare Circulating Tumor Cells. *Sci Transl Med* 2013, 5.
23. Karabacak, N. M.; Spuhler, P. S.; Fachin, F.; Lim, E. J.; Pai, V.; Ozkumur, E.; Martel, J. M.; Kojic, N.; Smith, K.; Chen, P. I.; Yang, J.; Hwang, H.; Morgan, B.; Trautwein, J.; Barber, T. A.; Stott, S. L.; Maheswaran, S.; Kapur, R.; Haber, D. A.; Toner, M., Microfluidic, marker-free isolation of circulating tumor cells from blood samples. *Nat Protoc* 2014, 9, 694-710.
24. Natrajan, R.; Sailem, H.; Mardakheh, F. K.; Arias Garcia, M.; Tape, C. J.; Dowsett, M.; Bakal, C.; Yuan, Y., Microenvironmental Heterogeneity Parallels Breast Cancer Progression: A Histology-Genomic Integration Analysis. *PLoS Med* 2016, 13, e1001961.
25. Miller, C. A.; White, B. S.; Dees, N. D.; Griffith, M.; Welch, J. S.; Griffith, O. L.; Vij, R.; Tomasson, M. H.; Graubert, T. A.; Walter, M. J.; Ellis, M. J.; Schierding, W.; DiPersio, J. F.; Ley, T. J.; Mardis, E. R.; Wilson, R. K.; Ding, L., SciClone: inferring clonal architecture and tracking the spatial and temporal patterns of tumor evolution. *PLoS Comput Biol* 2014, 10, e1003665.
26. Yates, L. R.; Gerstung, M.; Knappskog, S.; Desmedt, C.; Gundem, G.; Van Loo, P.; Aas, T.; Alexandrov, L. B.; Larsimont, D.; Davies, H.; Li, Y.; Ju, Y. S.; Ramakrishna, M.; Haugland, H. K.; Lilleng, P. K.; Nik-Zainal, S.; McLaren, S.; Butler, A.; Martin, S.; Glodzik, D.; Menzies, A.; Raine, K.; Hinton, J.; Jones, D.; Mudie, L. J.; Jiang, B.; Vincent, D.; Greene-Colozzi, A.; Adnet, P. Y.; Fatima, A.; Maetens, M.; Ignatiadis, M.; Stratton, M. R.; Sotiriou, C.; Richardson, A. L.; Lonning, P. E.; Wedge, D. C.; Campbell, P. J., Subclonal diversification of primary breast cancer revealed by multiregion sequencing. *Nat Med* 2015, 21, 751-9.

REFERENCES FROM SUPP INFO

1. S. Riethdorf, H. Fritsche, V. Muller, T. Rau, C. Schindibeck, B. Rack, W. Janni, C. Coith, K. Beck, F. Janicke, S. Jackson, T. Gornet, M. Cristofanilli and K. Pantel, *Clin Cancer Res*, 2007, 13, 920-928.
2. A. H. Talasaz, A. A. Powell, D. E. Huber, J. G. Berbee, K. H. Roh, W. Yu, W. Z. Xiao, M. M. Davis, R. F. Pease, M. N. Mindrinos, S. S. Jeffrey and R. W. Davis, *Proceedings of the National Academy of Sciences of the United States of America*, 2009, 106, 3970-3975.
3. S. Nagrath, L. V. Sequist, S. Maheswaran, D. W. Bell, D. Irimia, L. Ulkus, M. R. Smith, E. L. Kwak, S. Digumarthy, A. Muzikansky, P. Ryan, U. J. Balis, R. G. Tompkins, D. A. Haber and M. Toner, *Nature*, 2007, 450, 1235-U1210.
4. J. P. Gleghorn, E. D. Pratt, D. Denning, H. Liu, N. H. Bander, S. T. Tagawa, D. M. Nanus, P. A. Giannakakou and B. J. Kirby, *Lab Chip*, 2010, 10, 27-29.
5. S. D. Mikolajczyk, L. S. Millar, P. Tsinberg, S. M. Coutts, M. Zomorrodi, T. Pham, F. Z. Bischoff and T. J. Pircher, *Journal of Oncology*, 2011,
6. Y. T. Lu, L. B. Zhao, Q. L. Shen, M. A. Garcia, D. X. Wu, S. Hou, M. Song, X. C. Xu, W. H. OuYang, W. W. L. OuYang, J. Lichterman, Z. Luo, X. Xuan, J. T. Huang, L. W. K. Chung, M. Rettig, H. R. Tseng, C. Shao and E. M. Posadas, *Methods*, 2013, 64, 144-152.
7. S. L. Stott, C. H. Hsu, D. I. Tsukrov, M. Yu, D. T. Miyamoto, B. A. Waltman, S. M. Rothenberg, A. M. Shah, M. E. Smas, G. K. Korir, F. P. Floyd, A. J. Gilman, J. B. Lord, D. Winokur, S. Springer, D. Irimia, S. Nagrath, L. V. Sequist, R. J. Lee, K. J. Isselbacher, S. Maheswaran, D. A. Haber and M. Toner, *Proceedings of the National Academy of Sciences of the United States of America*, 2010, 107, 18392-18397.
8. W. A. Sheng, O. O. Ogunwobi, T. Chen, J. L. Zhang, T. J. George, C. Liu and Z. H. Fan, *Lab Chip*, 2014, 14, 89-98.
9. H. J. Yoon, T. H. Kim, Z. Zhang, E. Azizi, T. M. Pham, C. Paoletti, J. Lin, N. Ramnath, M. S. Wicha, D. F. Hayes, D. M. Simeone and S. Nagrath, *Nature nanotechnology*, 2013, 8.
10. J. Autebert, B. Coudert, J. Champ, L. Saias, E. T. Guneri, R. Lebofsky, F. C. Bidard, J. Y. Pierga, F. Farace, S. Descroix, L. Malaquin and J. L. Viovy, *Lab Chip*, 2015, 15, 2090-2101.
11. C. M. Earhart, C. E. Hughes, R. S. Gaster, C. C. Ooi, R. J. Wilson, L. Y. Zhou, E. W. Humke, L. Y. Xu, D. J. Wong, S. B. Willingham, E. J. Schwartz, I. L. Weissman, S. S. Jeffrey, J. W. Neal, R. Rohatgi, H. A. Wakeleebe and S. X. Wang, *Lab Chip*, 2014, 14, 78-88.
12. W. Harb, A. Fan, T. Tran, D. C. Danila, D. Keys, M. Schwartz and C. Ionescu-Zanetti, *Transl Oncol*, 2013, 6, 528-+.
13. E. Ozkumur, A. M. Shah, J. C. Ciciliano, B. L. Emmink, D. T. Miyamoto, E. Brachtel, M. Yu, P. I. Chen, B. Morgan, J. Trautwein, A. Kimura, S. Sengupta, S. L. Stott, N. M. Karabacak, T. A. Barber, J. R. Walsh, K. Smith, P. S. Spuhler, J. P. Sullivan, R. J. Lee, D. T. Ting, X. Luo, A. T. Shaw, A. Bardia, L. V. Sequist, D. N. Louis, S. Maheswaran, R. Kapur, D. A. Haber and M. Toner, *Science translational medicine*, 2013, 5.
14. J. H. Kang, S. Krause, H. Tobin, A. Mammoto, M. Kanapathipillai and D. E. Ingber, *Lab Chip*, 2012, 12, 2175-2181.
15. M. Tang, C. Y. Wen, L. L. Wu, S. L. Hong, J. Hu, C. M. Xu, D. W. Pang and Z. L. Zhang, *Lab Chip*, 2016, 16, 1214-1223.
16. K. Hoshino, Y. Y. Huang, N. Lane, M. Huebschman, J. W. Uhr, E. P. Frenkel and X. J. Zhang, *Lab Chip*, 2011, 11, 3449-3457.
17. O. Lara, X. D. Tong, M. Zborowski and J. J. Chalmers, *Exp Hematol*, 2004, 32, 891-904.
18. Z. A. Liu, A. Fusi, E. Klopocki, A. Schmittel, I. Tinhofer, A. Nonnenmacher and U. Keilholz, *J Transl Med*, 2011, 9.
19. F. Fachin, P. Spuhler, J. M. Martel-Foley, J. F. Edd, T. A. Barber, J. Walsh, M. Karabacak, V. Pai, M. Yu, K. Smith, H. Hwang, J. Yang, S. Shah, R. Yarmush, L. V. Sequist, S. L. Stott, S. Maheswaran, D. A. Haber, R. Kapur and M. Toner, *Sci Rep-Uk,* 2017, 7.
20. J. Weitz, P. Kienle, J. Lacroix, F. Wlleke, A. Benner, T. Lehnert, C. Herfarth and M. von Knebel Doeberitz, *Clin Cancer Res,* 1998, 4, 343-348.
21. G. A. Clawson, E. Kimchi, S. D. Patrick, P. Xin, R. Harouaka, S. Zheng, A. Berg, T. Schell, K. F. Staveley-O'Carroll, R. I. Neves, P. J. Mosca and D. Thiboutot, *PLoS One,* 2012, 7, e41052.
22. W. He, S. A. Kularatne, K. R. Kalli, F. G. Prendergast, R. J. Amato, G. G. Klee, L. C. Hartmann and P. S. Low, *Int J Cancer,* 2008, 123, 1968-1973.
23. D. E. Campton, A. B. Ramirez, J. J. Nordberg, N. Drovetto, A. C. Clein, P. Varshayskaya, B. H. Friemel, S. Quarre, A. Breman, M. Dorschner, S. Blau, C. A. Blau, D. E. Sabath, J. L. Stilwell and E. P. Kaldjian, *BMC Cancer,* 2015, 15, 360.
24. G. Vona, A. Sabile, M. Louha, V. Sitruk, S. Romana, K. Schutze, F. Capron, D. Franco, M. Pazzagli, M. Vekemans, B. Lacour, C. Brechot and P. Paterlini-Brechot, *Am J Pathol,* 2000, 156, 57-63.
25. I. Desitter, B. S. Guerrouahen, N. Benali-Furet, J. Wechsler, P. A. Janne, Y. Kuang, M. Yanagita, L. Wang, J. A. Berkowitz, R. J. Distel and Y. E. Cayre, *Anticancer Res,* 2011, 31, 427-441.
26. D. L. Adams, S. S. Martin, R. K. Alpaugh, M. Charpentier, S. Tsai, R. C. Bergan, I. M. Ogden, W. Catalona, S. Chumsri, C.-M. Tang and M. Cristofanilli, 2014, DOI: 10.1073/pnas.1320198111% J Proceedings of the National Academy of Sciences, 201320198.
27. R. A. Harouaka, M. D. Zhou, Y. T. Yeh, W. J. Khan, A. Das, X. Liu, C. C. Christ, D. T. Dicker, T. S. Baney, J. T. Kaifi, C. P. Belani, C. I. Truica, W. S. El-Deiry, J. P. Allerton and S. Y. Zheng, *Clin Chem,* 2014, 60, 323-333.
28. M. D. Zhou, S. Hao, A. J. Williams, R. A. Harouaka, B. Schrand, S. Rawal, Z. Ao, R. Brenneman, E. Gilboa, B. Lu, S. Wang, J. Zhu, R. Datar, R. Cote, Y. C. Tai and S. Y. Zheng, *Sci Rep,* 2014, 4, 7392.
29. X. Qin, S. Park, S. P. Duffy, K. Matthews, R. R. Ang, T. Todenhofer, H. Abdi, A. Azad, J. Bazov, K. N. Chi, P. C. Black and H. Ma, *Lab Chip,* 2015, 15, 2278-2286.
30. A. F. Sarioglu, N. Aceto, N. Kojic, M. C. Donaldson, M. Zeinali, B. Hamza, A. Engstrom, H. Zhu, T. K. Sundaresan, D. T. Miyamoto, X. Luo, A. Bardia, B. S. Wttner, S. Ramaswamy, T. Shioda, D. T. Ting, S. L. Stott, R. Kapur, S. Maheswaran, D. A. Haber and M. Toner, *Nat Methods,* 2015, 12, 685-691.
31. E. Sollier, D. E. Go, J. Che, D. R. Gossett, S. O'Byrne, W. M. Weaver, N. Kummer, M. Rettig, J. Goldman, N. Nickols, S. McCloskey, R. P. Kulkarni and D. Di Carlo, *Lab Chip,* 2014, 14, 63-77.
32. H. W. Hou, M. E. Warkiani, B. L. Khoo, Z. R. Li, R. A. Soo, D. S. Tan, W. T. Lim, J. Han, A. A. Bhagat and C. T. Lim, *Sci Rep,* 2013, 3, 1259.
33. V. Gupta, I. Jafferji, M. Garza, V. O. Melnikova, D. K. Hasegawa, R. Pethig and D. W. Davis, *Biomicrofluidics,* 2012, 6, 24133.
34. P. Li, Z. Mao, Z. Peng, L. Zhou, Y. Chen, P. H. Huang, C. I. Truica, J. J. Drabick, W. S. El-Deiry, M. Dao, S. Suresh and T. J. Huang, *Proc Natl Acad Sci USA,* 2015, 112, 4970-4975.
35. M. Antfolk, C. Antfolk, H. Lilja, T. Laurell and P. Augustsson, *Lab Chip,* 2015, 15, 2102-2109.
36. W. Zhao, R. Cheng, B. D. Jenkins, T. Zhu, N. E. Okonkwo, C. E. Jones, M. B. Davis, S. K. Kavuri, Z. Hao, C. Schroeder and L. Mao, *Lab Chip,* 2017, 17, 3097-3111.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A cell separation system for enriching circulating tumor cells in a biological sample, the system comprising:
   a plurality of magnetic microbeads adapted for conjugation to white blood cells in the biological sample, and not for conjugation with the circulating tumor cells, to provide a magnetically labeled biological sample wherein a majority of the white blood cells in the biological sample are each conjugated to one or more of the plurality of magnetic microbeads;
   a biocompatible superparamagnetic sheathing composition comprising a plurality of magnetic nanoparticles and a biocompatible surfactant, the biocompatible superparamagnetic sheathing composition adapted to be combined with a biocompatible carrier fluid to make a biocompatible superparamagnetic sheathing fluid; and
   a multi-stage microfluidic device, the device comprising:
   (i) a filter section comprising a first microfluidic channel, a first fluid inlet, and one or more filters along a length of the first microfluidic channel, wherein the first fluid inlet is configured to receive the magnetically labeled biological sample, and wherein the one or more filters are configured to remove a first plurality of waste particles from the magnetically labeled biological sample;
   (ii) a first separation stage comprising a second microfluidic channel fluidly connected to the first microfluidic channel and having a second fluid inlet to receive the biocompatible superparamagnetic sheathing fluid, and a first fluid outlet at an end of the second microfluidic channel and offset from a central diameter of the second microfluidic channel, wherein the second microfluidic channel is configured to combine the magnetically labeled biological sample from the filter section with the biocompatible superparamagnetic sheathing fluid;
   (iii) a second separation stage comprising a third microfluidic channel fluidly connected to the second microfluidic channel and having a second fluid outlet and at least a first circulating tumor cell outlet and second circulating tumor cell outlet; and
   (iv) one or more magnetic sources adjacent to the multi-stage microfluidic device and configured to produce:
      (a) a non-uniform magnetic field along the second microfluidic channel having a component sufficiently perpendicular to a length of the second microfluidic channel to cause a plurality of white blood cells conjugated to the magnetic beads to be deflected into the first fluid outlet; and
      (b) a substantially symmetric magnetic field having a field maximum along a length of the third microfluidic channel sufficient to cause the white blood cells conjugated to the magnetic beads in the third microfluidic channel to be focused toward a center of the third microfluidic channel and to exit the channel via the second fluid outlet and to cause circulating tumor cells to be deflected towards an outer portion of the third microfluidic channel and to exit the channel via the first or second circulating tumor cell outlet.

2. The cell separation system of claim 1, wherein the multi-stage microfluidic device has a serpentine shape and wherein:
- the filter section comprises a first end and a second end fluidly connected by the first microfluidic channel, wherein the first fluid inlet is fluidly connected to the first microfluidic channel at the first end, and the one or more filters are located between the first and second end of the first microfluidic channel;
- the first separation stage comprises a third end and fourth end fluidly connected by the second microfluidic channel, wherein the third end is connected to the second end of the first microfluidic channel of the filter section by a first u-shaped channel, wherein the second fluid inlet is fluidly connected to the second microfluidic channel at the third end and the first fluid outlet is fluidly connected to the second microfluidic channel at the fourth end; and
- the second separation stage comprises a fifth end and a sixth end fluidly connected by the third microfluidic channel, wherein the fifth end is connected to the fourth end of the second microfluidic channel of the first separation stage by a second u-shaped channel, wherein the second fluid outlet is fluidly connected to the third microfluidic channel at the sixth end and configured to receive materials flowing through a central portion of the third microfluidic channel, and wherein the first and second circulating tumor cell outlets are each fluidly connected to the third microfluidic channel at the sixth end and offset from the center of the third microfluidic channel and configured to receive material flowing near the outer portion of the third microfluidic channel.

3. The cell separation system according to claim 1, wherein the first fluid outlet is offset from a central diameter of the second microfluidic channel and configured to receive white blood cells conjugated to magnetic beads and flowing on one side of the second microfluidic channel.

4. The cell separation system according to claim 1, wherein the one or more magnetic sources comprises a first magnet array and a second magnet array arranged in a quadrupole configuration such that the first magnet array and the second magnet array are oriented to repel each other;
- wherein the first separation stage is between the first magnet array and the second magnet array and oriented such that the length of the third microfluidic channel is centrally aligned between the first magnet array and the second magnet array.

5. The cell separation system according to claim 4, wherein a vertical distance between the third microfluidic channel and each of the first magnet array and the second magnet array is about 800-1200 µm.

6. The cell separation system according to claim 1, wherein one or more of the first microfluidic channel, the second microfluidic channel, and the third microfluidic channel have a thickness of about 100 µm to about 500 µm.

7. The cell separation system according to claim 1, wherein the second microfluidic channel has a width of about 1400 µm to 1800 µm and the third microfluidic channel has a width of about 1000 µm to 1400 µm.

8. The cell separation system according to claim 1, wherein the circulating tumor cells that exit via the first and second circulating tumor cell outlet comprise about 97%, or more, of the total number of circulating tumor cells present in the biological sample inserted into the first fluid inlet when in operation.

9. The cell separation system according to claim 1, wherein the biological sample is selected from the group consisting of: whole blood and whole blood that has been treated with lysis buffer to lyse red blood cells, wherein the biological sample comprises a plurality of components.

10. The cell separation system according to claim 1, wherein about 95% to 100%, of the white blood cells are each conjugated to one or more of the plurality of magnetic microbeads.

11. The cell separation system according to claim 1, wherein a majority of the white blood cells in the magnetically labeled biological sample are each conjugated to about 1 to about 60 magnetic microbeads.

12. The cell separation system according to claim 1, wherein a majority of the white blood cells in the magnetically labeled biological sample are each conjugated to an average of about 20-50 magnetic microbeads.

13. The cell separation system according to claim 1, wherein the one or more magnetic sources produce a flux density of about 0.4 to 0.6T in the first separation stage and about 1.3 to 1.5 T in the second separation stage.

14. The cell separation system according to claim 1, wherein the one or more magnetic sources produce a flux density gradient that ranges from about 4 to 256 T m$^{-1}$ in the first separation stage and from about 0-625 T m$^{-1}$ in the second separation stage, wherein the flux density gradient is lower at the center of the third microfluidic channel of the second separation stage than at the outer portion of the third microfluidic channel of the second separation stage.

15. The cell separation system according to claim 1, wherein the biological sample comprises about 1 to 1000 circulating tumor cells per milliliter of the biological sample.

16. The cell separation system according to claim 1, wherein the circulating tumor cells are selected from the group consisting of a primary cancer cell, a lung cancer cell, a prostate cancer cell, a breast cancer cell, a pancreatic cancer cell, and a combination thereof.

17. The cell separation system according to claim 1, wherein the plurality of magnetic microbeads are conjugated with leukocyte antibodies for binding white blood cells in the biological sample.

18. A multi-stage microfluidic device for enriching circulating tumor cells in a biological sample, the device comprising:
- (i) a filter section comprising a first microfluidic channel, a first fluid inlet, and one or more filters along a length of the first microfluidic channel, wherein the first fluid inlet is configured to receive a biological sample comprising circulating tumor cells and white blood cells, wherein a majority of the white blood cells in the biological sample are each conjugated to magnetic microbeads, and wherein the one or more filters are configured to remove a first plurality of waste particles from the biological sample;
- (ii) a first separation stage comprising a second microfluidic channel fluidly connected to the first microfluidic channel and having a second fluid inlet to receive a biocompatible superparamagnetic sheathing fluid, and a first fluid outlet at an end of the second microfluidic channel opposite the second fluid inlet and offset from a central diameter of the second microfluidic channel, wherein the second microfluidic channel is configured to combine the biological sample from the first filter section with the biocompatible superparamagnetic sheathing fluid, and wherein the biocompatible superparamagnetic sheathing fluid comprises a plurality of magnetic nanoparticles and a biocompatible surfactant suspended in a biocompatible carrier fluid;

(iii) a second separation stage comprising a third microfluidic channel fluidly connected to the second microfluidic channel and having a second fluid outlet and at least a first circulating tumor cell outlet and second circulating tumor cell outlet; and (iv) one or more magnetic sources adjacent to the multi-stage microfluidic device and configured to produce:

(a) a non-uniform magnetic field along the second microfluidic channel having a component sufficiently perpendicular to a length of the second microfluidic channel to cause a plurality of white blood cells conjugated to the magnetic beads to be deflected into the first fluid outlet; and (b) a substantially symmetric magnetic field having a field maximum along a length of the third microfluidic channel sufficient to cause the white blood cells conjugated to the magnetic beads in the third microfluidic channel to be focused toward a center of the third microfluidic channel and to exit the channel via the second fluid outlet and to cause circulating tumor cells to be deflected towards an outer portion of the third microfluidic channel and to exit the channel via the first or second circulating tumor cell outlet.

19. The multi-stage microfluidic device of claim 18, wherein the device has a serpentine shape and wherein the filter section is fluidly connected to the first separation stage by a first u-shaped channel and wherein the first separation stage is fluidly connected to the second separation stage by a second u-shaped channel.

20. The multi-stage microfluidic device of claim 18, wherein the one or more magnetic sources comprise a first magnet array and a second magnet array arranged in a quadrupole configuration such that the first magnet array and the second magnet array are oriented to repel each other;

wherein the second separation stage is between the first magnet array and the second magnet array and oriented such that the length of the third microfluidic channel is centrally aligned between the first magnet array and the second magnet array.

* * * * *